US006458787B1

(12) United States Patent
Martins et al.

(10) Patent No.: US 6,458,787 B1
(45) Date of Patent: *Oct. 1, 2002

(54) CYCLIC AMP-SPECIFIC PHOSPHODIESTERASE INHIBITORS

(75) Inventors: Timothy J. Martins, Bothell; Kerry W. Fowler, Seattle; Joshua Odingo, Everett; Edward A. Kesicki; Amy Oliver, both of Bothell, all of WA (US); Laurence E. Burgess; John J. Gaudino, both of Boulder, CO (US); Zachary S. Jones, Westminster, CO (US); Bradley J. Newhouse, Broomfield, CO (US); Stephen T. Schlacter, Boulder, CO (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/847,424

(22) Filed: May 2, 2001

Related U.S. Application Data

(62) Division of application No. 09/471,846, filed on Dec. 23, 1999, now Pat. No. 6,258,833.

(51) Int. Cl.[7] ............... A61K 31/535; A61K 31/44; C07D 413/04; C07D 207/06
(52) U.S. Cl. ............ 514/231.5; 514/252.13; 514/300; 514/367; 544/141; 544/372; 544/335; 546/281.1; 548/518; 548/530; 548/540
(58) Field of Search ............... 548/518, 530, 548/540; 544/141, 372, 335; 514/231.5, 252.13; 546/281.1; 549/429

(56) References Cited

U.S. PATENT DOCUMENTS 5,665,754 A 9/1997 Feldman et al. ............ 514/397
5,998,428 A 12/1999 Barnette et al. ............ 514/285

OTHER PUBLICATIONS

Schultz et al., "Rolipram, a stereospecific inhibitor of calmodulin–independent phosphodiesterase, cause β–adrenoceptor subsensitivity in rat cerebral cortex," *Naunyn–Schmiedeberg's Arch Pharmacol*, 333, pp. 23–30 (1986).
Ma et al., Asymmetric dipolar cycloaddition reactions: a practical, convergent synthesis of chiral pyrrolidines, *Tetrahedron: Asymmetry*, vol. 8, No. 6, pp. 883–887 (1997).
Robichaud et al., "Emesis induced by inhibitors of type IV cyclic nucleotide phosehodiesterase (PDE IV) in the ferret," *Neuropharmacology*, 38, pp. 289–297 (1999).
Allen et al., Development of a recombinant cell–based system for the characterisation of phosphodiesterase 4 isoforms and evaluation of inhibitors, *Biochemical Pharmacology*, vol. 57, pp. 1375–1382. (1999).

J. Beavo et al., "Cyclic nucleotide phosphodiesterases: Structure, regulation and drug action," Wiley and Sons, Chichester, pp. 3–14 (1990).
T.J. Trophy et al., *Drug News and Perspectives*, 6, pp. 203–214 (1993).
M.A. Giembycz et al., *Clin. Exp. Allergy*, 22, pp. 337–344 (1992).
J. Semmler et al., *Int. J. Immunopharmacol.*, 15, pp. 409–413 (1993).
K.L. Molnar–Kimber et al., *Mediators of Inflammation*, 1, pp. 411–417 (1992).
M.W. Verghese et al., *J. Mol. Cell. Cardiiol.*, 21 (Suppl. 2), S61 (1989).
C.P. Nielson et al., *J. Allergy Immunol.*, 86, pp. 801–808 (1990).
P.T. Peachell et al., *J. Immunol.*, 148, pp. 2503–2510 (1992).
G. Dent et al., *J. Pharmacol.*, 103, pp. 1339–1346 (1991).
S.A. Robicsek et al., *Biochem. Pharmacol.*, 42, pp. 869–877 (1991).
H.S. Dhillon et al., *J. Neurotrauma*, 12, pp. 1035–1043 (1995).
N. Suttorp et al., *J. Clin. Invest.*, 91, pp. 1421–1428 (1993).
M.R. Bristow et al., *Circulation*, 97, pp. 1340–1341 (1998).
G. Poli et al., *Proc. Natl. Acad. Sci. USA*, 87, pp. 782–785 (1990).
P. Orosz et al., *J. Exp. Med.*, 117, pp. 1391–1398 (1993).
M. Mentz et al., *Blood*, 88, pp. 2172–2182 (1996).
S. Takeda et al., *Kidney Int.*, 37, p. 362 (1990).
D. Chabardea et al., *Kidney Int.*, 35, p. 494 (1989).
C.D. Nicholson, *Psychopharmacology*, 101, p. 147 (1990).
F. Eckmann et al., *Curr. Ther. Res.*, 43, p 291 (1988).
A. Klodzinska et al., *Neuropharnacology*, 38, p. 1831 (1991).
H. Kato et al., *Eur. J. Pharmacol.*, 272, p. 107 (1995).
G. Gardos et al., *J. Clin. Pharmocol.*, 16, p. 304 (1976).
I. Shoulson et al., *Neurology*, 25, p. 722 (1975).
T. Hayakawa et al., *Clin. Exp. Pharmacol. Physiol.*, 26, p. 421 (1999).
R.D. Porsolt et al., *Eur. J. Pharmacol.*, 47, p. 379 (1978).
R.D. Porsolt et al., *Eur. J. Pharmacol.*, 57, p. 431 (1979).
L. Steru, *Psychopharmacology*, 85, p. 376 (1985).
M. Takahashi, *J. Neuroscience*, 19, p. 610 (1999).
D. Pinsky et al., *J. Clin. Invest.*, 92, pp. 2994–3002 (1993).
*Antidepressants: neurochemical, behavioral and clinical prospectives*, Enna, Malick, and Richelson, eds., Raven Press, pp. 121–139 (1981).

*Primary Examiner*—Johann Richter
*Assistant Examiner*—Ebenezer Sackey
(74) *Attorney, Agent, or Firm*—Marshall, Gerstein & Borun.

(57) ABSTRACT

Novel pyrrolidine compounds that are potent and selective inhibitors of PDE4, as well as methods of making the same, are disclosed. Use of the compounds in the treatment of inflammatory diseases and other diseases involving elevated levels of cytokines, as well as central nervous system (CNS) disorders, also is disclosed.

22 Claims, No Drawings

CYCLIC AMP-SPECIFIC PHOSPHODIESTERASE INHIBITORS

CROSS-REFERENCE TO RELATED APPLICATION

This is a divisional of U.S. application Ser. No. 09/471,846, filed Dec. 23, 1999, now U.S. Pat. No. 6,258,833.

FIELD OF INVENTION

The present invention relates to a series of compounds that are potent and selective inhibitors of cyclic adenosine 3',5'-monophosphate specific phosphodiesterase (cAMP specific PDE). In particular, the present invention relates to a series of novel pyrrolidine compounds which are useful for inhibiting the function of cAMP specific PDE, in particular, PDE4, as well as methods of making the same, pharmaceutical compositions containing the same, and their use as therapeutic agents, for example, in treating inflammatory diseases and other diseases involving elevated levels of cytokines and proinflammatory mediators.

BACKGROUND OF THE INVENTION

Chronic inflammation is a multi-factorial disease complication characterized by activation of multiple types of inflammatory cells, particularly cells of lymphoid lineage (including T lymphocytes) and myeloid lineage (including granulocytes, macrophages, and monocytes). Proinflammatory mediators, including cytokines, such as tumor necrosis factor (TNF) and interleukin-1 (IL-1), are produced by these activated cells. Accordingly, an agent that suppresses the activation of these cells, or their production of proinflammatory cytokines, would be useful in the therapeutic treatment of inflammatory diseases and other diseases involving elevated levels of cytokines.

Cyclic adenosine monophosphate (cAMP) is a second messenger that mediates the biologic responses of cells to a wide range of extracellular stimuli. When the appropriate agonist binds to specific cell surface receptors, adenylate cyclase is activated to convert adenosine triphosphate (ATP) to cAMP. It is theorized that the agonist induced actions of cAMP within the cell are mediated predominately by the action of cAMP-dependent protein kinases. The intracellular actions of cAMP are terminated by either a transport of the nucleotide to the outside of the cell, or by enzymatic cleavage by cyclic nucleotide phosphodiesterases (PDEs), which hydrolyze the 3'-phosphodiester bond to form 5'-adenosine monophosphate (5'-AMP). 5'-AMP is an inactive metabolite. The structures of cAMP and 5'-AMP are illustrated below.

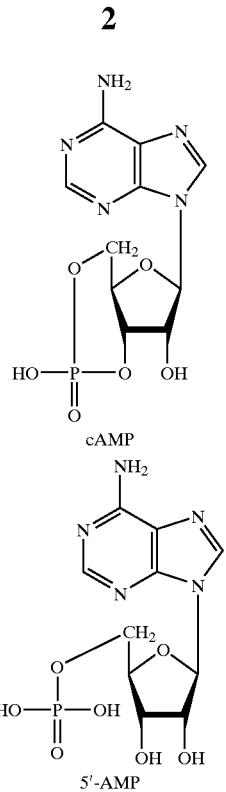

Elevated levels of cAMP in human myeloid and lymphoid lineage cells are associated with the suppression of cell activation. The intracellular enzyme family of PDEs, therefore, regulates the level of cAMP in cells. PDE4 is a predominant PDE isotype in these cells, and is a major contributor to cAMP degradation. Accordingly, the inhibition of PDE function would prevent the conversion of cAMP to the inactive metabolite 5'-AMP and, consequently, maintain higher cAMP levels, and, accordingly, suppress cell activation (see Beavo et al., "Cyclic Nucleotide Phosphodiesterases: Structure, Regulation and Drug Action," Wiley and Sons, Chichester, pp. 3–14, (1990)); Torphy et al., *Drug News and Perspectives*, 6, pp. 203–214 (1993); Giembycz et al., *Clin. Exp. Allergy*, 22, pp. 337–344 (1992)).

In particular, PDE4 inhibitors, such as rolipram, have been shown to inhibit production of TNFα and partially inhibit IL-1β release by monocytes (see Semmler et al., *Int. J. Immunopharmacol.*, 15, pp. 409–413, (1993); Molnar-Kimber et al., *Mediators of Inflammation*, 1, pp. 411–417, (1992)). PDE4 inhibitors also have been shown to inhibit the production of superoxide radicals from human polymorphonuclear leukocytes (see Verghese et al., *J. Mol. Cell. Cardiol.*, 21 (Suppl. 2), S61 (1989); Nielson et al.,*J. Allergy Immunol.*, 86, pp. 801–808, (1990)); to inhibit the release of vasoactive amines and prostanoids from human basophils (see Peachell et al., *J. Immunol.*, 148, pp. 2503–2510, (1992)); to inhibit respiratory bursts in eosinophils (see Dent et al., *J. Pharmacol.*, 103, pp. 1339–1346, (1991)); and to inhibit the activation of human T-lymphocytes (see Robicsek et al., *Biochem. Pharmacol.*, 42, pp. 869–877, (1991)).

Inflammatory cell activation and excessive or unregulated cytokine (e.g., TNFα and IL-1,β) production are implicated in allergic, autoimmune, and inflammatory diseases and disorders, such as rheumatoid arthritis, osteoarthritis, gouty arthritis, spondylitis, thyroid associated ophthalmopathy, Behcet's disease, sepsis, septic shock, endotoxic shock, gram negative sepsis, gram positive sepsis, toxic shock syndrome, asthma, chronic bronchitis, adult respiratory distress syndrome, chronic pulmonary inflammatory disease, such as chronic obstructive pulmonary disease, silicosis, pulmonary sarcoidosis, reperfusion injury of the myocardium, brain, and extremities, fibrosis, cystic fibrosis, keloid formation, scar formation, atherosclerosis, transplant rejection disorders, such as graft vs. host reaction and allograft rejection, chronic glomerulonephritis, lupus, inflammatory bowel disease, such as Crohn's disease and ulcerative colitis, proliferative lymphocyte diseases, such as leukemia, and inflammatory dermatoses, such as atopic dermatitis, psoriasis, and urticaria.

Other conditions characterized by elevated cytokine levels include brain injury due to moderate trauma (see Dhillon et al., *J. Neurotrauma*, 12, pp. 1035–1043 (1995); Suttorp et al., *J. Clin. Invest.*, 91, pp. 1421–1428 (1993)), cardiomyopathies, such as congestive heart failure (see Bristow et al., *Circulation*, 97, pp. 1340–1341 (1998)), cachexia, cachexia secondary to infection or malignancy, cachexia secondary to acquired immune deficiency syndrome (AIDS), ARC (AIDS related complex), fever myalgias due to infection, cerebral malaria, osteoporosis and bone resorption diseases, keloid formation, scar tissue formation, and pyrexia.

In particular, TNFα has been identified as having a role with respect to human acquired immune deficiency syndrome (AIDS). AIDS results from the infection of T-lymphocytes with Human Immunodeficiency Virus (HIV). Although HIV also infects and is maintained in myeloid lineage cells, TNF has been shown to upregulate HIV infection in T-lymphocytic and monocytic cells (see Poli et al., *Proc. Natl. Acad. Sci. USA*, 87, pp. 782–785, (1990)).

Several properties of TNFα, such as stimulation of collagenases, stimulation of angiogenesis in vivo, stimulation of bone resorption, and an ability to increase the adherence of tumor cells to endothelium, are consistent with a role for TNF in the development and metastatic spread of cancer in the host. TNFα recently has been directly implicated in the promotion of growth and metastasis of tumor cells (see Orosz et al., *J. Exp. Med.*, 177, pp. 1391–1398, (1993)).

PDE4 has a wide tissue distribution. There are at least four genes for PDE4 of which multiple transcripts from any given gene can yield several different proteins that share identical catalytic sites. The amino acid identity between the four possible catalytic sites is greater than 85%. Their shared sensitivity to inhibitors and their kinetic similarity reflect the functional aspect of this level of amino acid identity. It is theorized that the role of these alternatively expressed PDE4 proteins allows a mechanism by which a cell can differentially localize these enzymes intracellularly and/or regulate the catalytic efficiency via post translational modification. Any given cell type that expresses the PDE4 enzyme typically expresses more than one of the four possible genes encoding these proteins.

Investigators have shown considerable interest in the use of PDE4 inhibitors as anti-inflammatory agents Early evidence indicates that PDE4 inhibition has beneficial effects on a variety of inflammatory cells such as monocytes, macrophages, T-cells of the Th-1 lineage, and granulocytes. The synthesis and/or release of many proinflammatory mediators, such as cytokines, lipid mediators, superoxide, and biogenic amines, such as histamine, have been attenuated in these cells by the action of PDE4 inhibitors. The PDE4 inhibitors also affect other cellular functions including T-cell proliferation, granulocyte transmigration in response to chemotoxic substances, and integrity of endothelial cell junctions within the vasculature.

The design, synthesis, and screening of various PDE4 inhibitors have been reported. Methylxanthines, such as caffeine and theophylline, were the first PDE inhibitors discovered, but these compounds are nonselective with respect to which PDE is inhibited. The drug rolipram, an antidepressant agent, was one of the first reported specific PDE4 inhibitors. Rolipram, having the following structural formula, has a reported 50% Inhibitory Concentration ($IC_{50}$) of about 200 nM (nanomolar) with respect to inhibiting recombinant human PDE4.

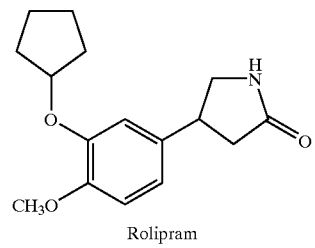

Rolipram

Investigators have continued to search for PDE4 inhibitors that are more selective with respect to inhibiting PDE4, that have a lower $IC_{50}$ than rolipram, and that avoid the undesirable central nervous system (CNS) side effects, such as retching, vomiting, and sedation, associated with the administration of rolipram. One class of compounds is disclosed in Feldman et al. U.S. Pat. No. 5,665,754. The compounds disclosed therein are substituted pyrrolidines having a structure similar to rolipram. One particular compound, having structural formula (I), has an $IC_{50}$ with respect to human recombinant PDE4 of about 2 nM. Inasmuch as a favorable separation of emetic side effect from efficacy was observed, these compounds did not exhibit a reduction in undesirable CNS effects.

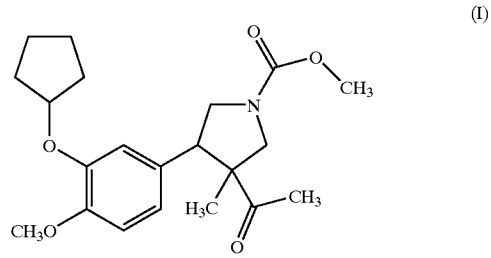

(I)

In addition, several companies are now undertaking clinical trials of other PDE4 inhibitors. However, problems relating to efficacy and adverse side effects, such as emesis and central nervous system disturbances, remain unsolved.

Accordingly, compounds that selectively inhibit PDE4, and that reduce or eliminate the adverse CNS side effects associated with prior PDE4 inhibitors, would be useful in the treatment of allergic and inflammatory diseases, and other diseases associated with excessive or unregulated production of cytokines, such as TNF. In addition, selective PDE4 inhibitors would be useful in the treatment of diseases that are associated with elevated cAMP levels or PDE4 function in a particular target tissue.

SUMMARY OF THE INVENTION

The present invention is directed to potent and selective PDE4 inhibitors useful in treatment of diseases and conditions where inhibition of PDE4 activity is considered beneficial. The present PDE4 inhibitors unexpectedly reduce or eliminate the adverse CNS side effects associated with prior PDE4 inhibitors.

In particular, the present invention is directed to pyrrolidine compounds having the structural formula (II):

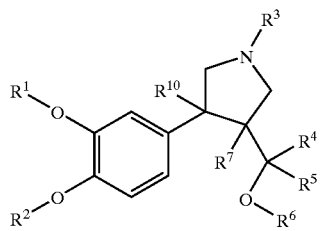

(II)

wherein $R^1$ is lower alkyl, bridged alkyl (e.g., norbornyl), aralkyl (e.g., indanyl), cycloalkyl, a 5- or 6-membered saturated heterocycle (e.g., 3-tetrahydrofuryl), $C_{13}$ alkylenecycloalkyl (e.g., cyclopentylmethyl), aryl- or heteroaryl-substituted propargyl (e.g., —CH$_2$C≡C—C$_6$H$_5$), aryl- or heteroaryl-substituted allyl (e.g., —CH$_2$CH=CH—C$_6$H$_5$), or halocycloalkyl (e.g., fluorocyclopentyl);

$R^2$ is hydrogen, methyl, or halo-substituted methyl, e.g., CHF$_2$;

$R^3$ is C(=O)OR$^7$, C(=O)R$^7$, C(=NH)NR$^8$R$^9$, C(=O)NR$^8$R$^9$, aryl, or heteroaryl;

$R^4$ is hydrogen, lower alkyl, haloalkyl, cycloalkyl, or aryl;

$R^5$ is lower alkyl, alkynyl, haloalkyl, cycloalkyl, or aryl;

$R^6$ is hydrogen, lower alkyl, or C(=O)R$^7$;

$R^7$ is lower alkyl, branched or unbranched, or aryl, either optionally substituted with one or more of OR$^8$, NR$^8$R$^9$, or SR$^8$;

$R^8$ and $R^9$, same or different, are selected from the group consisting of hydrogen, lower alkyl, cycloalkyl, aryl, heteroaryl, and aralkyl, or $R^8$ and $R^9$ together form a 4-membered to 7-membered ring;

$R^{10}$ is hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, or SO$_2$R$^{11}$; and $R^{11}$ is alkyl, cycloalkyl, trifluoromethyl, aryl, aralkyl, or NR$^8$R$^9$.

The present invention also is directed to pharmaceutical compositions containing one or more of the compounds of structural formula (II), to use of the compounds and compositions containing the compounds in the treatment of a disease or disorder, and to methods of preparing compounds and intermediates involved in the synthesis of the compounds of structural formula (II).

DETAILED DESCRIPTION OF THE PREFERRED EMBODIMENTS

The present invention is directed to compounds having the structural formula (II):

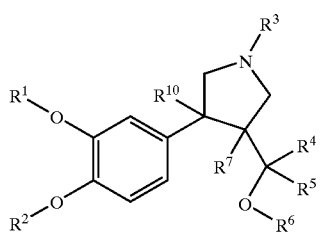

(II)

wherein $R^1$ is lower alkyl, bridged alkyl (e.g., norbornyl), aralkyl (e.g., indanyl), cycloalkyl, a 5- or 6-membered saturated heterocycle (e.g., 3-tetrahydrofuryl), $C_{13}$ alkylenecycloalkyl (e.g., cyclopentylmethyl), aryl- or heteroaryl-substituted propargyl (i.e., —CH$_2$C≡C—C$_6$H$_5$), aryl- or heteroaryl-substituted allyl (e.g., —CH$_2$CH=CH—C$_6$H$_5$), or halocycloalkyl (e.g., fluorocyclopentyl);

$R^2$ is hydrogen, methyl, or halo-substituted methyl, e.g., CHF$_2$;

$R^3$ is C(=O)OR$^7$, C(=O)R$^7$, C(=NH)NR$^8$R$^9$, C(=O)NR$^8$R$^9$, aryl, or heteroaryl;

$R^4$ is hydrogen, lower alkyl, haloalkyl, cycloalkyl, or aryl;

$R^5$ is lower alkyl, alkynyl, haloalkyl, cycloalkyl, or aryl;

$R^6$ is hydrogen, lower alkyl, or C(=O)R$^7$;

$R^7$ is lower alkyl, branched or unbranched, or aryl, either optionally substituted with one or more of OR$^8$, NR$^8$R$^9$, or SR$^8$; and $R^8$ and $R^9$, same or different, are selected from the group consisting of hydrogen, lower alkyl, cycloalkyl, aryl, heteroaryl, and aralkyl, or $R^8$ and $R^9$ together form a 4-membered to 7-membered ring;

$R^{10}$ is hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, or SO$_2$R$^{11}$; and $R^{11}$ is alkyl, cycloalkyl, trifluoromethyl, aryl, aralkyl, or NR$^8$R$^9$.

As used herein, the term "alkyl," alone or in combination, is defined to include straight chain and branched chain saturated hydrocarbon groups containing one to 16 carbon atoms. The term "lower alkyl" is defined herein as an alkyl group having one through six carbon atoms ($C_1$-$C_6$). Examples of lower alkyl groups include, but are not limited to, methyl, ethyl, n-propyl, isopropyl, isobutyl, n-butyl, neopentyl, n-hexyl, and the like. The term "alkynyl" refers to an unsaturated alkyl group that contains a carbon-carbon triple bond.

The term "bridged alkyl", is defined herein as a $C_6$-$C_{16}$ bicyclic or polycyclic hydrocarbon group, for example, norboryl, adamantyl, bicyclo [2.2.2]-octyl, bicyclo[2.2.1] heptyl, bicyclo[3.2.1]octyl, or decahydronaphthyl.

The term "cycloalkyl" is defined herein to include cyclic $C_3$-$C_7$ hydrocarbon groups. Examples of cycloalkyl groups include, but are not limited to, cyclopropyl, cyclobutyl, cyclohexyl, and cyclopentyl.

The term "alkylene" refers to an alkyl group having a substituent. For example, the term "$C_{1-3}$ alkylenecycloalkyl" refers to an alkyl group containing one to three carbon atoms, and substituted with a cycloalkyl group.

The term "haloalkyl" is defined herein as an alkyl group substituted with one or more halo substituents, either fluro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "aralkyl" is defined herein as a previously defined alkyl group, wherein one of the hydrogen atoms is replaced by an aryl group as defined herein, for example, a phenyl group optionally having one or more substituents, for example, halo, alkyl, alkoxy, and the like. An example of an aralkyl group is a benzyl group.

The term "heteroaralkyl" is defined similarly as the term "aralkyl," however, the hydrogen is replaced by a heteroaryl group as previously defined.

The term "heterocycle" is defined as a 5- or 6-membered nonaromatic ring having one or more heteroatoms selected from oxygen, nitrogen, and sulfur present in the ring. Nonlimiting examples include tetrahydrofuran, piperidine, piperazine, sulfolane, morpholine, tetrahydropyran, dioxane, and the like.

The term "halogen" or "halo" is defined herein to include fluorine, chlorine, bromine, and iodine.

The term "alkoxy" is defined as —OR, wherein R is alkyl.

The term "alkoxyalkyl" is defined as an alkoxy group appended to an alkyl group.

The term "hydroxyl" is defined as —OH.

The term "hydroxyalkyl" is defined as a hydroxy group appended to an alkyl group.

The term "amino" is defined as $-NH_2$.

The term "alkylamino" is defined as $-NR_2$ wherein at least one R is alkyl and the second R is alkyl or hydrogen.

The term "acylamino" is defined as RC(=O)NH, wherein R is alkyl or aryl.

The term "nitro" is defined as $-NO_2$.

The term "alkylthio" is defined as —SR, where R is alkyl.

The term "alkylsulfinyl" is defined as $R-S(O)_2$, where R is alkyl.

The term "alkylsulfonyl," is defined as $R-S(O_3)$, where R is alkyl.

In preferred embodiments, $R^5$ and $R^7$ are methyl, $R^2$ is methyl or difluoromethyl, $R^4$ is selected from the group consisting of hydrogen, methyl, trifluoromethyl, cyclopropyl, acetyl, ethynyl, benzyl, and phenyl. $R^6$ is selected from the group consisting of hydrogen, acetyl, and benzoyl. $R^1$ is selected from the group consisting of

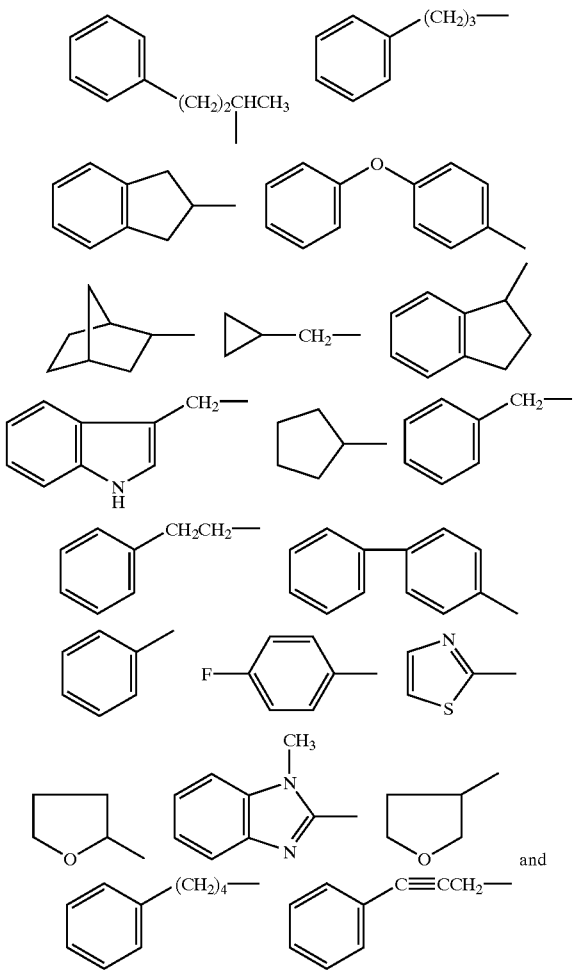

$R^3$ is selected from the group consisting of

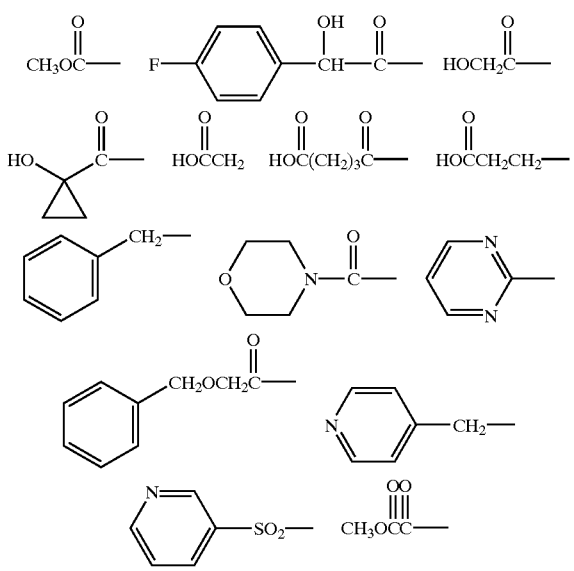

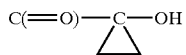

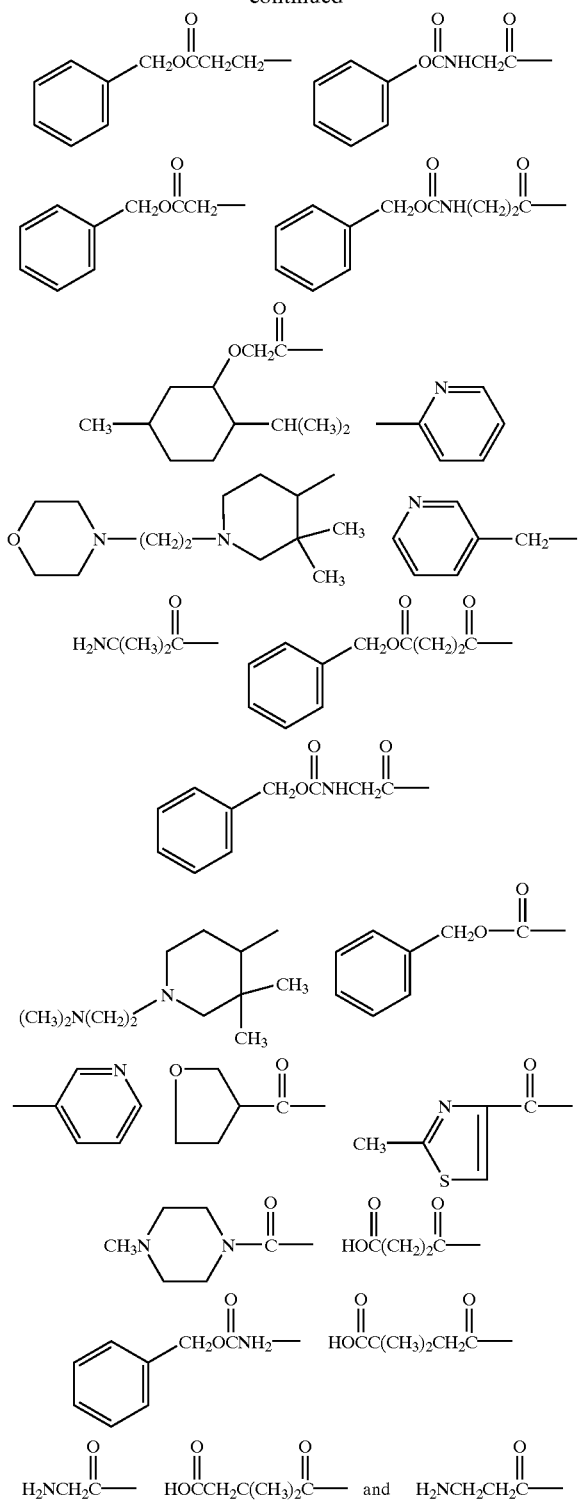

In most preferred embodiments, R¹ is selected from the group consisting of cyclopentyl, tetrahydrofuryl, indanyl, norbornyl, phenethyl, and phenylbutyl; R² is selected from the group consisting of methyl and difluoromethyl; R³ is selected from the group consisting of $CO_2CH_3$, $C(=O)$ $CH_2OH$, $C(=O)CH(CH_3)OH$, $C(=O)C(CH_3)_2OH$, and $R^4$ is hydrogen; $R^5$ is methyl; $R^6$ is hydrogen; and $R^8$ and $R^9$ are selected from the group consisting of hydrogen and lower alkyl, or form a 5-membered or 6-membered ring.

The present invention includes all possible stereoisomers and geometric isomers of compounds of structural formula (II), and includes not only racemic compounds but also the optically active isomers as well. When a compound of structural formula (II) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883–888 (1997). Resolution of the final product, an intermediate, or a starting material can be achieved by any suitable method known in the art. Additionally, in situations where tautomers of the compounds of structural formula (II) are possible, the present invention is intended to include all tautomeric forms of the compounds. As demonstrated hereafter, specific stereoisomers exhibit an exceptional ability to inhibit PDE4 without manifesting the adverse CNS side effects typically associated with PDE4 inhibitors.

In particular, it is generally accepted that biological systems can exhibit very sensitive activities with respect to the absolute stereochemical nature of compounds. (See, E. J. Ariens, *Medicinal Research Reviews*, 6:451–466 (1986); E. J. Ariens, *Medicinal Research Reviews*, 7:367–387 (1987); K. W. Fowler, Handbook of Stereoisomers: Therapeutic Drugs, CRC Press, edited by Donald P. Smith, pp. 35–63 (1989); and S. C. Stinson, *Chemical and Engineering News*, 75:38–70 (1997).)

For example, rolipram is a stereospecific PDE4 inhibitor that contains one chiral center. The (−)-enantiomer of rolipram has a higher pharmacological potency than the (+)-enantiomer, which could be related to its potential antidepressant action. Schultz et al., *Naunyn-Schmiedeberg's Arch Pharmacol*, 333:23–30 (1986). Furthermore, the metabolism of rolipram appears stereospecific with the (+)-enantiomer exhibiting a faster clearance rate than the (−)-enantiomer. Krause et al., *Xenobiotica*, 18:561–571 (1988). Finally, a recent observation indicated that the (−)-enantiomer of rolipram (R-rolipram) is about ten-fold more emetic than the (+) -enantiomer (S-rolipram). A. Robichaud et al., *Neuropharmacology*, 38:289–297 (1999). This observation is not easily reconciled with differences in test animal disposition to rolipram isomers and the ability of rolipram to inhibit the PDE4 enzyme. The compounds of the present invention can have three chiral centers. As shown below, compounds of a specific stereochemical orientation exhibit similar PDE4 inhibitory activity and pharmacological activity, but altered CNS toxicity and emetic potential.

Accordingly, preferred compounds of the present invention have the structural formula (III):

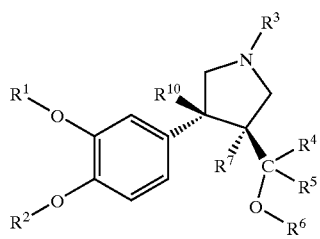

(III)

The compounds of structural formula (III) are potent and selective PDE4 inhibitors, and do not manifest the adverse CNS effects and emetic potential demonstrated by stereoisomers of a compound of structural formula (III).

The compounds of the present invention can be therapeutically administered as the neat chemical, but it is preferable to administer compounds of structural formula (II) as a pharmaceutical composition or formulation. Accordingly, the present invention further provides for pharmaceutical formulations comprising a compound of structural formula (II), together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

The present PDE4 inhibitors are useful in the treatment of a variety of allergic, autoimmune, and inflammatory diseases.

In particular, inflammation is a localized, protective response elicited by injury or destruction of tissues, which serves to destroy, dilute or wall off (i.e., sequester) both the injurious agent and the injured tissue. The term "inflammatory disease," as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

The present invention also provides a method of modulating cAMP levels in a mammal, as well as a method of treating diseases characterized by elevated cytokine levels.

The term "cytokine," as used herein, means any secreted polypeptide that affects the functions of other cells, and that modulates interactions between cells in the immune or inflammatory response. Cytokines include, but are not limited to monokines, lymphokines, and chemokines regardless of which cells produce them. For instance, a monokine is generally referred to as being produced and secreted by a monocyte, however, many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines include, but are not limited to, interleukin-1 (IL-1), interleukin-6 (IL-6), Tumor Necrosis Factor alpha (TNFα), and Tumor Necrosis Factor beta (TNFβ).

The present invention further provides a method of reducing TNF levels in a mammal, which comprises administering an effective amount of a compound of structural formula (II) to the mammal. The term "reducing TNF levels," as used herein, means either:

a) decreasing excessive in vivo TNF levels in a mammal to normal levels or below normal levels by inhibition of the in vivo release of TNF by all cells, including but not limited to monocytes or macrophages; or b) inducing a down-regulation, at the translational or transcription level, of excessive in vivo TNF levels in a mammal to normal levels or below normal levels; or c) inducing a down-regulation, by inhibition of the direct synthesis of TNF as a postranslational event.

Moreover, the compounds of the present invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

The compounds of the present invention also are useful in causing airway smooth muscle relaxation, bronchodilation, and prevention of bronchoconstriction.

The compounds of the present invention, therefore, are useful in treating such diseases as arthritic diseases (such as rheumatoid arthritis), osteoarthritis, gouty arthritis, spondylitis, thyroid-associated ophthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Mentz et al., *Blood* 88, pp. 2172–2182 (1996)), and inflammatory dermatoses, such as atopic dermatitis, psoriasis, or urticaria.

Other examples of such diseases or related conditions include cardiomyopathies, such as congestive heart failure, pyrexia, cachexia, cachexia secondary to infection or malignancy, cachexia secondary to acquired immune deficiency syndrome (AIDS), ARC (AIDS-related complex), cerebral malaria, osteoporosis and bone resorption diseases, and fever and myalgias due to infection. In addition, the compounds of the present invention are useful in the treatment of diabetes insipidus and central nervous system disorders, such as depression and multi-infarct dementia.

Compounds of the present invention also have utility outside of that typically known as therapeutic. For example, the present compounds can function as organ transplant preservatives (see Pinsky et al., *J. Clin. Invest.*, 92, pp. 2994–3002 (1993)) as well.

Selective PDE4 inhibitors also can be useful in the treatment of diabetes insipidus (*Kidney Int.*, 37, p. 362, (1990); *Kidney Int.*, 35, p. 494, (1989)) and central nervous system disorders, such as depression and multi-infarct dementia (see Eckman et al., *Curr. Ther. Res.*, 43, p. 291, (1988); Nicholson, *Psychopharmacology*, 101, p. 147, (1990)). Selective PDE4 inhibitors also can be useful in applications that modulate bronchodilatory activity via direct action on bronchial smooth muscle cells for the treatment of asthma.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 mg/kg to about 100 mg/kg per day. The desired dose can be conveniently administered in a single dose, or as multiple doses administered at appropriate intervals, for example as two, three, four or more subdoses per day.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For buccal administration, the composition can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline, cellulose, maize-starch, calcium phosphate or sorbitol), lubricants (for example, magnesium, stearate, stearic acid, talc, polyethylene glycol or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, methyl cellulose, glucose/sugar syrup, gelatin, hydroxyethylcellulose, hydroxypropylmethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

Specific, nonlimiting examples of compounds of structural formula (II) are provided below, the synthesis of which were performed in accordance with the procedures set forth below.

Generally, compounds of structural formula (II) can be prepared according to the following synthetic schemes. In each scheme described below, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of structural formula (II) not specifically set forth herein can be accomplished by methods analogous to the schemes set forth below.

Unless otherwise noted, all starting materials were obtained from commercial suppliers and used without further purification. All reactions and chromatography fractions were analyzed by thin-layer chromatography on 250-mm silica gel plates, visualized with UV (ultraviolet) light $I_2$ (iodine) stain. Products and intermediates were purified by flash chromatography, or reverse-phase HPLC.

The compounds of general structural formula (II) can be prepared, for example, by first reacting a disubstituted benzaldehyde (1) with 2-butanone, then following the reaction scheme illustrated below. Other synthetic routes also are known and available to persons skilled in the art. For example, see Feldman et al. U.S. Pat. No. 5,665,754, incorporated herein by reference, for various individual reactions, and the synthetic methods disclosed in the Intermediates and Examples presented hereafter.

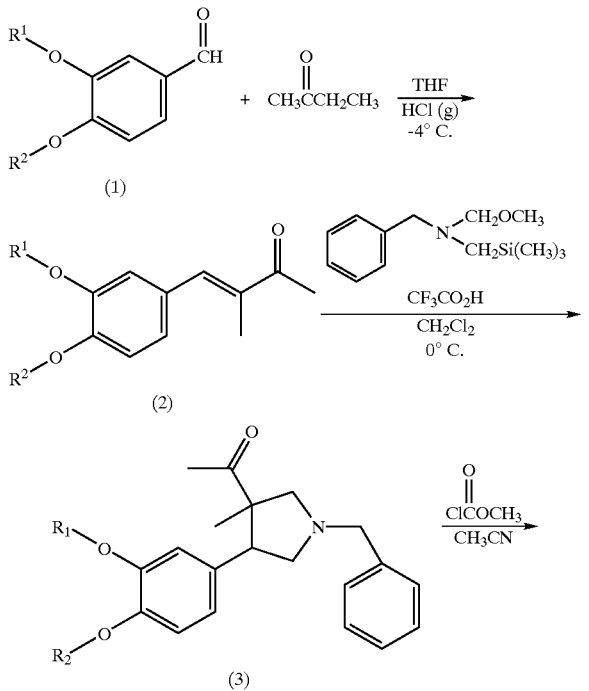

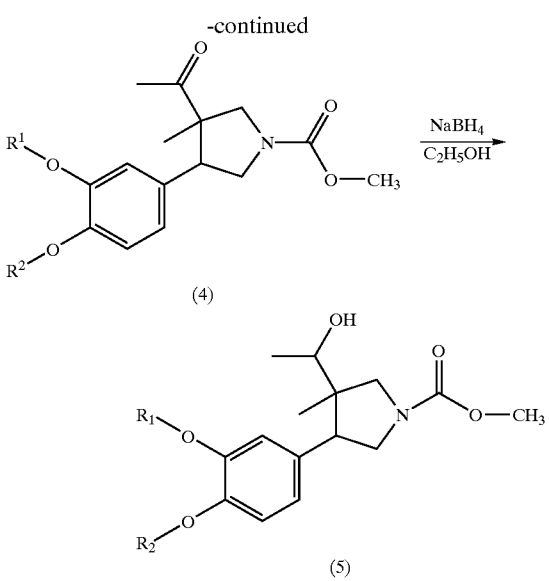

The above reaction scheme provides a compound (5) of structural formula (II), wherein $R^1$ and $R^2$ are determined by the starting benzaldehyde, $R^3$ is $C(=O)OCH_3$, $R^4$ is hydrogen, $R^5$ is methyl, $R^6$ is hydrogen, and $R^7$ is methyl, and $R^{10}$ is hydrogen. Proper selection of starting materials, or performing conversion reactions on compound (5), provide compounds of general structural formula (II) having other recited $R^1$ through $R^7$ and $R^{10}$ substituents.

The following illustrates the synthesis of various intermediates and compounds of structural formula (II). The following examples are provided for illustration and should not be construed as limiting.

General Synthesis for Cyclopentyl Series

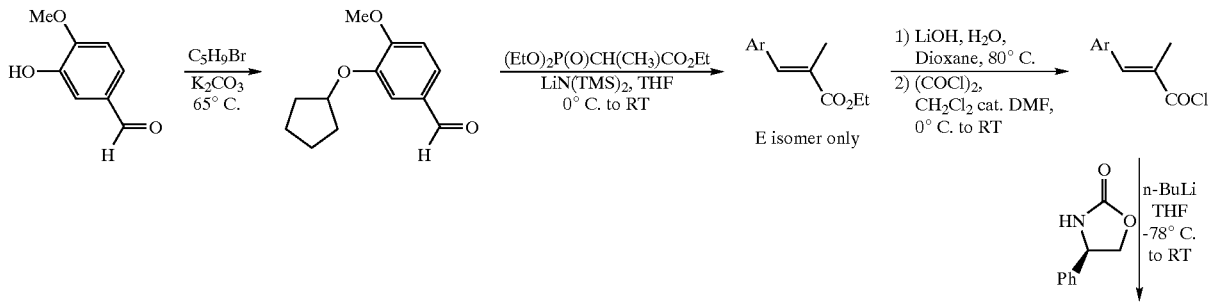

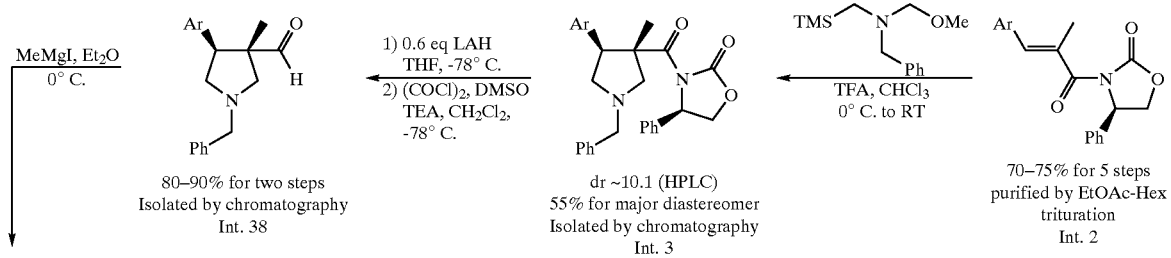

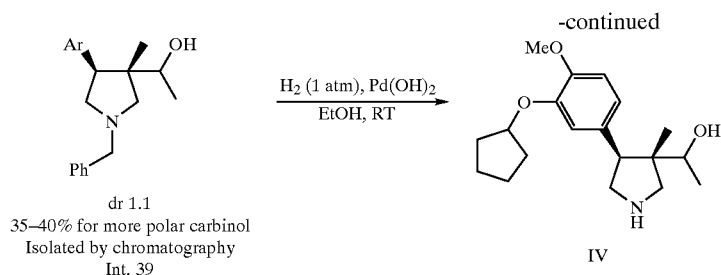
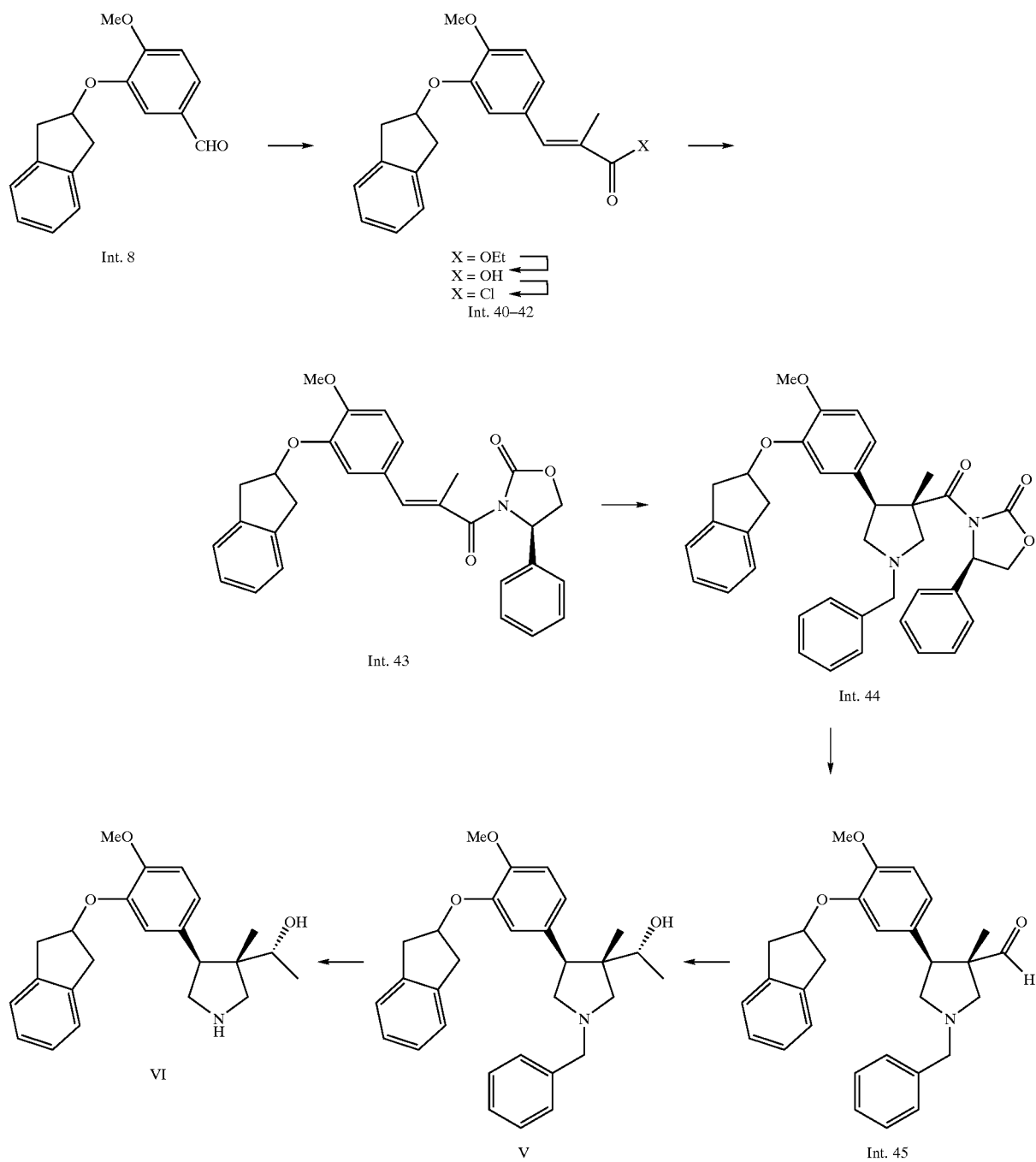
General Synthesis for Indanyl Series

-continued
General Synthesis of Varying R¹ Substituents

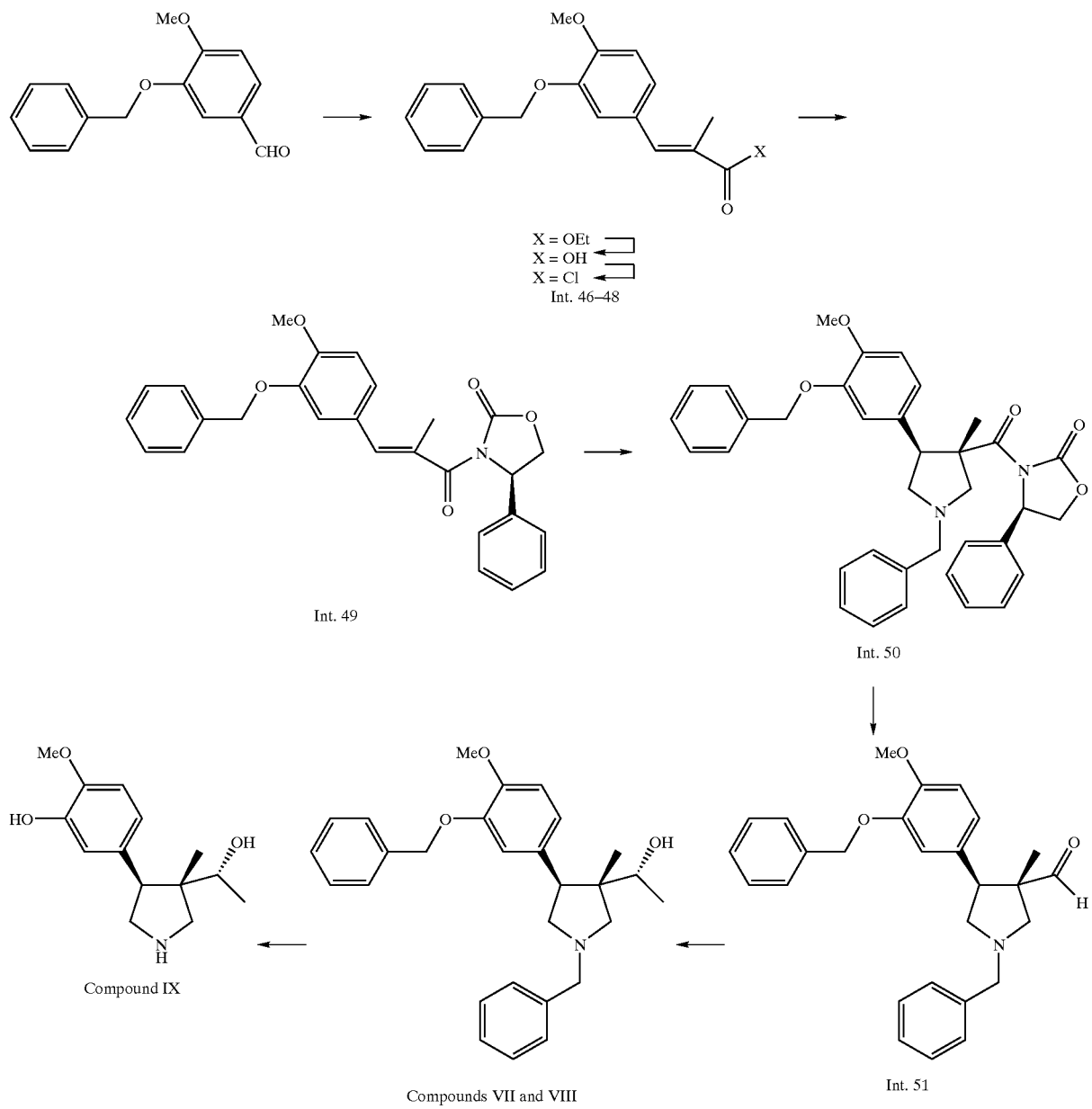

Intermediate 1

Preparation of (E)-3-(3-Cyclopentoxy-4-methoxy-phenyl)-2-methyl-acrylic Acid

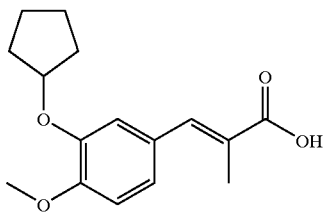

First, (E)-3-(3-cyclopentyloxy-4-methoxy-phenyl)-2-methyl-acrylic acid ethyl ester was prepared as follows:

To a cooled (0° C.), stirred solution of triethylphosphonopropionate (50.6 mL; 236 mmol; 1.05 eq.) in dry tetrahydrofuran (500 mL) was added a solution of lithium hexamethyldisilylamide in tetrahydrofuran (247 mL of 1.0 M; 1.1 eq.) via syringe under nitrogen atmosphere. The resulting yellow solution was allowed to stir at 0° C. for 1.5 hours, then a solution of 3-cyclopentoxy-4-methoxy-benzaldehyde (49.4 g; 225 mmol) in dry tetrahydrofuran (150 mL) was added dropwise via addition funnel over 0.5 hour. The resulting orange solution was allowed to stir at 0° C. for 2 hours, then was warmed to room temperature and stirred overnight. The reaction then was quenched with the addition of water (400 mL) and extracted with ether (2×300 mL). The combined organic layers were washed with 1N aqueous hydrochloric acid (250 mL), saturated aqueous bicarbonate (250 mL), and brine (250 mL), then dried over MGSO₄, filtered and concentrated in vacuo to provide the unsaturated ester as a brown liquid (68.4 g; 100%).

$^1$H NMR (CDCl$_3$, 400 MHz) δ7.64 (s, 1H), 7.01–6.96 (c, 2H), 6.87 (m, 1H), 4.77 (m, 1H), 4.26 (q, 2H). LRMS (Electrospray, positive): Da/e 305.3 (m+1).

A suspension of (E)-3-(3-cyclopentoxy-4-methoxyphenyl)-2-methyl-acrylic acid ethyl ester (30 g, 98.6 mmol) and LiOH.H$_2$O (lithium hydroxide hydrate) (5.0 g, 119.2 mmol, 1.2 equiv.) in methanol-water (4:1, 100 mL) was stirred at room temperature for 24 hours. Methanol was removed under reduced pressure and the resulting residue was dissolved in water (100 mL), washed with three 100 mL portions of ethyl acetate, neutralized with 1.0 N HCl (hydrochloric acid) (100 mL), and extracted with two 150 mL portions of ethyl acetate. The extract was washed with brine, dried over anhydrous Na$_2$SO$_4$ (sodium sulfate), and concentrated under reduced pressure to afford the desired product as a light yellow powder (18.2 g, 66% yield). $^1$H NMR (300 MHz, CDCl$_3$) δ(ppm): 12.4 (br. s, 1H, COOH), 7.56 (s, 1H, olefinic), 7.04 (m, 3H, aromatic), 4.81 (m, 1H), 3.78 (s, 3H, OCH$_3$), 2.06 (s, 3H, CH$_3$), 1.91–1.57 (m, 8H, cyclopentyl).

Intermediate 1 was prepared in an alternative method as follows:

To a stirred solution of the ethyl ester (68.4 g; 225 mmol) in dioxane (400 mL) was added a solution of lithium hydroxide monohydrate (14.0 g; 332 mmol; 1.5 eq.) in water (200 mL) at room temperature and under a nitrogen atmosphere. A slight exotherm was observed. The resulting cloudy yellow solution was heated to 80° C. (oil bath) for 1.5 hours. After heating for 0.5 hour, the reaction became clear, but required an additional 1.5 hours to complete the reaction, as evaluated by TLC. The resulting solution was allowed to cool to room temperature, diluted with ether (500 mL), then was washed with 1 M aqueous phosphoric acid (H$_3$PO$_4$). This aqueous layer then was extracted with ethyl acetate (2×200 mL) and the combined ethyl acetate and ether layers were washed with brine (250 mL), dried over MGSO$_4$, filtered and concentrated in vacuo to provide Intermediate 1 as an orange solid (55 g; 88%).

$^1$H NMR (CDCl$_3$, 400 MHz): δ7.76 (s, 1H), 7.06–7.00 (c, 2H), 6.89 (m, 1H), 4.78 (m, 1H), 3.88 (s, 3H), 2.17 (s, 3H), 1.97–1.83 (c, 6H), 1.64–1.61 (c, 2H). LRMS (Electrospray, negative): Da/e 275.3 (M−1).

Intermediate 2

Preparation of 3-[(2E)-3-(3-cyclopentyloxy-4-methoxyphenyl)-2-methylprop-2-enoyl]-(4R)-4-phenyl-1,3-oxazolidin-2-one

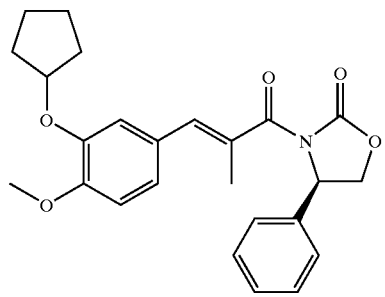

To a cooled (0° C.), stirred slurry of Intermediate 1 (55 g; 199 mmol) in anhydrous dichloromethane (400 mL) was added a solution of oxalyl chloride in dichloromethane (109 mL of 2.0 M; 218 mmol; 1.1 eq.) via a syringe under a calcium chloride-dried atmosphere over 10 minutes. Vigorous bubbling was observed. The resulting dark solution was allowed to stir at 0° C. for 15 minutes, then a catalytic amount of dimethylformamide was added via syringe (0.3 mL). The resulting solution was allowed to continue stirring at 0° C. for 0.5 hour as the bubbling subsided, and then was allowed to warm to room temperature and stirred overnight (17 hours). The reaction was diluted with ethyl acetate (500 mL) and was carefully quenched with water (250 mL). After vigorously stirring this mixture for 1 hour, the layers were separated, and the organic layer was washed with additional water (400 mL) and brine (400 mL), then dried over MgSO$_4$, filtered and concentrated in vacuo to provide an acid chloride as a brown solid (57.5 g; 98%).

$^1$H NMR (CDCl$_3$, 400 MHz): δ7.98 (s, 1H), 7.11–7.02 (c, 2H), 6.92 (m, 1H), 4.79 (m, 1H), 3.90 (s, 3H) 2.22 (s, 3H), 2.01–1.82 (c, 6H), 1.68–1.62 (c, 2H)

To a cooled (−78° C.), mechanically stirred solution of R-phenyl oxazolidinone (10.0 g; 61.3 mmol) in dry tetrahydrofuran (400 mL) was added a solution of n-butyllithium in hexanes (27 mL of 2.5 M; 1.1 eq.) via syringe under nitrogen atmosphere. The resulting solution was allowed to stir at −78° C. for 0.8 hour, then a solution of the acid chloride (19.9 g; 67.4 mmol; 1.1 eq.) in tetrahydrofuran (100 mL) was added via cannulae. After stirring at −78° C. for 15 minutes, the reaction mixture was allowed to slowly warm to 0° C. over 40 minutes, during which time the reaction became a thick slurry. After stirring at 0° C. for 2.5 hours, the reaction was quenched with saturated, aqueous ammonium chloride (300 mL), and the bulk of the tetrahydrofuran was removed at reduced pressure. The residue then was extracted with chloroform (3×700 mL) and the combined organic layers were washed with water (300 mL) and brine (300 mL), then dried over MgSO$_4$, filtered and concentrated in vacuo to provide about 33 g of a light orange solid. This material was suspended in 10% ethyl acetate in hexane (1.2 L), and vigorously stirred overnight. The resulting fine powdery solids were collected on a Buchner funnel with suction and then dried in vacuo to provide Intermediate 2 as a tan powder (21.8 g; 88%).

$^1$H NMR (CDCl$_3$, 400 MHz): δ7.41–7.37 (c, 5H), 7.06 (s, 1H), 7.01–6.97 (c, 2H), 6.86 (m, 1H), 5.54 (t, 1H), 4.77–4.73 (c, 2H), 4.29 (t, 1H), 3.87 (s, 3H), 2.17 (s, 3H), 1.97–1.82 (c, 6H), 1.62–1.56 (c, 2H).

Similarly, the enantiomer of Intermediate 2 can be prepared using S-(−)-4-phenyl oxazolidinone.

Intermediate 3

Preparation of (4R)-3-{[(3S,4S)-4-(3-cyclopentyloxy-4-methoxyphenyl)-3-methyl-1-benzylpyrrolidin-3-yl]carbonyl)-4-phenyl-1,3-oxazolidin-2-one

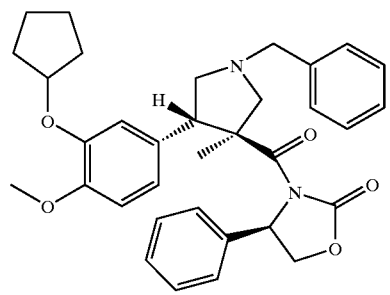

To a cooled (−4° C.), stirred slurry of Intermediate 2 (9.30 g; 22.8 mmol) and N-(methoxymethyl)-N-(trimethylsilylmethyl)benzylamine (11.7 mL; 45.6 mmol; 2 eq.) in chloroform (65 mL) was added a solution of trifluoroacetic acid in chloroform (4.6 mL of 1.0 M; 4.6 mmol; 0.2 eq.) via syringe under nitrogen atmosphere. The resulting slurry was allowed to stir at about 0° C. for 4 hours, and then at about 15° C. overnight (water bath). The resulting cloudy solution then was recooled to −40° C. and treated with additional N-(methoxymethyl)-N-(trimethylsilylmethyl)benzylamine (5.9 mL; 22.8 mmol; 1 eq.) via syringe, and allowed to stir for 5 hours during which time the reaction became homogenous. TLC (5% Et$_2$O in CH$_2$Cl$_2$) show the reaction was complete. The bulk of the chloroform was removed at reduced pressure and the residue was diluted with ethyl acetate (250 mL), then washed successively with 1 N aqueous hydrochloric acid (2×50 mL), 1 N aqueous sodium hydroxide (50 mL), and brine (50 mL). The organic layer then was dried over MgSO$_4$, filtered, and concentrated in vacuo to give an orange semisolid (13.9 g). Purification via flash chromatography on silica gel (2% ether in dichloromethane) provided the major diastereomer pyrrolidine as a white foam (8.25 g; 65%).

Diastereomeric selectivity about 10:1 (HPLC).

$^1$H NMR (CDCl$_3$ 400 MHz): δ7.42–7.21 (c, 10H), 6.95 (s, 1H), 6.81 (s, 2H), 5.55 (dd, 1H), 4.74 (t, 1H), 4.68 (m, 1H), 4.10 (dd, 1H), 3.93 (t, 1H), 3.70 (d, 1H), 3.68 (s, 3H), 3.56 (d, 1H), 3.42 (d, 1H), 2.72 (m, 2H), 2.64 (d, 1H), 2.48 (m, 1H), 1.85–1.78 (c, 2H), 1.75–1.61 (c, 4H), 1.57–1.53 (c, 2H), 0.96 (s, 3H). LRMS (Electrospray, positive): Da/e 555.2 (m+1).

Intermediate 4

Preparation of (3S,4S)-4-(3-cyclopentyloxy-4-methoxyphenyl)-3-methyl-1-benzylpyrrolidine-3-carboxylic Acid

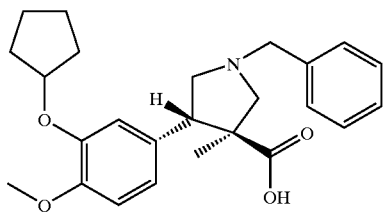

A suspension of lithium peroxide (0.5 g, 10.8 mmol) in water-THF (1:1, 6 mL) was added to a solution of Intermediate 3 (3.0 g, 5.4 mmol) in water-THF (3:1, 30 mL) at 0° C. under N$_2$. The suspension was solubilized immediately. After 1 hour of stirring at 0° C., an aqueous Na$_2$SO$_3$ (sodium sulfite) solution (1.5 N, 12 mL) was added to quench any excess peroxide, and THF removed under reduced pressure. The basic residue was extracted with three 30 mL portions of CH$_2$Cl$_2$. The aqueous phase was acidified to pH 1 with aqueous 1.0 N HCl solution, then extracted with three 30 mL portions of ethyl ether. The ether extracts were dried (Na$_2$SO$_4$), concentrated under reduced pressure, and the product was used without further purification. $^1$H NMR (300 MHz, CDCl$_3$) δ(ppm): 10.73 (br, s, 1H, COOH), 7.69 (br, s, 2H, aromatic), 7.38–7.36 (m, 3H, aromatic), 6.78 (s, 1H, aromatic), 4.71 (br, s, 1H), 4.51–4.48 (m, 2H), 4.24–4.11 (br, s, 2H), 4.08–3.88 (br, s, 1H), 3.76 (s, 3H, OCH$_3$), 3.54 (br, s, 1H), 3.1 (br, s, 1H) 1.83–1.52 (m, 8H, cyclopentyl), 1.05 (br, s, 3H, CH$_3$).

Intermediate 5

Preparation of [3S,4S]-4-(3-cyclopentyloxy-4-methoxyphenyl)-3-methyl-1-benzylpyrrolidin-3-yl]-N-methoxy-N-methyl-carboxamide

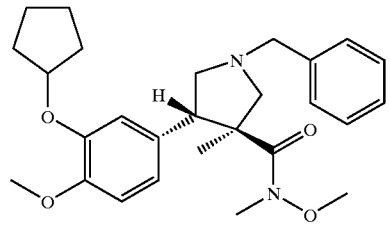

To a solution of crude Intermediate 4 (2.1 g, 4.98 mmol) in CH$_2$Cl$_2$ (30 mL) was added 1,1'-carbonyldiimidazole (0.89 g, 5.47 mmol) under N$_2$. The resulting solution was stirred for 5 minutes and N,O-dimethylhydroxylamine hydrochloride (0.73 g, 7.47 mmol) was added. The suspension was stirred at room temperature for 20 hours, then triethylamine (0.5 g) was added, and the mixture was stirred a further 30 minutes. The solution was diluted with CH$_2$Cl$_2$ (30 mL), then washed successively with 0.1N HCl and water, then with saturated aqueous NaHCO$_3$ solution and brine, followed by concentrating the mixture to obtain, on drying, 1.9 g of crude product. Chromatography on silica gel (7.5×36 cm Biotage KP-Sil column, eluting with a 1:1 hexanes:ethyl acetate solvent mixture) provided the product (0.9 g, 40% yield) as a white crystalline powder. $^1$H NMR (300 MHz, CDCl$_3$) δ (ppm): 7.4–7.3 (m, 5H, aromatic), 7.06 (d, 1H, J=1.7 Hz, aromatic), 6.89 (dd, 1H, J=8.3 Hz, aromatic), 6.73 (d, 1H, J=8.3 Hz, aromatic), 4.77–4.75(m, 1H), 4.16–4.06(m, 1H), 3.81 (s, 3H, OCH$_3$), 3.81–3.71 (m, 2H), 3.60 (s, 3H, OCH$_3$), 3.21 (s, 3H, NCH$_3$), 2.96 (d, 1H, J=9.6 Hz,), 2.91 (m, 1H), 2.78 (d, 1H, J=9.6 Hz,), 2.77 (m, 1H), 2.04 (s, 3H, CH$_3$), 1.92–1.59 (m, 8H, cyclopentyl), 0.94 (s, 3H, CH$_3$).

Intermediate 6

Preparation of 1-[(3S,4S)-4-(3-cyclopentyloxy-4-methoxyphenyl)-3-methyl-benzylpyrrolidin-3-yl]ethan-1-one

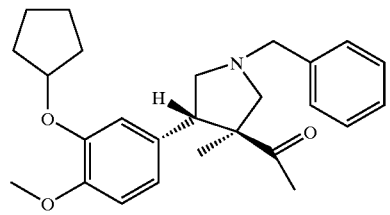

A solution of Intermediate 5 (0.17 g, 0.43 mmol) in THF (8 mL) was cooled to −78° C. and treated with methyllithium (1.5 M in THF, 0.315 mL, 0.47 mmol) under N$_2$. The solution was stirred for 40 minutes at −78° C. and quenched with a cold saturated aqueous NH$_4$Cl solution (8 mL). A mixture of hexanes/CH$_2$Cl$_2$ (3:1, 8 mL) was added with vigorous stirring. After a further dilution with more hexanes/CH$_2$Cl$_2$ (3:1, 10 mL), brine (10 mL) was added, and the two layers were separated. The aqueous layer was washed with CH$_2$Cl$_2$ (8 mL) and the combined organic extracts washed with brine, then dried (Na$_2$SO$_4$), filtered, and concentrated under reduced pressure into an oil product (154 mg, 89% yield). $^1$H NMR (300 MHz, CDCl$_3$) δ (ppm): 7.39–7.24 (m, 5H, aromatic), 6.82–6.70 (m, 3H, aromatic), 4.74 (br. s, 1H), 3.81 (s, 3H, OCH₃), 3.78–3.58 (m, 3H), 3.14 (d, 1H, J=9.7 Hz ), 3.05 (m, 1H), 2.84 (m, 1H), 2.40 (d, 1H, J=9.7 Hz,), 2.23 (s, 3H, CH₃), 1.92–1.59 (m, 8H, cyclopentyl), 0.83 (s, 3H, CH₃)

Intermediate 7

Preparation of Methyl(3S,4S)-3-Acetyl-4-(3-cyclopentyloxy-4-methoxyphenyl)-3-methyl-pyrrolidinecarboxylate

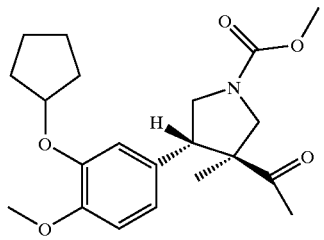

To a stirred solution of Intermediate 6 (0.154 g, 0.38 mmol) in anhydrous acetonitrile (10 mL) was added methyl chloroformate (0.146 mL, 1.89 mmol). The solution was heated to 80° C. and refluxed for 3 hours. The solution then was cooled to room temperature, and concentrated under reduced pressure. Purification by reversed-phase HPLC provided the desired product as an oil (93 mg, 65% yield). $^1$H NMR (300 MHz, CDCl₃) δ (ppm): 6.8 (d, 1H, J=8.0 Hz, aromatic), 6.66 (d, 1H, J=8.0 Hz, aromatic), 6.66 (s, 1H, aromatic), 4.73(s, 1H), 3.95–3.64(m, 4H), 3.83 (s, 3H, OCH₃), 3.74 (s, 3H, OCH₃), 3.37 and 3.27(s, 3H, CH₃), 2.17 and 2.14 (s, 3H, CH₃), 1.92–1.59 (m, 8H, cyclopentyl), 1.03 and 1.02 (s, 3H, CH₃).

Intermediate 8

Preparation of 3-(Indan-2-yloxy)-4-methoxy-benzaldehyde

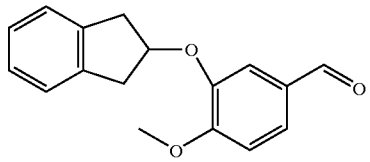

A solution of 3-hydroxy-4-methoxy-benzaldehyde (15.2 g, 100 mmol, 1 eq), 2-indanol (12.1 g, 90 mmol, 0.9 eq), and triphenylphosphine (26.2 g, 100 mmol, 1 eq) in dry THF (300 mL) was treated dropwise with diisopropylazodicarboxylate (19.6 mL, 100 mmol, 1 eq). The reaction mixture was stirred at reflux for 16 hours, then cooled and diluted with diethyl ether (500 mL). The solution was washed with water (2×150 mL), 1 M NaOH (4×125 mL), and saturated NaCl (sodium chloride) (2×100 mL), dried with CH₂Cl₂, then concentrated to provide a syrup, which solidified upon standing. The solid was suspended in diethyl ether (350 mL) and stirred overnight to break up all chunks. The solid was collected by vacuum filtration and recrystallized from ethanol/water (21.4 g). The ethereal filtrate was concentrated and purified by flash chromatography (silica gel, 7.5×36 cm Biotage KP-Sil column, eluted with 25% ethyl acetate in heptane) to yield an additional 5 g of product. $^1$H NMR (300 MHz, CDCl₃) δ9.86 (s, 1H), 7.49–7.44 (m, 2H), 7.25–7.16 (m, 4H), 6.97 (d, J=8.7 Hz, 1H), 5.29–5.22 (m, 1H), 3.89 (s, 1H), 3.45 (dd, J=16.7, 6.6 Hz, 2H), 3.24 (dd, J=16.7, 3.6 Hz, 2H). $^{13}$C NMR (75 MHz, CDCl₃) δ190.9, 155.5, 147.9, 140.4, 130.0, 126.9, 126.8, 124.7, 112.1, 111.0, 78.9, 56.1, 39.7.

Intermediate 9

Preparation of (E)-4-(3-Benzyloxy-4-methoxyphenyl)-3-methyl-but-3-en-2-one

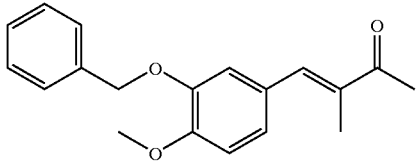

A solution of 3-benzyloxy-4-methoxy-benzaldehyde (34 g, 0.14 mol, 1 eq) and 2-butanone (50 mL, 0.56 mol, 4 eq) in dry THF (50 mL) was cooled to −4° C. Hydrogen chloride gas was passed through the well-stirred solution for several minutes, and the reaction mixture was capped and stored at −40° C. for 16 hours. The mixture was poured into a well stirred solution of ice-cold saturated NaHCO₃ (about 2 L). If necessary, the pH was adjusted to >7 with saturated NaHCO₃, and the mixture was extracted with ethyl acetate (3×300 mL). The ethyl acetate layer was washed with NaHCO₃ (2×200 mL), water (2×200 mL), and saturated NaCl (2×200 mL), dried with CH₂Cl₂, then concentrated to a syrup. The crude mixture was purified by flash chromatography (silica gel, 7.5×36 cm Biotage KP-Sil column, eluted with 25% ethyl acetate in heptane, to yield 29.2 g of solid product (70% yield). $^1$H NMR (300 MHz, CDCl₃) δ7.46–7.27 (m, 6H), 7.06–6.91 (m, 3H), 3.93 (, s, 3H), 2.41 (s, 3H), 1.92 (d, J=1.1 Hz, 3H).

The following Intermediates 10–12 were prepared following the same procedure:

Intermediate 10

(E)-4-[3-(Indan-2-yloxy)-4-methoxyphenyl]-3-methyl-but-3-en-2-one (from Intermediate 8)

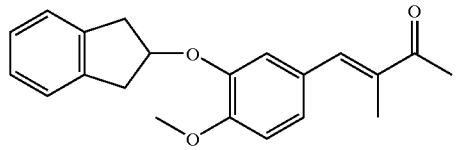

$^1$H NMR (300 MHz, CDCl₃) δ7.49–7.43 (m, 2H), 7.26–7.15 (m, 5H), 6.90 (d, J=8.2 Hz, 1H), 5.25–5.16 (M, 1H), 3.85 (s, 3H), 3.38 (dd, J=16.7, 6.5 Hz, 2H), 3.25 (dd, J=16.7, 3.8 Hz, 2H), 2.45 (S, 3H), 2.10 (d, J=1.1 Hz).

Intermediate 11

(E)-4-(3-Bromo-4-methoxyphenyl)-3-methyl-but-3-en-2-one

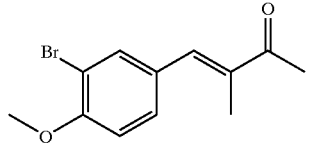

$^1$H NMR (300 MHz, CDCl₃) δ7.66 (d, J=2.0 Hz, 1H) 7.36–7.41 (m, 2H), 6.94 (d, J=8.6 Hz, 1H), 3.94 (s, 3H), 2.45 (s, 3H), 2.06 (d, J=1.1 Hz, 3H).

Intermediate 12

(E)-4-(3-Cyclopentyloxy-4-methoxyphenyl)-3-methyl-but-3-en-2-one

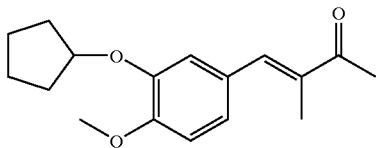

¹H NMR (300 MHz, CDCl₃) δ7.45 (br s, 1H), 7.05–6.99 (m, 2H), 6.90 (d, J=8.26 Hz, 1H), 4.81–4.75, m, 1H), 3.89 (s, 3H), 2.46 (s, 3H), 2.09 (d, J=1.1 Hz, 3H), 1.98–1.79 (m, 6H), 1.66–1.60 (m, 2H).

Intermediate 13

Preparation of 1-[(3SR, 4RS)-1-Benzyl-4-(3-benzyloxy-4-methoxyphenyl)-3-methyl-pyrrolidin-3-yl]-ethanone

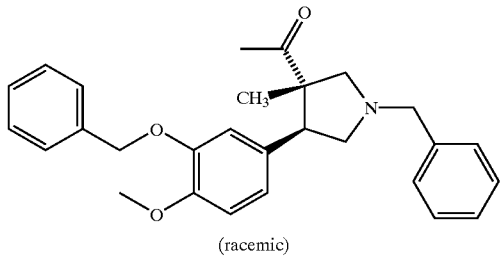

(racemic)

A solution of Intermediate 9 (15 g, 50.6 mmol, 1 eq) and N-methoxymethyl-N-benzyl-trimethysilylmethylamine (11.9 g, 50.6 mmol, 1 eq) in dichloromethane (85 mL) at 0° C. was treated dropwise with a solution of trifluoroacetic acid (1 M in dichloromethane, 5 mL, 5.1 mmol, 0.1 eq). After stirring at the same temperature for 30 minutes, the reaction mixture was stirred at room temperature for 16 hours. The solution was treated with additional N-methoxymethyl-N-benzyl-trimethysilylmethylamine (6 g, 25.3 mmol, 0.5 eq), stirred 1 hour at room temperature, and treated for a third time with N-methoxymethyl-N-benzyl-trimethysilylmethylamine (6 g, 25.3 mmol, 0.5 eq). The reaction mixture was concentrated, and the residue was dissolved in ethyl acetate (500 mL). This solution was washed with 1 N HCl (2×60 mL with 10 mL saturation NaCl added), water (250 mL), 1 M NaOH (250 mL), water (250 mL), saturated NaCl (2×100 mL), dried with CH₂Cl₂, and concentrated in vacuo. The residue was purified by flash chromatography (silica gel, 7.5×36 cm Biotage KP-Sil column, eluted with 5–10% diethyl ether in dichloromethane) to yield the product as a light yellow syrup (17.4 g, 80%). ¹H NMR (300 MHz, CDCl₃) δ7.44–7.22 (m, 10H), 6.81–6.72 (m, 3H), 5.14 (s, 2H), 3.86 (s, 3H), 3.72–3.67 (m, 2H), 3,58 (d, J=13.0 Hz, 1H), 3.08 (d, J=9.7 Hz, 1H), 2.99 (dd, J=8.9, 7.8 Hz, 1H), 2.74 (dd, J=9.1, 7.4 Hz, 1H), 2.33 (d, J=9.7 Hz, 1H), 2.15 (s, 3H), 0.68 (s, 3H). ¹³C NMR (75 MHz, CDCl₃) δ211.3, 148.4, 147.4, 139.2, 137.2, 132.7, 128.51, 128.50, 128.3, 127.8, 127.4, 127.0, 121.6, 115.5, 111.2, 71.0, 63.8, 60.0, 59.5, 57.9, 56.0, 47.7, 25.6, 20.6.

The following Intermediates 14 and 15 were prepared in the same manner:

Intermediate 14

1-{(3SR, 4RS)-1-Benzyl-4-[3-(indan-2-yloxy)-4-methoxyphenyl]-3-methyl-pyrrolidin-3-yl}-ethanone

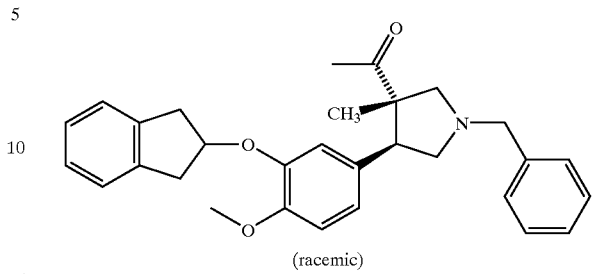

(racemic)

¹H NMR (300 MHz, CDCl₃) δ7.38–7.16 (m, 9H), 6.88 (br s, 1H), 6.78 (br s, 2H), 5.18–5.13 (m, 1H), 3.82–3.73 (m, 2H), 3.79 (s, 3H), 3.60 (d, J=13.0 Hz, 1H), 3.41–3.17 (m, 4H), 3.14 (d, J=9.7 Hz, 1H), 3.05 (t, J=8.3 Hz, 1H), 2.84 (t, J=8.3 Hz, 1H), 2.44 (d, J=9.7 Hz, 1H), 2.24 (s, 3H), 0.86 (s, 3H).

Intermediate 15 trans-(±)-1-[1-Benzyl-4-(3-cyclopentyloxy-4-methoxy-phenyl)-3-methyl-pyrrolidin-3-yl]-ethanone

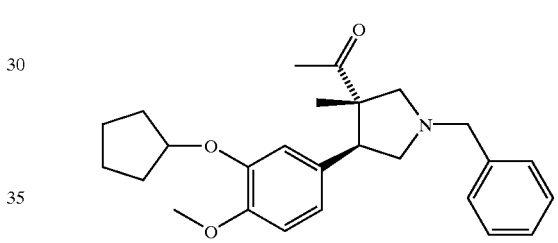

Intermediate 15 was prepared according to the procedure outlined in J. A. Stafford et al., *J. Med. Chem.*, 38, pp. 4972–4975 (1995), incorporated herein by reference.

Intermediate 16

Preparation of Trans-(±)-[3-Acetyl-4-(3-benzyloxy-4-methoxyphenyl)-3-methyl]-pyrrolidine-1-carboxylic Acid Methyl Ester

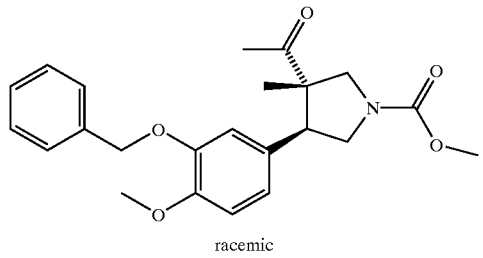

racemic

A solution of Intermediate 13 (17.4 g, 40.5 mmol, 1 eq) in acetonitrile (150 mL) was treated with methyl chloroformate (15.6 mL, 202.5 mmol, 5 eq), and the mixture was stirred at reflux 1 hour. The reaction mixture was concentrated, and the residue was purified by flash chromatography (silica gel, 7.5×36 cm Biotage KP-Sil column, eluted with 50–60% ethyl acetate in heptane) to afford the product as a colorless syrup (13.7 g, 85%). ¹H NMR (300 MHz, CDCl₃) δ7.42–7.27 (m, 5H), 6.82 (d, J=8.8 Hz, 1H), 6.69 (br d, J=8.3 Hz, 1H), 6.63 (d, J=1.8 Hz, 1H), 5.15 (s, 2H), 3.88 (s, 3H), 3.84 (dd, J=16.3, 11.0 Hz, 1H), 3.73 (br s, 3H), 3.24/3.12 (2 d, J=11.31/11.0 Hz, 1H), 2.09/2.01 (2 s, 3H), 0.84 (s, 3H). $^{13}$C NMR (75 MHz, CDCl$_3$) δ210.0/209.8, 155.2, 149.0, 147.5, 137.0, 130.5/130.0, 128.5, 127.8, 127.2/127.1, 121.2/121.0, 114.9/114.8, 111.5, 70.9, 58.1/57.2, 55.9, 54.4/54.0, 52.5, 50.2/50.0, 48.4/48.0, 26.3, 17.5.

The following Intermediates 17 and 18 were prepared in the same manner:

Intermediate 17 trans-(±)-3-Acetyl-4-[3-(indan-2-yloxy)-4-methoxyphenyl]-3-methyl-pyrrolidine-1-carboxylic Acid Methyl Ester

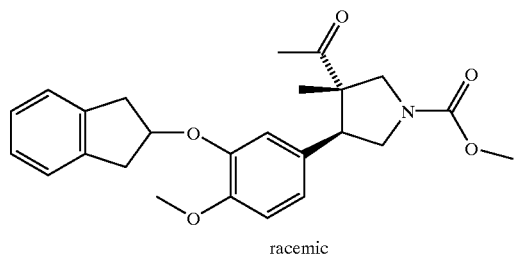

racemic $^1$H NMR (300 MHz, CDCl$_3$) δ7.24–7.16 (m, 4H), 6.82 (d, J=8.8 Hz, 1H), 6.75–6.72 (m, 2H), 5.18–5.10 (m, 1H), 3.91 (t, J=11.2 Hz, 1H), 3.80 (s, 3H), 3.77–3.65 (m, 3H), 3.74 (s, 3H), 3.42–3.16 (m, 5H), 2.17 (d, J=6.8 Hz, 3H), 1.04 (s, 3H). $^{13}$C NMR (75 MHz, CDCl$_3$) δ210.1/209.9, 155.3, 149.4, 146.9/146.8, 140.5/140.4, 130.5/130.0, 126.7, 124.7, 121.3/121.1, 116.1/115.8, 111.9, 79.2, 58.2/57.4, 55.9, 54.7/54.2, 52.6, 50.2/50.0, 48.5/48.1, 39.7, 26.6/26.5, 17.8.

Intermediate 18 trans-(±)-3-Acetyl-4-(3-cyclopentyloxy-4-methoxyphenyl)-3-methyl-pyrrolidine-1-carboxylic Acid Methyl Ester

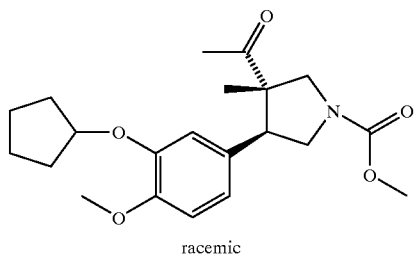

racemic

Analytical data compared to identical compound prepared in Example 12 of Feldman et al. U.S. Pat. No. 5,665,754, incorporated herein by reference, which confirmed the structure of Intermediate 18.

Intermediate 19

Preparation of trans-(±)-[3-Acetyl-4-(3-hydroxy-4-methoxyphenyl)-3-methyl]-pyrrolidine-1-carboxylic Acid Methyl Ester

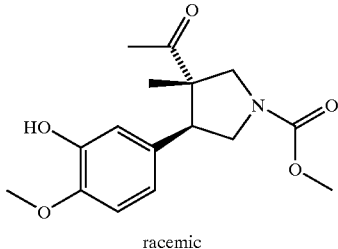

racemic

A solution of Intermediate 16 (8.7 g, 21.9 mmol) in ethanol (50 mL) was shaken for 16 hours under H$_2$ (50 psi) in the presence of a palladium on carbon catalyst (0.5 g, 10% Pd/C). The catalyst was filtered through a pad of celite followed by a 0.22 um membrane filter. The filtrate was concentrated in vacuo to give the product as a clear syrup (6.5 g, 97%). $^1$H NMR (300 MHz, CDCl$_3$) δ6.79 (d, J=8.3 Hz, 1H), 6.74 (d, J=1.8 Hz, 1H), 6.63 (br d, J=8.3 Hz, 1H), 6.04 (br s, 1H), 3.96–3.85 (m, 1H), 3.87 (s, 3H), 3.75/3.73 (2 s, 3H), 3.74–3.59 (m, 3H), 3.36/3.26 (2 d, J=11.2/11.0 Hz, 1H), 2.17/2.15 (2 s, 3H), 1.01 (s, 3H). $^{13}$C NMR (75 MHz, CDCl$_3$) δ210.0/209.8, 155.3, 145.9/145.8, 145.5, 131.2/130.8, 119.9, 114.5, 110.6, 58.1/57.2, 55.8, 54.4/53.9, 52.5, 50.3/50.1, 48.4/48.0, 26.3, 17.6.

Intermediate 20

Preparation of trans-3-Acetyl-4-[exo-3-(bicyclo[2.2.1]hept-2-yloxy)-4-methoxyphenyl]-3-methyl-pyrrolidine-1-carboxylic Acid Methyl Ester

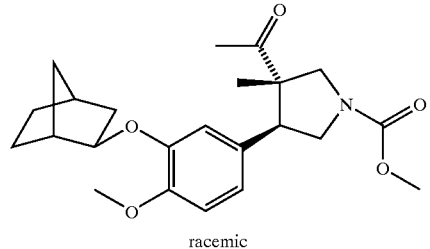

racemic

To a solution of Intermediate 19 (1.11 g, 3.61 mmol, 1 eq), endo-norborneol (387 mg, 3.4 mmol, 0.95 eq), and triphenylphosphine (947 mg, 3.61 mmol, 1 eq) in dry THF (10 mL) was added with diethylazodicarboxylate (568 uL, 3.61 mmol, 1 eq) dropwise. The reaction mixture was stirred for 16 hours at reflux, diluted with ethyl acetate (75 mL), washed with water (75 mL), 1 M NaOH (3×20 mL), water (20 mL), and brine (20 mL), dried with CH$_2$Cl$_2$, and concentrated in vacuo. The crude residue was purified by flash chromatography (silica gel, 4×9 cm Biotage KP-Sil column, eluted with 40% ethyl acetate in heptane, to afford the product as a colorless syrup (522 mg, 36%). $^1$H NMR (300 MHz, CDCl$_3$) δ6.80 (d, J=8.2 Hz, 1H), 6.66 (d, J=9.0 Hz, 1H), 6.62 (s, 1H), 4.15–4.08 (m, 1H), 3.95–3.86 (m, 1H), 3.83 (s, 3H), 3.74 (s, 3H), 3.73–3.60 (m, 3H), 3.37/3.28 (2 d, J=11.2/10.8 Hz, 1H), 2.47 (br s, 1H), 2.32 (br s, 1H), 2.17/2.15 (2 s, 3H), 1.76–1.66 (m, 2H), 1.63–1.45 (m, 3H), 1.28–1.08 (m, 3H), 1.02/1.01 (2 s, 3H). $^{13}$C NMR (75 MHz, CDCl$_3$) δ210.5/210.3, 155.7, 149.6, 147.4, 130.8/130.76, 130.3, 120.9/120.7/-120.5, 115.6/115.4/115.3/115.2, 112.2, 81.5, 58.6/-57.8, 56.4, 54.9/54.6, 52.9, 50.6/50.5, 49.1/49.0/-48.7, 41.5, 40.4, 35.8/35.7, 28.8, 26.9/26.8, 24.7/-24.6, 18.2.

The following Intermediates 21–23 were prepared in the same manner:

Intermediate 21 trans-[3-Acetyl-4-[4-methoxy-3-(1-methyl-3-phenyl-propoxy)phenyl]-3-methyl-pyrrolidine-1-carboxylic Acid Methyl Ester

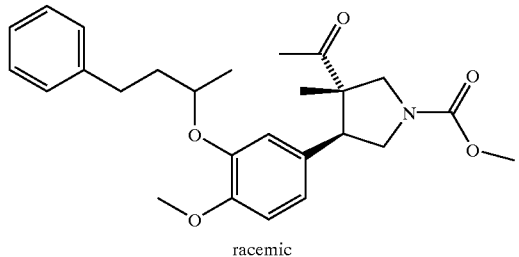

racemic $^1$H NMR (300 MHz, CDCl$_3$) δ7.29–7.15 (m, 5H), 6.82 (d, J=8.3 Hz), 6.72–6.63 (m, 2H), 4.33–4.25 (m, 1H), 3.94–3.59 (m, 4H), 3.84 (s, 3H), 3.74 (br s, 3H), 3.36/3.27 (2 dd, J=11.2, 3.0/10.9, 3.9 Hz, 1H), 2.88–2.69 (m, 2H), 2.18–2.06 (m, 4H), 1.95–1.82 (m, 1H), 1.33/1.31 (2 d, J=2.3/2.3 Hz, 3H), 1.01/0.99 (2 s, 3H). $^{13}$C NMR (75 MHz, CDCl$_3$) δ (209.9, 155.4, 149.8, 147.1, 141.9, 130.4/129.9, 128.5, 128.4, 125.8, 121.2, 116.9, 111.9, 74.8, 58.1/57.3, 55.9, 54.6/54.3, 52.6, 50.2/50.1, 48.6/48.2, 38.1, 31.8, 26.6, 19.9, 17.7.

Intermediate 22 trans-(±)-3-Acetyl-4-(4-methoxy-3-phenethyloxy-phenyl)-3-methylpyrrolidine-1-carboxylic Acid Methyl Ester

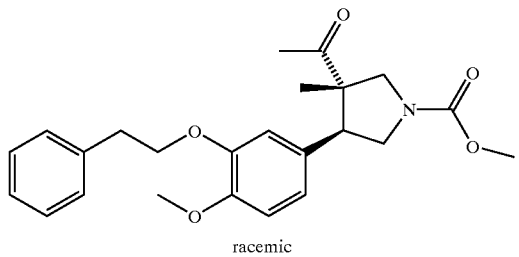

racemic $^1$H NMR (300 MHz, CDCl$_3$): δ7.36–7.23 (m, 5H), 6.82 (d, J=8.2 Hz, 1H), 6.70 (d, J=8.4 Hz, 1H), 6.66 (s, 1H), 4.18 (t, J=7.5 Hz, 2H), 3.92–3.81 (m, 1H), 3.86 (s, 3H), 3.76–3.61 (m, 3H), 3.73 (s, 3H), 3.40/3.27 (2 d, J=11.2/10.9 Hz, 1H), 3.15 (t, J=7.5 Hz, 2H), 2.16/2.12 (2 s, 3H), 1.00 (s, 3H).

Intermediate 23

Trans-3-Acetyl-4-[4-methoxy-3-(tetrahydro-furan-3-yloxy)-phenyl]-3-methylpyrrolidine-1-carboxylic Acid Methyl Ester

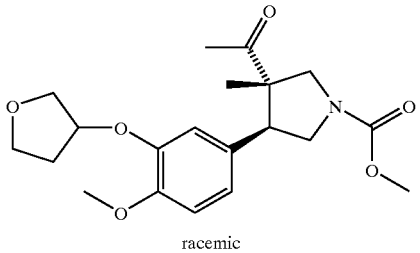

racemic $^1$H NMR (300 MHz, CDCl$_3$): δ6.85–6.63 (m, 3H), 4.92–4.88 (m, 1H), 4.07–3.62 (m, 8H), 3.84 (s, 3H), 3.75 (s, 3H), 3.39/3.29 (2 d, J=11.2/10.2 Hz, 1H), 2.19–2.14 (m, 5H), 1.02 (br s, 3H). $^{13}$C NMR (75 MHz, CDCl$_3$): δ(210.0/209.9, 155.4, 149.5, 146.5, 130.0, 121.6/121.5, 116.5/116.4/116.3, 112.0, 111.0, 78.9, 73.0, 67.2, 58.1/57.3, 55.9, 54.7/54.3, 52.6, 50.1/50.0, 48.4/48.0, 33.0, 26.6, 17.8.

Intermediate 24

Preparation of (Z)-3-(3-Benzyloxy-4-methoxy-phenyl)-2-methylacrylic Acid Methyl Ester

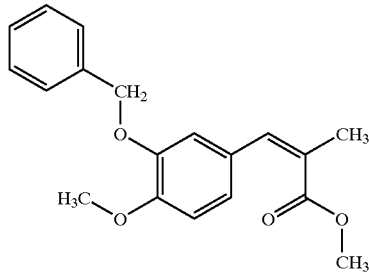

Synthesis of Intermediate 24 was achieved using commercially available 3-benzyloxy-4-methoxy-benzaldehyde, and the procedures outlined in K. Ando, *Tetrahedron Lett.*, 36, 4105–4108, (1995), and K. Ando, *J. Org. Chem.*, 63, 8411–8416, (1998). The structure of Intermediate 24 was confirmed by $^1$H NMR (300 MHz, CDCl$_3$): δ7.30–7.46 (m, 5H) ; 6.89 (s, 1H) 6.83–6.84 (m, 2H); 6.57 (s, 1H); 5.11 (s, 2H); 3.88 (s, 3H); 3.61 (s, 3H); 2.06 (2s, 3H)

Intermediate 25

Preparation of (Z)-3-(3-Benzyloxy-4-methoxy-phenyl)-2-methylacrylic Acid

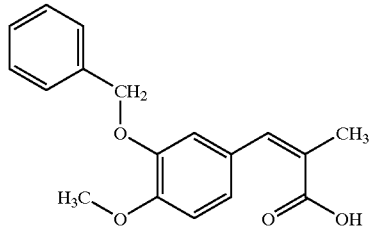

Intermediate 24 (20 mmol, 6.2 g) was hydrolyzed using LiOH (30 mmol, 1.26 g) in 67% dioxane and water at 80° C. for 16 hours. The resulting solution was concentrated under reduced pressure, water then was added, and next the basic aqueous layer was extracted two times with ethyl acetate. The aqueous layer was acidified to pH<2, then extracted three times with ethyl acetate. The acid extracted ethyl acetate was combined, washed with saturated NaHCO$_3$, then dried over Na$_2$SO$_4$. The product was used without further purification.

$^1$H NMR (300 MH$_3$, CDCl$_3$): δ7.30–7.46 (m, 5H) ; 6.89 (s, 1H); 6.83–6.84 (sd, 2H); 6.57 (sd, 1H); 5.11 (s, 2H); 3.88 (s, 3H); 3.61 (s, 3H); 2.06 (s, 3H).

Intermediate 26

Preparation of (Z)-3-(3-Benzyloxy-4-methoxyphenyl)-N-methoxy-2,N-dimethyl-acrylamide

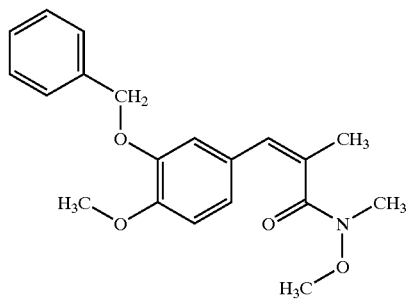

Intermediate 26 was prepared by first dissolving Intermediate 25 (19.8 mmol, 5.9 g) in chloroform. To this solution was added carbonyl diimidazole (23.76 mmol, 3.85 g), and the resulting solution stirred at least 1 hour. A slurry of methyl methoxy amine hydrochloride (21.8 mmol, 2.11 g) and triethylamine (22 mmol, 3.07 mL) in chloroform was prepared, and added to the activated carboxylic acid. The resulting solution was stirred 16 hours. Then, the organic layer was washed twice with 1N HCl, two times with saturated NaHCO$_3$, and finally dried over Na$_2$SO$_4$. The solvents were removed under reduced pressure, and the resulting oil was purified by column chromatography. The synthesis of Intermediate 26 was confirmed by MS, m/z 342 da (observed).

Intermediate 27

Preparation of (Z)-4-(3-Benzyloxy-4-methoxyphenyl)-3-methyl-but-3-en-2-one

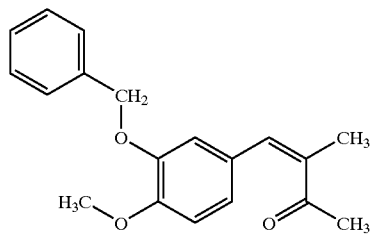

Intermediate 27 was prepared by dissolving Intermediate 26 (0.59 mmol, 0.20 g) in THF, and cooling the resulting solution to 0° C. A first portion of methyl magnesium bromide (0.64 mmol, 0.213 mL) was added, and the solution slowly warmed to room temperature. Second and third portions, equal to the first portion, of the methyl magnesium bromide reagent were added over the next 20 hours. The reaction was quenched with saturated NH$_4$Cl, and the solvents were removed under reduced pressure. The residue was resuspended in ethyl acetate, then the organic layer was washed two times with 1N HCl and two times with saturated NaHCO$_3$. The organic layer was dried over Na$_2$SO$_4$. The solvents were removed under reduced pressure and the resulting oil purified over silica gel. $^1$H NMR (300 MHz, CDCl$_3$): δ7.30–7.45 (m, 5H); 6.82–6.85 (sd, 1H); 6.73–6.77 (m, 2H); 6.63 (s, 1H); 5.13 (s, 2H); 3.89 (s, 3H); 1.97 (2d, 3H) ; 1.90 (s, 3H)

Intermediate 28

Preparation of (3RS, 4SR-1-Benzyl-4-(3-benzyloxy-4-methoxyphenyl)-3-methylpyrrolidine-3-carboxylic Acid Methyl Ester

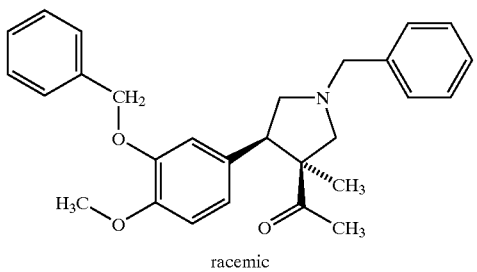

racemic

Intermediate 28 was prepared by converting (Z)-3-(3-benzyloxy-4-methoxy-phenyl)-2-methyl-acrylic acid methyl ester (Intermediate 24) to the named pyrrolidine according to a standard [3+2] cycloaddition procedure, as disclosed above in Intermediate 3.

$^1$H NMR (300 MHz, CDCl$_3$): δ7.24–7.48 (m, 10); 6.84 (s, 1H0; 6.76 (s, 2H); 5.12 (sd, 2H); 3.84 (s, 3H); 3.67–3.79 (q, 2H); 3.25–3.28 (d, 1H); 3.14 (s, 3H); 3.08–3.11 (m, 2H); 2.76–2.78 (t, 1H); 2.66–2.69 (d, 1H); 1.42 (s, 3H).

Intermediate 29

Preparation of 1-[(3RS, 4SR)-1-Benzyl-4-(3-benzyloxy-4-methoxyphenyl)-3-methyl-pyrrolidin-3-yl]-ethanone

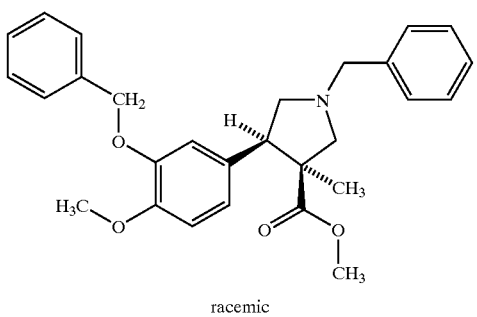

racemic

Intermediate 29 was prepared by converting (Z)-4-(3-benzyloxy-4-methoxy-phenyl)-3-methyl-but-3-en-2-one (Intermediate 27) to the named pyrrolidine according to the standard [3+2] cycloaddition procedure, as disclosed above in Intermediate 3. The structure of Intermediate 29 was confirmed by MS, m/z 430 da.

Intermediate 30

Preparation of (3RS, 4SR)-4-(3-Benzyloxy-4-methoxy-phenyl)-3-methylpyrrolidine-1,3-dicarboxylic Acid Dimethyl Ester

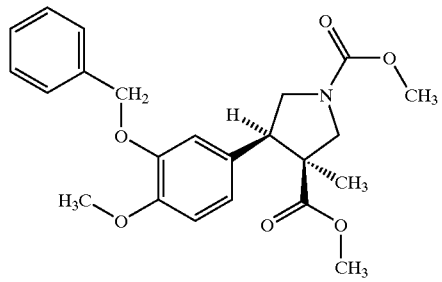

Intermediate 30 was prepared by converting (3RS, 4SR-1-benzyl-4-(3-benzyloxy-4-methoxy-phenyl)-3-methyl-pyrrolidine-3-carboxylic acid methyl ester (Intermediate 28) to the named carbamate according to a standard debenzylation procedure with methyl chloroformate, as set forth in Intermediate 16.

$^1$H NMR (300 Mz, CDCl$_3$): δ7.28–7.44 (m, 5H); 6.79–6.82 (d, 1H); 6.68–6.71 (m, 2H); 5.11 (s, 2H); 3.91–3.96 (d, 1H); 3.86 (s, 3H); 3.78–3.83 (m, 1H); 3.75 (s, 3H); 3.35, 3.37 (2s, 3H); 3.30–3.34 (d, 1H); 3.10–3.15 (t, 1H); 2.74–2.77 (d, 1H); 1.32 (s, 3H).

Intermediate 31

Preparation of (3RS, 4SR)-3-Acetyl-4-(3-benzyloxy-4-methoxy-phenyl)-3-methylpyrrolidine-1-carboxylic Acid Methyl Ester

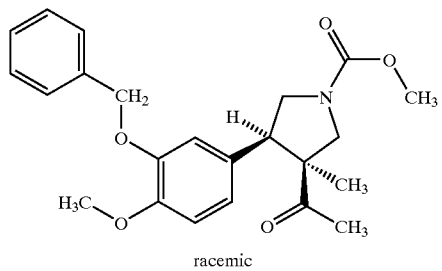

racemic

Intermediate 31 was prepared by converting 1-[(3RS, 4SR)-1-benzyl-4-(3-benzyloxy-4-methoxy-phenyl)-3-methyl-pyrrolidin-3-yl]-ethanone (Intermediate 29) to the named carbamate according to a standard debenzylation procedure with methyl chloroformate, as set forth in Intermediate 16. The structure of Intermediate 31 was confirmed by MS m/z 398, 420 observed.

Intermediate 32

Preparation of (3RS, 4SR)-4-(3-Hydroxy-4-methoxy-phenyl)-3-methylpyrrolidine-1,3-dicarboxylic Acid Dimethyl Ester

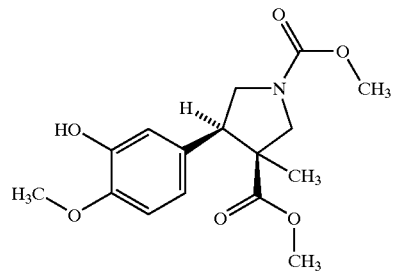

Hydrogenation of Intermediate 30 in ethanol with a catalytic amount of Pd/C (H$_2$, 30 psi) yielded 4-(3-hydroxy-4-methoxy-phenyl)-3-methyl-pyrrolidine-1,3-dicarboxylic acid dimethyl ester (i.e., Intermediate 32). The catalyst was removed by filtration, then the solvents were removed under reduced pressure. The product was used without further purification.

$^1$H NMR (300 MHz, CDCl$_3$): δ6.72–6.77 (m, 2H) ; 6.61–6.63 (sd, 1H); 3.9–4.05 (2d, 1H); 3.86 (s, 3H); 3.71–3.82 (m, 1H); 3.75 (s, 3H); 3.49 (s, 3H); 3.29–3.39 (2d, 1H); 3.15–3.16 (m, 1H); 1.38 (s, 3H).

Intermediate 33

Preparation of (3RS, 4SR)-3-acetyl-4-(3-hydroxy-4-methoxyphenyl)-3-methylpyrrolidine-1-carboxylic Acid Methyl Ester

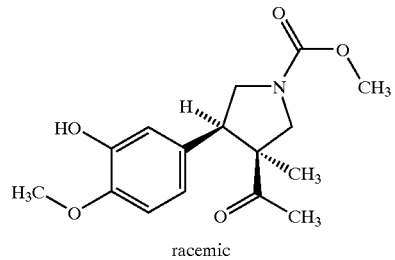

racemic

Hydrogenation of (3RS, 4SR)-3-acetyl-4-(3-benzyloxy-4-methoxy-phenyl)-3-methyl-pyrrolidine-1-carboxylic acid methyl ester (Intermediate 31) in ethanol with a catalytic amount of Pd/C (H$_2$30 psi) yielded the named ester. The structure of Intermediate 33 was confirmed by MS m/z 308.

Intermediate 34

Preparation of (3RS, 4SR)-4-(3-cyclopentyloxy-4-methoxyphenyl)-3-methyl-pyrrolidine-1,3-dicarboxylic Acid Dimethyl Ester

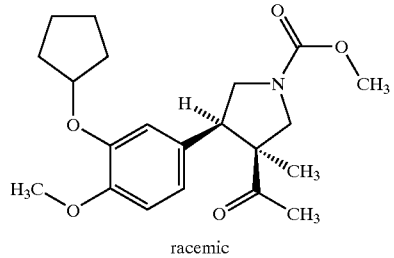

racemic

Intermediate 32 was alkylated according to a standard O-alkylation procedure outlined in Intermediate 20 to yield 4-(3-cyclopentyloxy-4-methoxy-phenyl)-3-methyl-pyrrolidine-1,3-dicarboxylic acid dimethyl ester (i.e., Intermediate 34). $^1$H NMR (300 MHz, CDCl$_3$): δ6.76–6.79 (d, 1H); 6.65–6.67 (sd, 2H); 4.71–4.72 (bs, 1H); 3.97–4.07 (2d, 2H); 3.83–3.90 (m, 1H); 3.82 (s, 3H); 3.76 (s, 3H); 3.45 (s, 3H); 3.30–3.41 (2d, 1H); 3.15–3.20 (t, H), 1.87–1.94 (bm, 6H); 1.79–1.84 (bm, 2H); 1.40 (s, 3H).

Intermediate 35

Preparation of (3RS,4SR-3-Acetyl-4-(3-cyclopentyl-oxy-4-methoxyphenyl)-3-methylpyrrolidine-1-carboxylic Acid Methyl Ester

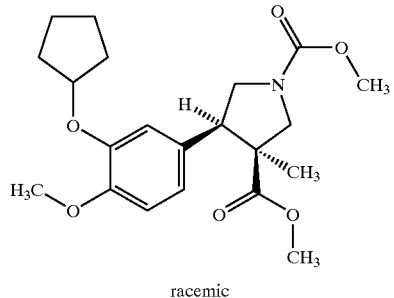

racemic

Alkylation of (3RS, 4SR)-3-acetyl-4-(3-hydroxy-4-methoxy-phenyl)-3-methyl-pyrrolidine-1-carboxylic acid methyl ester (Intermediate 33) was performed according to a standard O-alkylation procedure, as outlined in Intermediate 20, to provide the named compound.

$^1$H NMR (300 MHz, CDCl$_3$): δ6.77–6.79 (d, 1H); 6.62–6.68 (sd, 2H); 4.00–4.07 (bs, 1H); 3.90–3.94 (t, $^1$H NMR (300 MHz, CDCl$_3$): δ6.77–6.79 (d, 1H); 6.62–6.68 (sd, 2H); 4.00–4.07 (bs, 1H); 3.90–3.94 (t, 1H); 3.86–3.88 (m, 1H); 3.82 (s, 3H); 3.74–3.75 (2s, 3H); 3.65–3.71 (m, 1H); 3.20–3.32 (2d, 1H); 3.14–3.19 (t, 1H); 1.76–1.92 (bm, 6H); 1.68 (s, 3H); 1.60–1.64 (bm, 2H) ; 1.44 (s, 3H)

Intermediate 36

Preparation of 1-Benzyl-4-(3-cyclopentyloxy-4-methoxyphenyl)-3-methylpyrrolidine-3-carboxylic Acid Ethyl Ester

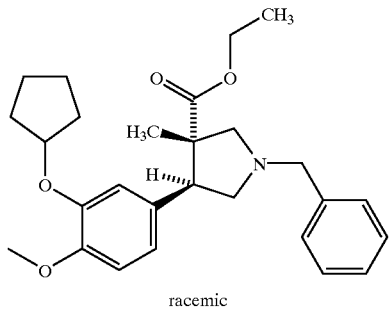

racemic

To a stirred solution of N-methoxymethyl-N-(phenylmethyl)trimethylsilylmethylamine (27 g, 113.7 mmol) and (E)-3-(3-cyclopentyloxy-4-methoxy-phenyl)-2-methyl-acrylic acid ethyl ester (19 g, 62.4 mmol) in CH$_2$Cl$_2$ (50 mL), cooled to 0° C., was added trifluoroacetic acid (1.0 M in CH$_2$Cl$_2$, 22.8 mL, 22.8 mmol). The reaction mixture was stirred at room temperature for 1 hour, then another molar equivalent of N-methoxymethyl-N-(phenylmethyl)trimethylsilylmethylamine (14.8 g, 62.4 mmol) added over 10 minutes. Stirring was continued for 3 hours, then the CH$_2$Cl$_2$ was removed under reduced pressure. The residue was dissolved in ethyl acetate and washed with 1.0 N aqueous HCl (2×50 mL), water, 1.0 N aqueous NaOH solution, water, and brine, then dried over Na$_2$SO$_4$, filtered, and concentrated under reduced pressure to provide a pale yellow oil. Chromatography on silica gel (9:1, hexanes:ethyl acetate) provided the product as an amber oil (16.7 g, 61% yield). $^1$H NMR (300 MHz, CDCl$_3$): δ(ppm); 7.39–7.23 (m, 5H, aromatic), 6.91 (s, 1H, aromatic), 6.78 (m, 2H, aromatic), 4.75 (m, 1H), 4.18 (q, 2H, OEt), 3.86 (m, 1H), 3.81 (s, 3H, OCH$_3$), 3.75 (d, 1H, J=13.2 Hz), 3.62 (d, 1H, J=13.2 Hz), 3.20 (d, 1H, J=9.5 Hz), 3.01 (m, 1H), 2.91 (m, 1H), 2.51 (d, 1H, J=9.5 Hz), 1.93–1.58 (M, 8H, cyclopentyl), 1.28 (t, 3H, OEt), 0.9 (s, 3H, CH$_3$).

Intermediate 37

Preparation of 1-Benzyl-4-(3-cyclopentyloxy-4-methoxyphenyl)-3-methylpyrrolidine-3-carboxaldehyde

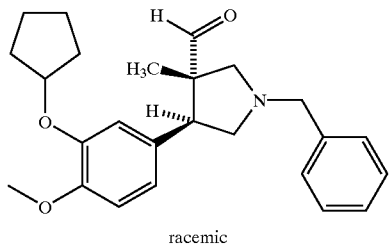

racemic

A solution of oxalyl chloride (4.87 mL, 9.73 mmol) in dry CH$_2$Cl$_2$ (20 mL) was chilled to −78° C. under N$_2$ and stirred while being treated with a solution of dimethyl sulfoxide (DMSO, 1.38 mL, 19.5 mmol) in CH$_2$Cl$_2$ (5 mL). Gas evolution was observed. When addition was complete, the solution was stirred for 5 minutes and a solution of

[1-benzyl-4-(3-cyclopentyloxy-4-methyoxy-phenyl)-3-methyl-pyrrolidin-3-yl]-methanol (3.5 g, 8.85 mmol) in CH$_2$Cl$_2$ (10 mL) was added over a period of 10 minutes. The mixture was stirred for 30 minutes, treated with triethylamine (6.7 mL, 44.3 mmol), and allowed to warm to room temperature. Water was added to the mixture, the resulting layers separated, and the aqueous layer extracted with CH$_2$Cl$_2$ (2×50 mL). The combined organic layers were washed with brine, dried over Na$_2$SO$_4$, and concentrated to give an oily product (3.2 g, 92% yield). $^1$H NMR (300 MGz, CDCl$_3$) δ(ppm): 9.63 (s, 1H, CHO), 7.34–7.21 (m, 5H, aromatic), 6.78–6.68 (m, 3H, aromatic), 4.73 (br, m, 1H), 3.80 (s, 3H, OCH$_3$), 3.78–3.61 (m, 3H), 3.18–3.11 (m, 2H), 2.86–2.81 (m, 1H), 2.58–2.52 (m, 1H), 2.43–2.34 (m, 2H), 1.87–1.59 (m, 8H, cyclopentyl), 0.74 (s, 3H, CH$_3$)

Intermediate 38

Preparation of (3S,4S)-4-(3-cyclopentyloxy-4-methoxyphenyl)-3-methyl-1-benzylpyrrolidine-3-carboxaldehyde Reduction/Oxidation Procedure To a cooled (−78° C.), stirred solution of acyl oxazolidinone-pyrrolidine (15.09 g; 27.2 mmol) in toluene (250 mL) was added a solution of lithium aluminum hydride in tetrahydrofuran (16.3 mL; 1.0 M; 16.3 mmol; 0.6 eq.) via syringe under nitrogen atmosphere. Vigorous bubbling was observed. The resulting solution was allowed to stir at −78° C. for 2 hours, then the cooling bath was removed and quenched with the successive addition of water (0.62 mL), 15% aqueous sodium hydroxide (0.62 mL) and more water (1.9 mL). The resulting mixture was allowed to warm to room temperature, stirred for 30 minutes, and then was diluted with ether (500 mL) and dried over MGSO$_4$. Filtration and concentration in vacuo provided the alcohol (with some aldehyde present) as a semisolid (14.8 g). This material was used immediately without further purification.

To a cooled (−78° C.), stirred solution of oxalyl chloride in dichloromethane (10.9 mL; 2.0 M; 21.8 mmol; 0.8 eq.) in more dichloromethane (75 mL) was added dimethylsulfoxide (3.1 mL; 43.5 mmol; 1.6 eq.) via syringe under nitrogen atmosphere. Vigorous bubbling was observed. After stirring at −78° C. for 20 minutes, a solution of the crude alcohol in dichloromethane (75 mL) was added via cannulae. The resulting yellow solution was allowed to stir at −78° C. for 20 minutes, then triethylamine (15.2 mL; 109 mmol; 4 eq.) was added via syringe. The reaction was allowed to stir at −78° C. for 20 minutes, then warm to room temperature and stirred for an additional 1 hour. The reaction was quenched with the addition of brine (150 mL), then extracted with dichloromethane (2×100 mL). The combined organic fractions were dried over MgSO$_4$, filtered, then concentrated in vacuo to provide the crude aldehyde. Purification by flash silica gel chromatography (25% ethyl acetate in hexanes) provided the aldehyde as a clear, colorless oil (9.8 g; 92%).

$^1$H NMR (CDCl$_3$, 400 MHz): δ9.64 (s, 1H), 7.37–7.26 (c, 5H), 6.78–6.76 (c, 2H), 6.70 (m, 1H), 4.74 (m, 1H), 3.82 (s, 3H), 3.70 (m, 1H), 3.64–3.62 (c, 2H), 3.18–3.13 (c, 2H), 2.84 (t, 1H), 2.41 (d, 1H), 1.94–1.83 (c, 6H), 1.63–1.59 (c, 2H), 0.74 (s, 3H).

LRMS (Electrospray, positive): Da/e 394.3 (m+1).

Intermediate 39

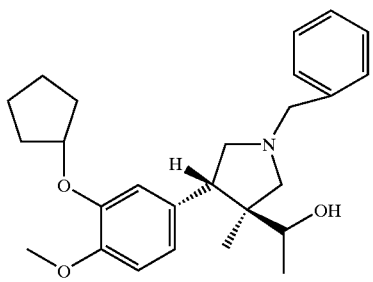

Grignard Addition Procedure

To a cooled (0° C.), stirred solution of Intermediate 38 (0.96 mg; 2.45 mmol) in dry ether (10 mL) was added a solution of methyl magnesium iodide (or other Grignards) in ether (2.45 mL; 3.0M; 7.35 mmol; 3 eq.) via syringe under nitrogen atmosphere. After stirring at 0° C. for 15 minutes, the reaction was allowed to warm to room temperature, then stirred for 2 hrs. The reaction then was carefully quenched with saturated aqueous ammonium chloride (40 mL), and extracted with ethyl acetate (3×50 mL). The combined organic fractions were washed with brine, dried over Na$_2$SO$_4$, filtered, then concentrated in vacuo to give 990 mg of an orange oil. Purification via flash silica gel chromatography (dichloromethane to 5% methanol in dichloromethane) afforded the less polar diastereomer (419 mg; 42%) and the more polar diastereomer (375 mg; 37%) as colorless, viscous oils.

Less Polar Diastereomer (42% yield): (1S)-1-[(3S,4S)-4-(3-cyclopentyloxy-4-methoxy-phenyl)-3-methyl-1-benzylpyrrolidin-3-yl]ethan-1-ol $^1$H NMR (CDCl$_3$, 400 MHz): δ7.34–7.28 (c, 5H), 6.79–6.73 (c, 3H), 4.74 (m, 1H), 3.82 (s, 3H), 3.74 (q, 1H), 3.65 (q, 2H), 3.53 (t, 1H), 3.40 (t, 1H), 2.99 (d, 1H), 2.50 (t, 1H), 2.35 (d, 1H), 1.94–1.81 (c, 6H), 1.63–1.59 (c, 2H), 1.10 (d, 3H), 0.52 (s, 3H).

LRMS (Electrospray, positive): Da/e 410.3 (m+1).

More Polar Diastereomer (37%): (1R)-1-[(3S,4S)-4-(3-cyclopentyloxy-4-methoxy-phenyl)-3-methyl-1-benzylpyrrolidin-3-yl]ethan-1-ol $^1$H NMR (CDCl$_3$, 400 MHz): δ7.33–7.31 (c, 5H), 6.79–6.72 (c, 3H), 4.74 (m, 1H), 3.82 (s, 3H), 3.69–3.56 (c, 4H), 3.29 (t, 1H), 3.10 (d, 1H), 2.56 (t, 1H), 2.09 (d, 1H), 2.04 (s, 3H), 1.92–1.81 (c, 6H), 1.62–1.59 (c, 2H), 1.13 (d, 3H), 0.47 (s, 3H).

LRMS (Electrospray, positive): Da/e 410.3 (m+1).

Compound IV

Preparation of (1R)-1-[(3S,4S)-4-(3-Cyclopentyloxy-4-methoxyphenyl)-3-methylpyrrolidin-3-yl]ethan-1-ol Prepared via hydrogenation of Intermediate 39.

$^1$H NMR (CDCl$_3$, 400 MHz): δ6.81 (d, 1H), 6.75–6.73 (m, 2H), 4.80 (c, 1H), 3.82 (s, 3H), 3.79–3.68 (m, 5H), 3.61 (t, 1H), 3.10 (d, 1H), 1.96–1.80 (m, 6H) 1.63–1.57 (m, 2H), 1.21 (d, 3H), 0.72 (s, 3H)

LRMS (Electrospray, positive): Da/e 320.4 (m+1).

Intermediate 40

Ethyl (2E)-3-(3-indan-2-yloxy-4-methoxyphenyl)-2-methylprop-2-enoate

Prepared from Intermediate 8 via the Horner Emmons procedure.

¹H NMR (CDCl₃, 400 MHz): δ7.64 (d, 1H), 7.28–7.17 (m, 4H), 7.06 (dd, 1H), 7.03 (d, 1H), 6.90 (d, 1H), 5.20 (c, 1H), 4.28 (q, 2H), 3.85 (s, 3H), 3.39 (dd, 2H) 3.26 (dd, 2H), 2.16 (d, 3H), 1.36 (t, 3H).
Intermediate 41

(2E)-3-(3-Indan-2-yloxy-4-methoxyphenyl)-2-methylprop-2-enoic acid

Prepared from Intermediate 40 via the lithium hydroxide hydrolysis procedure.
¹H NMR (D₆ DMSO, 400 MHz): δ7.56 (s, 1H), 7.25–7.11 (m, 5H), 7.06 (d, 1H), 6.99 (d, 1H), 5.22 (c, 1H), 3.71 (s, 3H), 3.34 (dd, 2H), 3.03 (d, 2H), 2.06 (s, 3H).
Intermediate 42

(2E)-3-(3-Indan-2-yloxy-4-methoxyphenyl)-2-methylprop-2-enoyl Chloride

Prepared from Intermediate 41 via the acid chloride procedure.
¹H NMR (CDCl₃, 400 MHz): δ8.01 (s, 1H), 7.29–6.93 (m, 7H), 5.23 (c, 1H), 3.89 (s, 3H), 3.42 (dd, 2H), 3.28 (dd, 2H), 2.26 (s, 3H).
Intermediate 43

3-[(2E)-3-(3-Indan-2-yloxy-4-methoxyphenyl)-2-methylprop-2-enoyl](4R)-4-phenyl-1,3-oxazolidin-2-one Prepared from Intermediate 42 via the oxazolidinone acylation procedure.
¹H NMR (CDCl₃, 400 MHz): δ7.43–7.33 (m, 5H), 7.25–7.16 (m, 4H), 7.07–7.03 (m, 2H), 6.89 (d, 1H), 5.54 (dd, 1H), 5.19 (c, 1H), 4.74 (t, 1H), 4.28 (dd, 1H), 3.84 (s, 3H), 3.38 (dd, 2H), 3.24 (dd, 2H), 2.19 (d, 3H).
Intermediate 44

(4R)-3-{[(3S,4S)-4-(3-Indan-2-yloxy-4-methoxyphenyl)-3-methyl-1-benzylpyrrolidin-3-yl]carbonyl}-4-phenyl-1,3-oxazolidin-2-one Prepared from Intermediate 43 via the cycloaddition procedure.
¹H NMR (CDCl₃, 400 MHz): δ7.45–7.12 (m, 15H), 6.95 (d, 1H), 6.78 (d, 1H), 5.54 (dd, 1H), 5.17 (c, 1H), 4.69 (t, 1H), 4.22 (dd, 1H), 4.11 (t, 1H), 3.84–3.60 (m, 5H), 3.51 (d, 1H), 3.37 (dt, 2H), 3.21 (dd, 2H), 2.90 (d, 1H), 2.85 (dd, 1H), 2.76 (dd, 1H), 1.12 (s, 3H).
Intermediate 45

(3S,4S)-4-(3-Indan-2-yloxy-4-methoxyphenyl)-3-methyl-1-benzylpyrrolidine-3-carbaldehyde Prepared from Intermediate 44 via the reduction/oxidation procedure.
¹H NMR (CDCl₃, 400 MHz): δ9.65 (s, 1H), 7.36–7.17 (m, 9H), 6.84 (d, 1H), 6.79 (d, 1H), 6.76 (dd, 1H), 5.16 (c, 1H), 3.79 (s, 3H), 3.76 (d, 1H), 3.68–3.63 (c, 1H), 3.40–3.31 (m, 2H), 3.24–3.13 (m, 2H), 2.85 (dd, 1H), 2.43 (d, 1H), 0.77 (s, 3H).
Compound V (1R)-1-[(3S,4S)-4-(3-Indan-2-yloxy-4-methoxyphenyl)-3-methyl-1-benzylpyrrolidin-3-yl]ethan-1-ol Desired, more polar diastereomer. Prepared from Intermediate 45 via the Grignard addition procedure.
¹H NMR (CDCl₃, 400 MHz): δ7.39–7.17 (m, 9H), 6.84–6.77 (m, 3H), 5.17 (c, 1H), 3.80 (s, 3H), 3.72–3.57 (m, 4H), 3.38–3.19 (m, 5H), 3.11 (d, 1H), 2.57 (t, 1H), 2.12 (d, 1H), 1.15 (d, 3H), 0.51 (s, 3H).
Compound VI (1R)-1-[(3S,4S)-4-(3-Indan-2-yloxy-4-methoxyphenyl)-3-methylpyrrolidin-3-yl]ethan-1-ol Prepared from Compound V via hydrogenation.
¹H NMR (CDCl₃, 400 MHz): δ7.26–7.16 (m, 4H), 6.81 (s, 3H), 5.19 (c, 1H), 3.80 (s, 3H), 3.74–3.68 (m, 2H), 3.44–3.17 (m, 8H), 2.66 (d, 1H), 2.51 (br s, 1H), 1.18 (d, 3H), 0.63 (s, 3H).
Intermediate 46

Ethyl (2E)-3-[4-methoxy-3-(phenylmethoxy)phenyl]-2-methylprop-2-enoate

Prepared from 3-benzyloxy-4-methoxy-benzaldehyde via the Horner Emmons procedure.
¹H NMR (CDCl₃, 400 MHz): δ7.56 (s, 1H), 7.44 (t, 2H), 7.36 (t, 2H), 7.30 (t, 1H), 7.01 (dd, 1H), 6.95 (d, 1H), 6.90 (d, 1H), 5.18 (s, 2H), 4.24 (q, 2H), 3.92 (s, 3H), 1.98 (d, 3H), 1.33 (t, 3H).
Intermediate 47

(2E)-3-[4-Methoxy-3-(phenylmethoxy)phenyl]-2-methylprop-2-enoic Acid

Prepared from Intermediate 46 via the lithium hydroxide hydrolysis procedure and performed without characterization.
Intermediate 48

(2E)-3-[4-Methoxy-3-(phenylmethoxy)phenyl]-2-methylprop-2-enoyl Chloride

Prepared from Intermediate 47 via the acid chloride procedure.
¹H NMR (CDCl₃, 400 MHz): δ7.91 (s, 1H), 7.47–7.29 (m, 5H), 7.10 (dd, 1H), 7.00 (d, 1H), 6.95 (d, 1H), 5.20 (s, 2H), 3.95 (s, 3H), 2.04 (s, 3H).
Intermediate 49

3-{(2E)-3-[4-Methoxy-3-(phenylmethoxy)phenyl]-2-methylprop-2-enoyl}(4R)-4-phenyl-1,3-oxazolidin-2-one Prepared from Intermediate 48 via the oxazolidinone acylation procedure.
¹H NMR (CDCl₃, 400 MHz): δ7.44–7.29 (m, 11H), 7.03–6.89 (m, 3H), 5.52 (dd, 1H), 5.17 (s, 2H), 4.73 (dt, 1H), 4.27 (dd, 1H), 3.91 (s, 3H), 2.00 (s, 3H).
Intermediate 50

(4R)-3-({(3S,4S)-4-[4-Methoxy-3-(phenylmethoxy)phenyl]-3-methyl-1-benzylpyrrolidin-3-yl}carbonyl)-4-phenyl-1,3-oxazolidin-2-one (Major Diastereomer)

Prepared from Intermediate 49 via the cycloaddition procedure.
¹H NMR (CDCl₃, 400 MHz): δ7.49–7.23 (m, 15H), 7.09 (d, 1H), 6.94 (dd, 1H), 6.80 (d, 1H), 5. 49 (dd, 1H) 5.17 (s, 2H), 4.66 (t, 1H), 4.19 (dd, 1H), 4.09 (t, 1H), 3.87 (s, 3H), 3.68 (q, 2H), 3.51 (d, 1H), 2.85–2.79 (m, 2H), 2.69 (dd, 1H), 0.99 (s, 3H).

Intermediate 51

(3S,4S)-4-[4-Methoxy-3-(phenylmethoxy)phenyl]-3-methyl-1-benzylpyrrolidine-3-carbaldehyde Prepared from Intermediate 50 via the reduction/oxidation procedure.

$^1$H NMR (CDCl$_3$, 400 MHz): δ9.56 (s, 1H), 7.43–7.22 (m, 10H), 6.79 (d, 1H), 6.77 (d, 1H), 6.71 (dd, 1H), 5.14 (dd, 2H), 3.86 (s, 3H), 3.71 (d, 1H), 3.62 (d, 1H), 3.57 (d, 1H), 3.13–3.08 (m, 2H), 2.73 (dd, 1H), 2.30 (d, 1H), 0.58 (s, 3H).

LRMS (Electrospray, positive): m/z 416.3 (m+1).

Compound VII

(1S)-1-{(3S,4S)-4-[4-Methoxy-3-(phenylmethoxy)phenyl]-3-methyl-1-benzylpyrrolidin-3-yl}ethan-1-ol Less polar diastereomer.

Prepared from Intermediate 51 via the Grignard procedure.

$^1$H NMR (CDCl$_3$, 400 MHz): δ7.44–7.22 (m, 10H), 6.80 (d, 1H), 6.75 (dd, 1H), 6.67 (d, 1H), 5.17 (s, 2H), 3.88 (s, 3H), 3.66 (q, 1H), 3.60 (d, 2H), 3.43 (t, 1H), 2.92 (d, 1H), 2.38 (t, 1H), 2.22 (d, 1H), 0.98 (d, 3H), 0.32 (s, 3H)

LRMS (Electrospray, positive): m/z 432.5 (m+1).

Compound VIII

(1R)-1-{(3S,4S)-4-[4-Methoxy-3-(phenylmethoxy)phenyl]-3-methyl-1-benzylpyrrolidin-3-yl}ethan-1-ol More polar, desired diastereomer.

Prepared from Intermediate 51 via the Grignard procedure.

$^1$H NMR (CDCl$_3$, 400 MHz): δ7.43–7.21 (m, 10H), 6.79 (d, 1H), 6.75–6.70 (m, 2H), 5.16 (dd, 2H), 3.87 (s, 3H), 3.64–3.49 (m, 4H), 3.23 (t, 1H), 3.06 (d, 1H), 2.46 (t, 1H), 1.99 (d, 1H), 1.07 (d, 3H), 0.28 (s, 3H).

LRMS (Electrospray, positive): m/z 432.5 (m+1).

Compound IX

5-[4-((1R)-1-hydroxyethyl)(3S,4S)-4-methylpyrrolidin-3-yl]-2-methoxyphenol

Prepared from Compounds VII and VIII via hydrogenation (10% palladium on carbon used in place of palladium acetate).

$^1$H NMR (CDCl$_3$, 400 MHz) δ 6.72 (d, 1H), 6.67 (d, 1H), 6.59 (dd, 1H), 3.80 (s, 3H), 3.60 (qd, 1H), 3.29–3.17 (m, 6H), 3.10 (t, 1H), 2.55 (d, 1H), 1.06 (d, 3H), 0.56 (s, 3H)

LRMS (Electrospray, positive): m/z 252.1 (m+1).

EXAMPLE 1

Preparation of trans-(±)-3-(1-Hydroxyethyl)-4-[3-(indan-2-yloxy)-4-methoxyphenyl]-3-methyl-pyrrolidine-1-carboxylic Acid Methyl Ester (2 Carbinol Diastereomers)

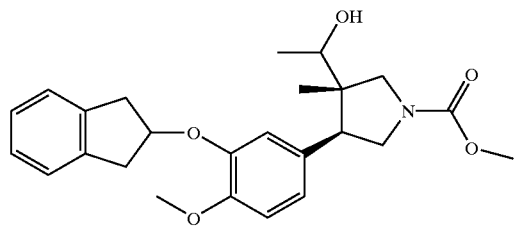

A solution of trans-3-acetyl-4-[3-(indan-2-yloxy)-4-methoxy-phenyl]-3-methyl-pyrrolidine-1-carboxylic acid methyl ester (Intermediate 17) (300 mg, 0.71 mmol, 1 eq) in ethanol (10 mL) was treated with sodium borohydride (54 mg, 1.42 mmol, 2 eq). The mixture was stirred for 10 min. at room temperature, treated with 1 N HCl (50 mL), and extracted with ethyl acetate (3×25 mL). The combined organic extracts were washed with 1 N HCl (25 mL), water, saturated sodium bicarbonate (25 mL), water (25 mL), and brine (25 mL), dried over CH$_2$Cl$_2$, and concentrated in vacuo. A portion of the crude residue was purified by HPLC (Vydac 20×250 mm C18 "Protein and Peptide" column, 8 min. gradient of 50–75% acetonitrile in water with each solvent containing 0.05% TFA, flow rate of 20 mL/min) to yield the separated diastereomers in a 2:1 ratio as colorless syrups (75 and 37 mg, respectively, in order of elution from column).

Isomer 1: $^1$H NMR (300 MHz, CDCl$_3$) δ7.24–7.15 (m, 4H), 6.83 (br s, 3H), 5.21–5.12 (m, 1H), 3.91–3.59 (m, 3H), 3.81 (s, 3H), 3.73 (s, 3H), 3.40–3.18 (m, 7H), 1.14 (d, J=6.3 Hz, 3H), 0.94 (s, 3H)

Isomer 2: $^1$H NMR (300 MHz, CDCl$_3$) δ7.23–7.15 (m, 4H), 6.85–6.82 (m, 3H), 5.22–5.10 (m, 1H), 3.89–3.67 (m, 3H), 3,81 (s, 3H), 3,75 (s, 3H), 3,64–3.52 (m, 2H), 3.40–3.15 (m, 5H), 1.20–1.13 (m, 3H), 0.78 (s, 3H).

The following Examples 2 and 3 were prepared in the same manner:

EXAMPLE 2

Trans-4-[3-exo-(±)-(Bicyclo[2.2.1]hept-2-yloxy)-4-methoxyphenyl]-3-(1-hydroxyethyl)-3-methyl-pyrrolidine-1-carboxylic Acid Methyl Ester (2 Carbinol Diastereomers)

Example 2 was prepared from Intermediate 20 to yield the separated diastereomers in a 9:1 ratio of Isomer 1 to Isomer 2.

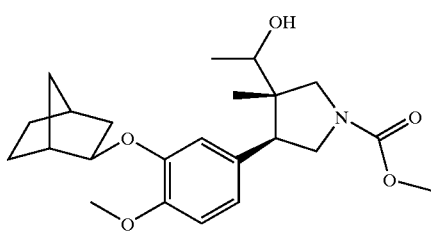

Isomer 1: $^1$H NMR (300 MHz, CDCl$_3$) δ6.82–6.72 (m, 3H), 4.15 (br s, 1H), 3.88–3.59 (m, 3H), 3.87 (s, 3H), 3.73

(s, 3H), 3.32–3.24 (m, 3H), 2.50–2.47 (m, 1H), 2.34–2.28 (m, 1H), 1.77–1.50 (m, 5H), 1.21–1.12 (m, 6H), 0.92 (s, 3H).

Isomer 2: ¹H NMR (300 MHz, CDCl₃) δ6.82–6.72 (m, 3H), 4.19–4.15 (m, 1H), 3.85–3.54 (m, 5H), 3.83 (s, 3H), 3.74 (s, 3H), 3.30/3.23 (2 d, J=10.4/10.4 Hz, 1H), 2.49–2.46 (m, 1H), 2.32 (br s, 1H), 1.76–1.70 (m, 2H), 1.65–1.44 (m, 3H), 1.21–1.14 (m, 6H), 0.75 (s, 3H)

EXAMPLE 3

Trans-3-(1-Hydroxyethyl)-4-[4-methoxy-3-(1-methyl-3-phenylpropoxy)phenyl]-3-methyl-pyrrolidine-1-carboxylic Acid Methyl Ester (2 Carbinol Diastereomers)

Example 3 was prepared from Intermediate 21.

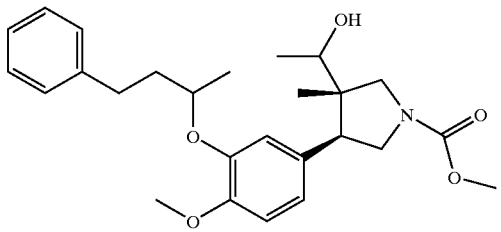

Isomer 1: ¹H NMR (300 MHz, CDCl₃) δ7.30–7.25 (m, 3H), 7.22–7.15 (m, 3H), 6.85–6.69 (m, 3H), 4.34–4.27 (m, 1H), 3.87–3.54 (m, 3H), 3.84 (s, 3H), 3.73/3.72 (2 s, 3H), 3.31–3.20 (m, 3H), 2.83–2.75 (m, 2H), 2.18/2.08 (m, 1H), 1.95–1.84 (m, 1H), 1.34/1.31 (2 s, 3H), 1.12 (d, J=6.3 Hz, 3H), 0.89 (br s, 3H). ¹³C NMR (75 MHz, CDCl₃) δ156.0, 150.3, 147.8, 142.2, 131.3/131.1, 128.9, 128.8, 126.2, 121.7, 117.1, 112.5, 77.6, 75.3/75.1, 74.1/74.0, 56.3, 56.2/55.8, 52.9, 52.0/51.5/51.2, 49.9/49.1, 38.5/38.4, 32.2, 20.3, 19.0/18.9, 14.6/14.5.

Isomer 2: ¹H NMR (300 MHz, CDCl₃) δ7.29–7.24 (m, 2H), 7.20–7.14 (m, 3H), 6.84–6.69 (m, 3H), 4.35–4.24 (m, 1H), 3.85/3.84 (2 s, 3H), 3.83–3.45 (m, 5H), 3.75 (s, 3H), 3.31–3.23 (m, 1H), 2.88–2.76 (m, 2H), 2,21–2.07 (m, 1H), 1.95–1.83 (m, 1H), 1.34/1.32 (2 s, 3H), 1.15–1.11 (m, 3H), 0.73 (br s, 3H). ¹³C NMR (75 MHz, CDCl₃) δ156.1, 149.9, 147.4, 142.3, 129.5/129.4, 128.9, 128.7, 126.2, 122.1/121.8, 117.9/117.7/117.4, 112.0, 77.6, 75.3/75.0/74.9, 69.4/69.3, 56.3, 53.2, 53.1, 49.5/49.3/49.1/48.6, 46.5/46.0, 38.5/38.4/38.3, 32.1, 20.3, 20.0, 17.7.

EXAMPLE 4

Preparation of Trans-(3-Cyclopentyloxy-4-methoxyphenyl)-3-(1-hydroxyethyl)-3-methyl-pyrrolidine-1-carboxylic Acid Methyl Ester (2 Carbinol Diastereomers)

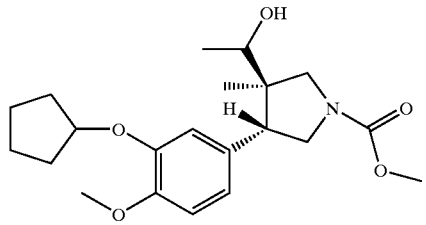

To the pyrrolidine ketone of Intermediate 18 (1.3 mmol, 0.50 g) in ethanol (10 mL) was added sodium borohydride (2.0 mmol, 0.075 9). After 1 hour at room temperature, the reaction was complete. The solvents were removed in vacuo, and the resulting oil diluted with water and extracted 3 times with ethyl acetate. The organic layer was washed 2 times with brine, then dried over MgSO₄. The desired product was obtained as an oil after removal of the solvents. ¹H NMR (300 MHz, CDCl₃) δ6.80 (d, 1H); 6.67 (d, 2H); 4.72 (bd, 1H); 3.86–3.95 (bm, 1H); 3.83 (S, 3H); 3.64–3.78 (bm, 1H); 3.74 (s, 3H); 3.33 (dd, 1H); 2.16 (d, 3H); 1.79–1.92 (bm, 4H); 1.59–1.63 (bm, 2H); 1.01 (sd, 3H).

The reaction to provide the compound of Example 4 yielded two diastereomers. To separate the alcohols, the crude diastereomers were dissolved in 50% acetonitrile and 50% water (50 mg/mL). Separation was performed by HPLC on a C-18 column (250×10 mm), and 400 μL of the crude material was injected. The starting concentration of eluent was 50% acetonitrile and 50% water each with 0.5% TFA, and remained the same for 2 minutes. After 20 minutes, the concentration was 5% water and 95% acetonitrile where it remained for 2 minutes. The column was returned to the starting conditions by minute 24 where it remained for 1 minute. The appropriate fractions were collected, combined, and dried to oils.

Spectral data for the four diastereomers:

¹H NMR (300 MHz, CDCl₃) for minor enantiomer pair: 6.75–6.82 (bm, 3H) ; 4.75 (bd, 1H) ; 3.83 (s, 3H); 3.64–3.81 (bm, 1H); 3.74 (s, 3H); 3.54–3.61 (bm, 2H); 3.28 (dd, 1H); 1.81–1.94 (bm, 5H); 1.58–1.65 (bm, 4H); 1.15 (dd, 3H); 0.75 (s, 3H).

¹H NMR (300 MHz, CDCl₃) for the major enantiomer pair: 6.76–6.83 (bm, 3H); 4.74 (bd, 1H); 3.77–3.89 (bm, 1H) ; 3.83 (s, 3H) ; 3.73 (s, 3H) ; 3.65 (quin, 1H) ; 3.25–3.32 (bm, 3H) ; 1.77–1.96 (bm, 7H); 1.58–1.61 (bm, 2H); 1.13 (d, 3H); 0.92 (s, 3H).

HPLC separation to achieve chiral separation of the four diastereomers required two columns. The first dextrose-based column (8×30 cm) was used to separate the first isomers, wherein 10 mL of a 7.1 mg/mL stock solution of crude mixture in column buffer was injected and eluted at 1 mL/min with isocratic hexanes (85%) and isopropanol (15%). The remaining mixture was purified on a separate dextrose-based column (10×50 cm), wherein 10 mL of a 7.1 mg/mL stock solution from column 1 was injected and eluted at 1 mL/min with isocratic hexanes (95%) and isopropanol (5%). The appropriate fractions were collected, combined and dried to oils.

EXAMPLE 5

Preperation of [1-Benzyl-4-(3-cyclopentyloxy-4-methoxyphenyl)-3-methylpyrrolidin-3-yl]-methanol

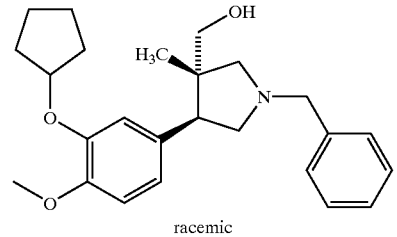

racemic

To a magnetically stirred solution of Intermediate 36 (9.32 g, 21.3 mmol) in dry toluene (10 mL) at 0° C. was added diisobutylaluminum hydride (64 mL, 1.0 M in CH₂Cl₂, 63.9 mmol). The mixture was stirred for 30 minutes at 0° C., and at room temperature for 1 hour, then quenched with methanol (20 mL). An HCl solution (1.0 N, 100 mL) then was added, and the mixture was stirred another 30 minutes. The two layers were separated, and the aqueous layer extracted with CH$_2$Cl$_2$ (2×20 mL). The organic extracts were washed with saturated NH$_4$Cl solution, dried over anhydrous Na$_2$SO$_4$, and concentrated to provide a light yellow oil (8.2 g, 98% yield). $^1$H NMR (300 MHz, CDCl$_3$) δ(ppm): 7.31–7.14 (m, 5H, aromatic), 6.78–6.71 (m, 3H, aromatic), 4.76–4.73 (br, m, 1H), 3.79 (s, 3H, OCH$_3$), 3.71–3.55 (m, 3H), 3.47–3.10 (m, 3H), 2.92 (d, 1H, J=9.2 Hz), 2.62 (m, 1H), 3.35–2.33 (m, 2H), 1.89–1.58 (m, 8H, cyclopentyl), 0.52 (s, 3H, CH$_3$).

EXAMPLE 6

Preparation of 1-[1-Benzyl-4-(3-cyclopentyloxy-4-methoxyphenyl)-3-methylpyrrolidin-3-yl]-1-hydroxy-propan-2-one

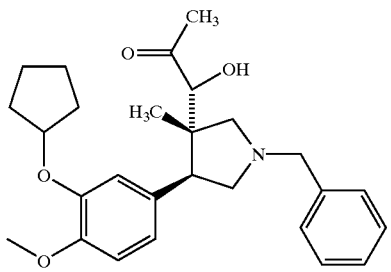

To a solution of ethyl vinyl ether (0.95 mL, 9.91 mmol) in dry THF (4 mL) at −78° C. was added 1.7 M t-butyllithium in pentane (5.25 mL, 8.93 mmol), and the solution was warmed to 0° C. Color changes from yellow to colorless occurred during this period. The resulting vinyl anion then was cooled to −78° C., and a solution of Intermediate 37 (1.95 g, 4.96 mmol) in THF (10 mL) was added dropwise. The resulting mixture was stirred for 45 minutes, quenched with saturated NH$_4$Cl (15 mL), and extracted with ether (3×30 mL). The combined organic extracts were dried over Na$_2$SO$_4$ and concentrated. The crude product was dissolved in ether, and treated with concentrated H$_2$SO$_4$ in a separatory funnel while shaking vigorously. The ether solution was washed with water (30 mL) and with saturated NaHCO$_3$ (30 mL) solution, dried over Na$_2$SO$_4$, and concentrated. The residue was purified by flash chromatography (silica gel, 20% ethyl acetate-hexanes) to produce the hydroxy ketone as an orange oil (1.36 g. 62% yield). $^1$H NMR (300 MHz, CDCl$_3$) δ(ppm) 7.34–7.27 (m, 5H, aromatic), 6.77–6.68 (m, 3H, aromatic), 4.75–4.72 (br, m, 1H), 4.13–4.08 (m, 1H), 3.81 (s, 3H, OCH$_3$), 3.79–3.57 (m, 3H), 3.26 (m, 1H) 2.99 (d, 1H, J=9.2 Hz), 2.69–2.64 (m, 1H), 2.39 (d, 1H, J=9.2 Hz), 2.25 (s, 3H, OCH$_3$), 1.94–1.59 (m, 8H, cyclopentyl), 0.69 (s, 3H, CH$_3$).

EXAMPLE 7

Preparation of 4-(3-Cyclopentyloxy-4-methoxyphenyl)-3-(1-hydroxy-1-methylethyl)-3-methylpyrrolidine-1-carboxylic Acid Methyl Ester

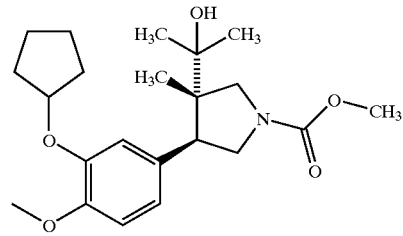

To a 3.0 M solution of methylmagnesium bromide (0.6 mL, 1.8 mmol) in ether at 0° C. was added a solution of 3-acetyl-4-(3-cyclopentyloxy-4-methoxy-phenyl)-3-pyrrolidine-2-carboxylic acid methyl ester (0.65 9, 1.73 mmol) in dry THF (5 mL) dropwise via a syringe pump. The resulting mixture was stirred at 0° C. for 30 minutes, then at room temperature for 1 hour. The mixture then was quenched with saturated NH$_4$Cl (15 mL) and extracted with ether (2×10 mL). The combined organic extracts were dried over Na$_2$SO$_4$, and concentrated. The residue was purified by flash chromatography (silica gel, 20% ethyl acetate-hexanes, then 50%) to produce the named product as an orange oil (0.37 g, 55% yield). $^1$H NMR (300 MHz, CDCl$_3$) δ(ppm): 6.83–6.77 (m, 3H, aromatic), 4.75–4.74 (br, m, 1H), 3.83 (s, 3H, OCH$_3$), 3.96–3.50 (m, 4H), 3.73 (s, 3H, OCH$_3$), 3.37–3.25 (m, 1H), 1.96–1.59 (m, 8H, cyclopentyl), 1.22 (s, 3H, CH$_3$), 1.07 (S, 6H, CH$_3$)

EXAMPLE 8

The following illustrates the enantiomers of Intermediate 7, and the diastereomeric carbinols that result from reduction of the ketone carbonyl of Intermediate 7.

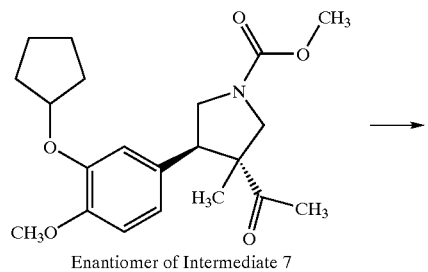

Enantiomer of Intermediate 7

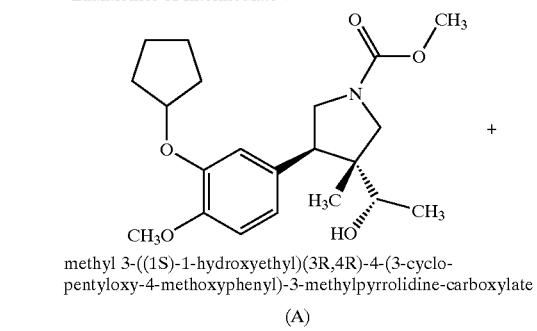

methyl 3-((1S)-1-hydroxyethyl)(3R,4R)-4-(3-cyclopentyloxy-4-methoxyphenyl)-3-methylpyrrolidine-carboxylate (A)

-continued

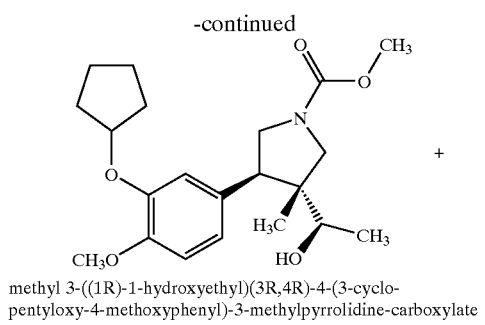

methyl 3-((1R)-1-hydroxyethyl)(3R,4R)-4-(3-cyclo-
pentyloxy-4-methoxyphenyl)-3-methylpyrrolidine-carboxylate (B)

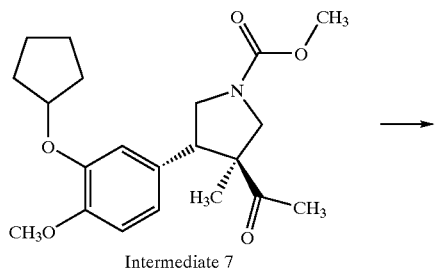

Intermediate 7

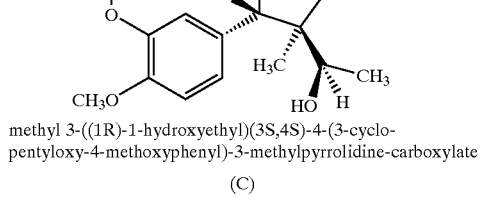

methyl 3-((1R)-1-hydroxyethyl)(3S,4S)-4-(3-cyclo-
pentyloxy-4-methoxyphenyl)-3-methylpyrrolidine-carboxylate (C)

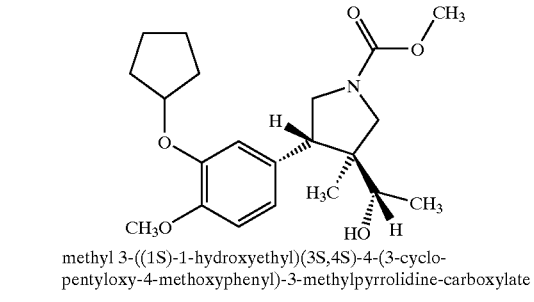

methyl 3-((1S)-1-hydroxyethyl)(3S,4S)-4-(3-cyclo-
pentyloxy-4-methoxyphenyl)-3-methylpyrrolidine-carboxylate (D)

EXAMPLE 9

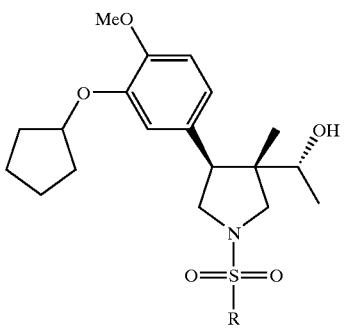

R=3-pyridyl:

3-{[3-((1R)-1-Hydroxyethyl)(3S,4S)-4-(3-cyclo-
pentyloxy-4-methoxyphenyl)-3-methylpyrrolidinyl]-
sulfonyl}pyridine Sulfonylation Procedure:

To a stirred solution of free pyrrolidine (32 mg; 0.1 mmol) in 1,4-dioxane (0.3 mL) was added, successively, aqueous potassium carbonate (0.6 mL of 0.65 M; 4 eq.) and a solution of the sulfonyl chloride (26 mg; 0.12 mmol) in 1,4-dioxane (0.3 mL) at room temperature. The resulting solution was allowed to stir at room temperature for 2 hours. The reaction was diluted with 1:1 hexanes:ethyl acetate (30 mL), washed successively with water (20 mL) and brine (20 mL), then dried over $MgSO_4$, filtered, and concentrated in vacuo to provide the sulfonamide as a slightly orange foam (36 mg; 78%).

$^1$H NMR ($CDCl_3$, 400 MHz): δ9.11 (d, 1H, J=2.2 Hz), 8.83 (dd, 1H, J=1.6, 4.8 Hz), 8.17 (ddd, 1H, J=1.5, 2.4, 8.1 Hz), 7.50 (ddd, 1H, J=0.8, 4.9, 8.0 Hz), 6.74 (d, 1H, J=8.5 Hz), 6.68 (d, 1H, J=2.1 Hz), 6.62 (dd, 1H, J=2.1, 8.3 Hz), 4.70 (c, 1H), 3.80 (s, 3H), 3.66–3.62 (m, 2H), 3.51–3.43 (m, 3H), 3.24 (d, 1H, J=13.3 Hz), 1.91–1.62 (m, 6H), 1.60–1.55 (m, 2H), 1.08 (d, 3H, J=6.4 Hz), 0.62 (s, 3H).

LRMS (Electrospray, positive): Da/e 461.2 (m+1).

EXAMPLES 10–22

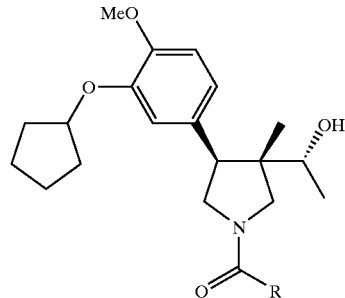

EXAMPLE 10

R=$CH_2OCH_2Ph$

1-[3-((1R)-1-Hydroxyethyl)(3S,4S)-4-(3-cyclo-
pentyloxy-4-methoxyphenyl)-3-methylpyrrolidinyl]-
2-(phenylmethoxy)ethan-1-one Acylation Procedure:

To a stirred solution of free pyrrolidine (42.6 mg; 0.13 mmol) in 1,4-dioxane (0.4 mL) was added, successively, aqueous potassium carbonate (0.8 mL of 0.65 M; 4 eq.) and a solution of the acid chloride (21 μL; 0.13 mmol) in 1,4-dioxane (0.4 mL) at room temperature. The resulting solution was allowed to stir at room temperature for 4 hours. The reaction was diluted with ethyl acetate (30 mL), washed successively with water (20 mL) and brine (20 mL), then dried over $MGSO_4$, filtered, and concentrated in vacuo to provide the amide as a slightly tan foam (46.5 mg; 99%).

$^1$H NMR ($CDCl_3$, 400 MHz, mixture of rotomers): δ7.40–7.31 (m, 5H), 6.80–6.72 (m, 3H), 4.73 (c, 1H), 4.67 (s, 2H), 4.14 (s, 2H), 3.82 (s, 3H), 3.79–3.45 (m, 5H), 3.22 (d, 1H), 1.92–1.80 (c, 6H), 1.61–1.55 (c, 2H), 1.14 (dd, 3H), 0.73 (d, 3H).

LRMS (Electrospray, positive): Da/e 468.4 (m+1).

EXAMPLE 11
R=CH$_2$OH

1-[3-((1R)-1-hydroxyethyl)(3S,4S)-4-(3-cyclo-
pentyloxy-4-methoxyphenyl)-3-methylpyrrolidinyl]-
2-hydroxyethan-1-one Hydrogenation Procedure:

A stirred solution of the O-benzyl amide (35 mg; 75 mmol) in 95% ethanol (1 mL) was treated with Pearlman's catalyst (palladium acetate, 10 mg), then placed under an atmosphere of hydrogen (1 atm). After stirring at room temperature for 24 hours, the reaction was filtered through GF/F filter paper with suction on a Buchner funnel and washed with 20 mL of 95% ethanol. Concentration of the filtrate provided the free alcohol (24 mg, 84%).

$^1$H NMR (CD3OD, 400 MHz, mixture of rotomers): δ6.91–6.82 (m, 3H), 4.83 (c, 1H), 4.22 (c, 1H), 3.87–3.22 (m, 11H), 1.93–1.73 (m, 6H), 1.69–1.59 (m, 2H), 1.11 (dd, 3H), 0.75 (br s, 3H).

LRMS (Electrospray, positive): Da/e 378.4 (m+1).

EXAMPLE 12
R=CH$_2$CH$_2$N (H) CO$_2$CH$_2$Ph

N-{3-[3-((1R)-1-Hydroxyethyl)(3S,4S)-4-(3-cyclo-
pentyloxy-4-methoxyphenyl)-3-methylpyrrolidinyl]-
3-oxopropyl}(phenylmethoxy)carboxamide Prepared via the acylation procedure. The p-nitrophenylester of N-Cbz-β-alanine was used in place of the acid chloride.

$^1$H NMR (CDCl$_3$, 400 MHz, mixture of rotomers): δ7.38–7.28 (m, 5H), 6.92–6.83 (m, 3H), 5.06 (c, 2H), 4.86 (s, 2H), 4.84 (c, 1H), 3.81–3.27 (m, 10H), 2.59 (c, 2H), 1.98–1.69 (c, 6H), 1.64–1.57 (c, 2H), 1.09 (d, 3H), 0.73 (d, 3H).

LRMS (Electrospray, positive): Da/e 525.3 (m+1).

EXAMPLE 13
R=CH$_2$CH$_2$NH$_2$

1-[3-((1R)-1-Hydroxyethyl)(3S,4S)-4-(3-cyclo-
pentyloxy-4-methoxyphenyl)-3-methylpyrrolidinyl]-
3-aminopropan-1-one Prepared via the hydrogenation procedure.

$^1$H NMR (CD$_3$OD, 400 MHz, mixture of rotomers): δ6.91–6.79 (m, 3H), 4.81 (c, 1H), 3.92–3.29 (m, 11H), 3.01 (br s, 2H), 2.61–2.58 (m, 2H), 1.95–1.73 (m, 6H), 1.68–1.58 (m, 2H), 1.10 (dd, 3H), 0.76 (d, 3H)

LRMS (Electrospray, positive) : Da/e 391.4 (m+1).

EXAMPLE 14
R=CH$_2$CH$_2$CO$_2$CH$_2$Ph

Phenylmethyl 4-[3-((1R)-1-hydroxyethyl)(3S,4S)-4-
(3-cyclopentyloxy-4-methoxyphenyl)-3-
methylpyrroli-dinyl]-4-oxobutanoate Prepared via the acylation procedure.

$^1$H NMR (CDCl$_3$, 400 MHz, mixture of rotomers): δ7.41–7.31 (m, 5H), 6.84–6.75 (m, 3H), 5.14 (d, 2H), 4.74 (c, 1H), 3.94–3.44 (m, 8H), 3.27 (d, 1H), 2.80–2.73 (m, 2H), 2.67–2.58 (m, 2H), 1.96–1.81 (m, 6H), 1.68–1.56 (m, 2H), 1.15 (dd, 3H), 0.75 (d, 3H).

LRMS (Electrospray, positive): Da/e 510.3 (m+1).

EXAMPLE 15
R=CH$_2$CH$_2$CO$_2$H

4-[3-((1R)-1-Hydroxyethyl)(3S,4S)-4-(3-
cyclopentyl-oxy-4-methoxyphenyl)-3-
methylpyrrolidinyl]-4-oxo-butanoic Acid Prepared via the hydrogenation procedure.

$^1$H NMR (CDCl$_3$, 400 MHz, mixture of rotomers) δ6.80–6.72 (m, 3H), 4.74 (c, 1H), 3.98–3.54 (m, 10H), 3.40 (d, 1H), 3.24 (d, 1H), 2.69 (c, 2H), 1.95–1.74 (m, 6H), 1.69–1.51 (m, 2H), 1.14 (dd, 3H), 0.74 (d, 3H).

LRMS (Electrospray, positive): Da/e 420.3 (m+1).

EXAMPLE 16
R=CH$_2$N (H) CO$_2$CH$_2$Ph

N-{2-[3-((1R)-1-Hydroxyethyl)(3S,4S)-4-(3-cyclo-
pentyloxy-4-methoxyphenyl)-3-methylpyrrolidinyl]-
2-oxoethyl}(phenylmethoxy)carboxamide Prepared via the acylation procedure. The p-nitrophenylester of N-Cbz-glycine was used in place of the acid chloride.

$^1$H NMR (CDCl$_3$, 400 MHz, mixture of rotomers): δ7.40–7.25 (m, 5H), 6.92–6.81 (m, 3H), 5.11 (s, 2H), 4.87 (s, 2H), 4.82 (c, 1H), 4.11–3.28 (m, 9H), 1.95–1.70 (m, 6H), 1.65–1.55 (m, 2H), 1.10 (br s, 3H), 0.76 (br s, 3H).

LRMS (Electrospray, positive): Da/e 511.6 (m+1).

EXAMPLE 17
R=CH$_2$NH$_2$

1-[3-((1R)-1-Hydroxyethyl)(3S,4S)-4-(3-cyclo-
pentyloxy-4-methoxyphenyl)-3-methylpyrrolidinyl]-
2-aminoethan-1-one Prepared via the hydrogenation procedure.

$^1$H NMR (CD$_3$OD, 400 MHz, mixture of rotomers): δ6.91–6.82 (m, 3H), 4.80 (c, 1H), 3.91–3.28 (m, 11H), 1.90–1.75 (m, 6H), 1.66–1.57 (m, 2H), 1.09 (dd, 3H), 0.74 (d, 3H).

LRMS (Electrospray, positive): Da/e 377.2 (m+1).

EXAMPLE 18
R=CO$_2$CH$_3$

Methyl 2-[3-((1R)-1-hydroxyethyl)(3S,4S)-4-(3-
indan-2-yloxy-4-methoxyphenyl)-3-
methylpyrrolidinyl]-2-oxoacetate Prepared via the Hunig's base coupliIng procedure.

$^1$H NMR (CDCl$_3$, 400 MHz, mixture of rotomers) δ6.82–6.75 (m, 3H), 4.74 (c, 1H), 4.01 (d, 1H), 3.98–3.56 (m, 10H), 3.50 (dd, 1H), 1.93–1.84 (m, 6H) 1.64–1.56 (m, 2H), 1.45 (dd, 1H), 1.16 (dd, 3H), 0.79 (s, 1.5H), 0.75 (s, 1.5H).

LRMS (Electrospray, positive): Da/e 406.2 (m+1).

EXAMPLE 19
R=4-Methyl-piperazine 3-((1R)-1-Hydroxyethyl)(3S,4S)-4-(3-
cyclopentyloxy-4-methoxyphenyl)-3-
methylpyrrolidinyl-4-methyl-piperazinyl Ketone Prepared via the CDI (carbonyl diimdazole) coupling procedure.

$^1$H NMR (CDCl$_3$, 400 MHz, mixture of rotomers): δ6.83–6.78 (m, 3H), 4.76 (c, 1H), 4.06–3.77 (m, 18H), 3.61 (q, 1H), 3.39 (br s, 1H), 1.93–1.78 (m, 6H), 1.63–1.57 (m, 2H), 1.15 (br s, 3H), 0.81 (br s, 3H).

LRMS (Electrospray, positive): Da/e 446.4 (m+1).

EXAMPLE 20
R=Morpholine 3-((1R)-1-Hydroxyethyl)(3S,4S)-4-(3-cyclopentyloxy-4-methoxyphenyl)-3-methylpyrrolidinyl-morpholin-4-yl ketone Prepared via the CDI coupling procedure.

$^1$H NMR (CDCl$_3$, 400 MHz, mixture of rotomers): δ6.84–6.77 (m, 3H), 4.76 (c, 1H), 3.88–3.52 (m, 12H), 3.41 (dd, 1H), 3.38 (dd, 1H), 3.28 (dd, 1H), 3.25 (dd, 1H), 3.10 (d, 1H), 1.95–1.81 (m, 6H), 1.62–1.54 (m, 2H), 1.15 (d, 3H), 0.75 (s, 3H).

LRMS (Electrospray, positive): Da/e 433.3 (m+1).

EXAMPLE 21
R=CH$_2$O-Menthol

1-[3-((1S)-1-Hydroxyethyl)(3S,4S)-4-(3-cyclopentyloxy-4-methoxyphenyl)-3-methylpyrrolidinyl]-2-[(2S,1R,5R)-5-methyl-2-(methylethyl)cyclohexyloxy]-ethan-1-one Other Carbinol Diastereomer Prepared via the Hunig's base mediated acylation procedure.

$^1$H NMR (CDCl$_3$, 400 MHz, mixture of rotomers): δ6.82–6.75 (m, 3H), 4.74 (c, 1H), 4.19 (dd, 1H), 4.04 (dd, 1H), 3.92–3.76 (m, 5H), 3.47–3.19 (m, 5H), 2.26 (c, 1H) 2.13 (c, 1H), 1.94–1.80 (m, 6H), 1.65–1.53 (m, 4H), 1.51–1.19 (m, 4H), 1.14 (d, 3H), 0.95–0.84 (m, 9H), 0.79 (d, 3H).

LRMS (Electrospray, positive): Da/e 516.3 (m+1).

EXAMPLE 22
R=4-(2-Methylthiazole)

3-((1R)-1-Hydroxyethyl)(3S,4S)-4-(3-cyclopentyloxy-4-methoxyphenyl)-3-methylpyrrolidinyl 2-methyl (1,3-thiazol-4-ylketone Prepared via the EDCI coupling procedure.

$^1$H NMR (CD$_3$OD, 400 MHz, mixture of rotomers) : δ7.98 (dd, 1H), 6.92–6.82 (m, 3H), 4.84 (c, 1H), 4.27 (t, 0.5H), 4.16 (t, 0.5H), 4.08 (t, 0.5H), 3.96 (d, 0.5H), 3.85–3.47 (m, 7H), 2.72 (dd, 3H), 1.88–1.72 (m, 6H), 1.68–1.56 (m, 2H), 1.14 (dd, 1.5H), 1.08 (dd, 1.5H), 0.82 (d, 1.5H), 0.73 (d, 1.5H)

LRMS (Electrospray, positive): Da/e 445.4 (m+1).

EXAMPLES 23-29

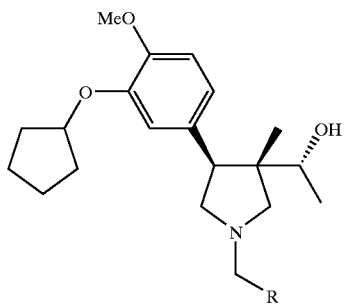

EXAMPLE 23
R=2-Pyridyl (1R)-1-[(3S,4S)-4-(3-Cyclopentyloxy-4-methoxyphenyl)-3-methyl-1-(2-pyridylmethyl)pyrrolidin-3-yl]ethan-1-ol Reductive Amination Procedure:

To a stirred solution of free pyrrolidine (32 mg; 0.1 mmol) and pyridine 2-carboxaldehyde (10 mL; 0.1 mmol) in dry 1,2-dichloroethane (0.3 mL) was added sodium triacetoxyborohydride (30 mg; 0.14 mmol) under a nitrogen atmosphere at room temperature. After stirring for 3 hours, the reaction was quenched with saturated aqueous sodium bicarbonate (0.1 mL) and stirred for 5 minutes. The reaction was diluted with ethyl acetate (20 mL), washed with saturated aqueous sodium bicarbonate (20 mL) and brine (20 mL), then dried over MgSo$_4$, filtered, and concentrated in vacuo to provide the N-alkylated product as a yellow oil (40.4 mg; 98%).

$^1$H NMR (CDCl$_3$, 400 MHz): δ8.54 (ddd, 1H), 7.68 (dt, 1H), 7.43 (d, 1H), 7.18 (ddd, 1H), 6.79–6.73 (m, 3H), 4.75 (c, 1H), 3.89–3.77 (m, 5H), 3.69 (q, 1H), 3.59 (t, 1H), 3.33 (t, 1H), 3.16 (d, 1H), 2.70 (t, 1H), 2.21 (d, 1H), 1.92–1.80 (m, 6H), 1.64–1.57 (m, 2H), 1.14 (d, 3H), 0.50, 3H).

LRMS (Electrospray, positive): Da/e 411.4 (m+1).

EXAMPLE 24
R=3-pyridyl (1R)-1-[(3S,4S)-4-(3-Cyclopentyloxy-4-methoxyphenyl)-3-methyl-1-(3-pyridylmethyl)pyrrolidin-3-yl]ethan-1-ol Prepared via the reductive amination procedure.

$^1$H NMR (CDCl$_3$, 400 MHz): δ8.54 (d, 1H), 8.51 (dd, 1H), 7.68 (d, 1H), 7.26 (dd, 1H), 6.78–6.71 (m, 3H), 4.74 (c, 1H), 3.86–3.78 (m, 4H), 3.68 (q, 1H), 3.64 (d, 1H), 3.53 (t, 1H), 3.22 (t, 1H), 3.05 (d, 1H), 2.62 (t, 1H), 2.14 (d, 1H), 1.92–1.78 (m, 6H), 1.64–1.56 (m, 2H), 1.12 (d, 3H), 0.50 (s, 3H).

LRMS (Electrospray, positive): Da/e 411.4 (m+1).

EXAMPLE 25
R=4-pyridyl (1R)-1-[(3S,4S)-4-(3-Cyclopentyloxy-4-methoxyphenyl)-3-methyl-1-(4-pyridylmethyl)pyrrolidin-3-yl]ethan-1-ol Prepared via the reductive amination procedure.

$^1$H NMR (CDCl$_3$, 400 MHz): δ8.54 (d, 2H), 7.27 (d, 2H), 6.79–6.72 (m, 3H), 4.74 (c, 1H), 3.86–3.74 (m, 4H), 3.70 (q, 1H), 3.64 (d, 1H), 3.55 (t, 1H), 3.23 (t, 1H), 3.06 (d, 1H), 2.64 (t, 1H), 2.15 (d, 1H), 1.92–1.80 (m, 6H), 1.65–1.58 (m, 2H), 1.14 (d, 3H) 0.52 (s, 3H).

LRMS (Electrospray, positive): Da/e 411.4 (m+1).

EXAMPLE 26
R=CH$_2$CO$_2$CH$_2$Ph

Phenylmethyl 3-[3-((1R)-1-hydroxyethyl)(3S,4S)-4-(3-cyclopentyloxy-4-methoxyphenyl)-3-methyl pyrrol-idinyl]propanoate To a stirred solution of benzyl acrylate (19.4 mg; 0.12 mmol) in dry dimethylformamide (0.1 mL) was added the free pyrrolidine (12.8 mg; 0.04 mmol) and powdered potassium carbonate (26.5 mg; 0.18 mmol) under a nitrogen atmosphere. The resulting mixture was stirred at 80° C. for 16 hours, then allowed to cool to room temperature. The reaction was diluted with dichloromethane (20 mL), washed with water, saturated aqueous sodium bicarbonate, and brine, then dried over $Na_2SO_4$, filtered, and concentrated in vacuo. The residue was purified via flash chromatography (2:1 ethyl acetate:hexanes on silica gel) to provide the ester (11.7 mg; 60%).

$^1$H NMR (CDCl$_3$, 400 MHz): δ7.37–7.31 (m, 5H), 6.81–6.72 (m, 3H), 5.14 (q, 2H), 4.76 (c, 1H), 3.87–3.81 (m, 4H), 3.65 (q, 1H), 3.54 (t, 1H), 3.31 (t, 1H), 3.15 (d, 1H), 2.82 (dt, 2H), 2.62–2.54 (m, 3H), 2.08 (d, 1H), 1.91–1.81 (m, 6H), 1.66–1.56 (m, 2H), 1.15 (d, 3H), 0.48 (s, 3H).

LRMS (Electrospray, positive): Da/e 482.3 (m+1).

EXAMPLE 27

R=CH$_2$CO$_2$H

3-[3-((1R)-1-Hydroxyethyl)(3S,4S)-4-(3-cyclopentyl-oxy-4-methoxyphenyl)-3-methylpyrrolidinyl]propanoic Acid Prepared via the hydrogenation procedure.

$^1$H NMR (CDCl$_3$, 400 MHz): δ6.82–6.71 (m, 3H), 4.80 (c, 1H), 4.06–3.15 (m, 11H), 2.73 (br s, 2H), 1.91–1.74 (m, 6H), 1.63–1.53 (m, 2H), 1.14 (d, 3H), 0.68 (s, 3H).

EXAMPLE 28

R=CO$_2$CH$_2$Ph

Phenylmethyl 2-[3-((1R)-1-hydroxyethyl)(3S,4S)-4-(3-cyclopentyloxy-4-methoxyphenyl)-3-methylpyrroli-dinyl]acetate Prepared via the Hunig's base mediated coupling procedure.

$^1$H NMR (CDCl$_3$, 400 MHz): δ7.41–7.32 (m, 5H), 6.82–6.73 (m, 3H), 5.18 (q, 2H), 4.77 (c, 1H), 3.82 (s, 3H), 3.68 (q, 1H), 3.59 (t, 1H), 3.52 (d, 1H), 3.36–3.30 (m, 2H), 3.24 (d, 1H), 2.88 (t, 1H), 2.31 (d, 1H), 1.93–1.80 (m, 6H), 1.65–1.56 (m, 2H), 1.16 (d, 3H), 0.53 (s, 3H).

LRMS (Electrospray, positive): Da/e 468.3 (m+1).

EXAMPLE 29

R=CO$_2$H

2-[3-((1R)-1-Hydroxyethyl)(3S,4S)-4-(3-cyclopentyloxy-4-methoxyphenyl)-3-methylpyrroli-dinyl]acetic Acid Prepared via hydrogenation procedure from IC-862.

$^1$H NMR (CDCl$_3$, 400 MHz): δ6.77–6.68 (m, 3H), 5.56 (br s, 1H), 4.77 (c, 1H), 3.99–3.85 (m, 4H), 3.82–3.59 (m, 7H), 2.88 (br s, 1H), 1.91–1.75 (m, 6H), 1.59–1.51 (m, 2H), 11.1 (d, 3H), 0.67 (s, 3H).

LRMS (Electrospray, negative): Da/e 376.2 (m-1).

EXAMPLES 30 & 31

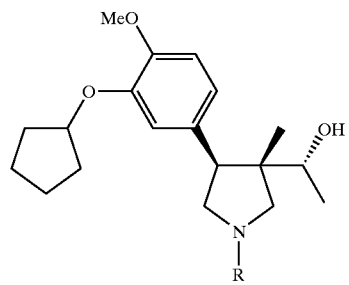

EXAMPLE 30

R=2-Pyridyl (1R)-1-[(3S,4S)-4-(3-Cylcopentyloxy-4-methoxy-phenyl)-3-methyl-1-(2-pyridyl)pyrrolidin-3-yl]ethan-1-ol Prepared via the aryl bromide coupling procedure.

$^1$H NMR (CDCl$_3$, 400 MHz): δ8.18 (ddd, 1H), 7.46 (ddd, 1H), 6.89–6.82 (m, 3H), 6.54 (ddd, 1H), 6.40 (d, 1H), 4.75 (c, 1H), 3.92–3.65 (m, 8H), 3.36 (d, 1H), 1.94–1.80 (m, 6H), 1.66–1.55 (m, 2H).

LRMS (Electrospray, positive): Da/e 397.4 (m +1).

EXAMPLE 31

R=3-Pyridyl (1R)-1-[(3S,4S)-4-(3-Cyclopentyloxy-4-methoxy-phenyl)-3-methyl-1-(3-pyridyl)pyrrolidin-3-yl]ethan-1-ol Prepared via the Buchwald coupling procedure.

$^1$H NMR (CDCl$_3$, 400 MHz): δ8.00 (d, 1H), 7.93 (d, 1H), 7.12 (dd, 1H), 6.86–6.78 (m, 4H), 4.73 (c, 1H), 3.85–3.59 (m, 8H), 3.12 (d, 1H), 1.90–1.79 (m, 6H), 1.60–1.54 (m, 2H), 1.22 (d, 3H), 0.82 (s, 3H).

LRMS (Electrospray, positive): Da/e 397.2 (m +1).

EXAMPLES 32–40

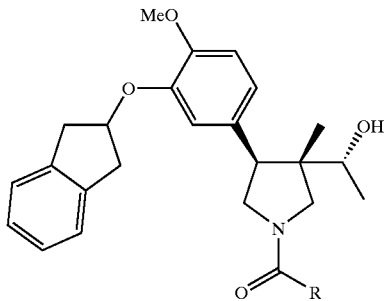

EXAMPLE 32

R=C(CH$_3$)$_2$N(H)CO$_2$CH$_2$Ph

N-{2-[3-((1R)-1-Hydroxyethyl)(3S,4S)-4-(3-indan-2-yloxy-4-methoxyphenyl)-3-methylpyrrolidinyl]-1,1-dimethyl-2-oxoethyl}(phenylmethoxy)carboxamide PyBrOP Coupling Procedure:

To a stirred solution of bromo-tris-pyrrolidino-phosphonium hexafluorophosphate (PyBrOP; 70 mg; 0.15 mmol), N-carbobenzyloxy-2-methylalanine (35.5 mg; 0.15 mmol), and Hunig's base (78 μL; 0.45 mmol) in dry dimethylformamide (1 mL) was added the free pyrrolidine (50 mg; 0.14 mmol) at room temperature under a nitrogen atmosphere. The resulting solution was stirred at room temperature for 16 hours, then was heated to 70° C. for 5 hours. The reaction was allowed to cool to room temperature and was concentrated in vacuo. The residue was purified via radial chromatography (1 mm chromatotron plate with 3% methanol in dichloromethane) to provide the amide as a white foam (20 mg; 24%).

$^1$H NMR (CDCl$_3$, 400 MHz, mixture of rotomers): δ7.43–7.15 (m, 9H), 6.82–6.62 (m, 3H), 5.64 (br s, 0.5H), 5.51 (br s, 0.5H), 5.15–5.08 (m, 3H), 3.97–3.15 (m, 13H), 1.58 (br s, 6H), 1.13 (br d, 3H), 0.68 (br s, 3H).

LRMS (Electrospray, positive): Da/e 604.9 (m+18).

EXAMPLE 33
R=C(CH$_3$)$_2$NH$_2$

1-[3-((1R)-1-Hydroxyethyl)(3S,4S)-4-(3-indan-2-yloxy-4-methoxyphenyl)-3-methylpyrrolidinyl]-2-amino-2-methylpropan-1-one Prepared via the hydrogenation procedure.

$^1$H NMR (CD$_3$OD, 400 MHz, mixture of rotomers): δ7.21–7.16 (m, 2H), 7.15–7.12 (m, 2H), 6.94–6.87 (m, 3H), 5.22 (c, 1H), 4.05 (d, 1H), 3.88 (c, 1H), 3.77–3.69 (m, 4H), 3.60–3.52 (c, 2H), 3.40–3.29 (c, 2H), 3.22 (q, 1H), 3.13–3.09 (c, 2H), 1.37 (d, 6H), 1.13 (br s, 3H) 0.80 (s, 3H)

LRMS (Electrospray, positive): Da/e 453.5 (m+1).

EXAMPLE 34
R=CH$_2$OCH$_2$Ph

1-[3-((1R)-1-Hydroxyethyl)(3S,4S)-4-(3-indan-2-yloxy-4-methoxyphenyl)-3-methylpyrrolidinyl]-2-(phenylmethoxy)ethan-1-one Hunig's Base Coupling Procedure:

To a stirred solution of free pyrrolidine (50 mg; 0.14 mmol) and Hunig's base (35.5 μL; 0.20 mmol) in dry dichloromethane (1 mL) was added the benzyloxy acetyl chloride (22.5 μL; 0.14 mmol) via syringe at room temperature under a nitrogen atmosphere. After stirring for 1 hour, the reaction was diluted with dichloromethane (30 mL), washed successively with 1 N aqueous hydrochloric acid (2×10 mL) and brine (10 mL), then dried over Na$_2$SO$_4$, filtered, and concentrated in vacuo. The residue was purified via radial chromatography (1 mm chromatotron plate with 3% methanol in dichloromethane) to provide the amide as a clear oil (48 mg; 68%).

$^1$H NMR (CDCl$_3$, 400 MHz, mixture of rotomers): δ7.41–7.16 (m, 9H), 6.84–6.79 (m, 3H), 5.17 (c, 1H), 4.66 (d, 2H), 4.19–4.11 (m, 2H), 3.96 (dd, 0.5H), 3.83–3.54 (m, 7H), 3.47 (d, 0.5H), 3.38–3.29 (m, 2H), 3.24–3.17 (m, 3H), 1.57 (br t, 1H), 1.15 (dd, 3H), 0.75 (s, 3H)

LRMS (Electrospray, positive): Da/e 516.8 (m+1).

EXAMPLE 35
R=CH$_2$OH

1-[3-((1R)-1-Hydroxyethyl)(3S,4S)-4-(3-indan-2-yloxy-4-methoxyphenyl)-3-methylpyrrolidinyl]-2-hydroxyethan-1-one Prepared via the hydrogenation procedure.

$^1$H NMR (CD$_3$OD, 400 MHz, mixture of rotomers): δ7.24–7.18 (m, 2H), 7.14–7.12 (m, 2H), 6.92–6.86 (m, 3H), 5.20 (c, 1H), 4.27–4.14 (m, 2H), 3.90–3.50 (m, 6H), 3.41 (d, 1H), 3.34–3.24 (m, 4H), 3.13–3.08 (m, 2H), 1.12 (dd, 3H), 0.77 (br s, 3H).

LRMS (Electrospray, positive): Da/e 426.5 (m+1).

EXAMPLE 36
R=CH$_2$C(CH$_3$)2CO$_2$H

4-[3-((1R)-1-Hydroxyethyl)(3S,4S)-4-(3-indan-2-yloxy-4-methoxyphenyl)-3-methylpyrrolidinyl]-2,2-dimethyl-4-oxobutanoic Acid A thick walled glass tube fitted with a threaded cap was charged with the free pyrrolidine (20 mg; 0.05 mmol) and the 2,2-dimethylsuccinic anhydride (25.8 mg; 0.05 mmol). The tube was sealed and heated to 150° C. for 30 minutes. The reaction mixture was allowed to cool to room temperature to provide the named amide (containing ~15–20% of the other regioisomer) as a brown solid (22 mg; 82%).

$^1$H NMR (CD$_3$OD, 400 MHz, mixture of rotomers): δ7.22–7.20 (m, 2H), 7.15–7.12 (m, 2H), 6.96–6.85 (m, 3H), 5.23 (c, 1H), 3.92–3.49 (m, 7H), 3.37–3.28 (m, 4H), 3.13–3.09 (m, 2H), 2.73–2.55 (m, 2H), 1.30 (br s, 6H), 1.12 (t, 3H), 0.76 (d, 3H).

LRMS (Electrospray, negative): Da/e 494.5 (m−1).

EXAMPLE 37
R=4-(2-methylthiazole)

3-((1R)-1-Hydroxyethyl)(3S,4S)-4-(3-indan-2-yloxy-4-methoxyphenyl)-3-methylpyrrolidinyl 2-methyl(1,3-thiazol-4-yl) ketone EDCI Coupling Procedure:

To a stirred solution of 1-(3-dimethyl-aminopropyl)-3-ethylcarbodiimide hydrochloride (42.3 mg; 0.214 mmol) in dry dichloromethane (1 mL) was added the thiazole carboxylic acid (30.7 mg; 0.214 mmol) at room temperature under a nitrogen atmosphere. The resulting bright red mixture was allowed to stir for 1 hour, then the free pyrrolidine (75 mg; 0.204 mmol) was added in one portion. After stirring at room temperature overnight, the reaction was concentrated at reduced pressure, and the residue purified via radial chromatography (1 mm chromatotron plate with 3% methanol in dichloromethane) to provide the named amide as a clear film (21 mg; 20%).

$^1$H NMR (CDCl$_3$, 400 MHz; mixture of rotomers): δ7.91 (s, 0.5 H), 7.88 (s, 0.5 H), 7.25–7.20 (m, 2H), 7.18–7.16 (m, 2H), 6.90–6.82 (m, 3H), 5.19 (c, 1H), 4.33 (dd, 0.5 H), 4.23 (t, 0.5H), 4.15 (d, 0.5 H), 4.10 (dd, 0.5H), 3.99 (t, 0.5H), 3.85 (d, 0.5H), 3.81 (s, 3H), 3.77–3.58 (m, 3H), 3.38–3.31 (m, 2H), 3.24–3.20 (m, 2H), 2.74 (s, 1.5H), 2.71 (s, 1.5H), 1.93 (s, 0.5H), 1.61 (d, 0.5H), 1.22 (d, 1.5H), 1.18 (d, 1.5H), 0.86 (s, 1.5H), 0.75 (s, 1.5H).

LRMS (Electrospray, positive): Da/e 493.6 (m+1).

EXAMPLE 38
R=3-Tetrahydrofuranyl 3-((1R)-1-Hydroxyethyl)(3S,4S)-4-(3-indan-2-yloxy-4-methoxyphenyl)-3-methylcyclopentyl oxolan-3-yl Ketone (Mixture of 2 Diastereomers at the Tetrahydrofuranyl Point of Attachment)

Prepared via the Hunig's base coupling procedure.

$^1$H NMR (CDCl$_3$, 400 MHz, mixture of rotomers): δ7.40–7.20 (m, 2H), 7.19–7.16 (m, 2H), 6.86–6.83 (m, 3H), 5.18 (c, 1H), 4.15–4.04 (m, 1H), 3.98–3.15 (m, 13H), 2.31–2.09 (m, 2H), 1.75 (br s, 1H), 1.26 (t, 1.5H), 1.17 (t, 1.5H), 0.80 (d, 1.5H), 0.78 (s, 1.5H).

LRMS (Electrospray, positive): Da/e 466.3 (m+1).

EXAMPLE 39
R=CH₂N(H)CO₂CH₂Ph

N-{2-[3-((1R)-1-Hydroxyethyl)(3S,4S)-4-(3-indan-2-yloxy-4-methoxyphenyl)-3-methylpyrrolidinyl]-2-oxoethyl}(phenylmethoxy)carboxamide Prepared via the Hunig's base coupling procedure.

¹H NMR (CD₃OD, 400 MHz, mixture of rotomers): δ7.35–7.20 (m, 9H), 6.91–6.88 (m, 3H), 5.22 (br s, 1H), 5.10 (s, 2H), 4.07–3.09 (m, 15H), 1.13 (t, 3H), 0.78 (s, 3H).

EXAMPLE 40
R=CH₂NH₂

1-[3-((1R)-1-Hydroxyethyl)(3S,4S)-4-(3-indan-2-yloxy-4-methoxyphenyl)-3-methylpyrrolidinyl]-2-aminoethan-1-one Prepared via the hydrogenation procedure.

¹H NMR (CDCl₃, 400 MHz, mixture of rotomers): δ7.22–7.19 (m, 2H), 7.18–7.15 (m, 2H), 6.84 (d, 1H), 6.81 (d, 2H), 5.17 (c, 1H), 3.96 (dd, 0.5H), 3.81–3.43 (m, 9H), 3.37–3.30 (m, 1.5H), 3.23–3.13 (m, 2H), 2.99 (br s, 2H), 1.15 (t, 3H), 0.75 (d, 3H).

LRMS (Electrospray, positive): Da/e 425.5(m+1).

EXAMPLES 41–43

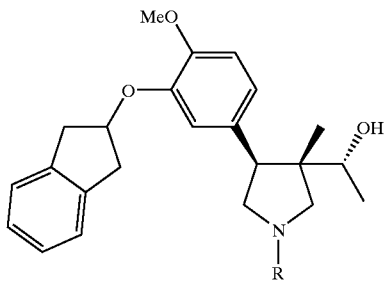

EXAMPLE 41
R=2-Pyridyl
Aryl Bromide Coupling Procedure (1R)-1-[(3S,4S)-4-(3-Indan-2-yloxy-4-methoxyphenyl)-3-methyl-1-(2-pyridyl)pyrrolidin-3-yl]ethan-1-ol To a stirred mixture of free pyrrolidine (115 mg; 0.31 mmol) and potassium carbonate (173 mg; 1.2 mmol) in dry dimethylformamide (2 mL) was added 2-bromopyridine (0.12 mL; 1.2 mmol) via syringe at room temperature under a nitrogen atmosphere. The resulting mixture was heated to 90° C., held for 22 hours, then allowed to cool back to room temperature. The reaction was diluted with water (60 mL), then extracted with ethyl acetate (3×30 mL). The combined organic extracts were washed with brine, dried over Na₂SO₄, filtered, and concentrated in vacuo. The residue was purified via flash chromatography on silica gel (100% ethyl acetate) to provide the N-pyridyl pyrrolidine (73.4 mg; 53%).

¹H NMR (CDCl₃, 400 MHz): δ8.18 (ddd, 1H), 7.45 (ddd, 1H), 7.26–7.21 (m, 2H), 7.19–7.16 (m, 2H), 6.92–6.88 (m, 2H), 6.83 (d, 1H), 6.54 (ddd, 1H) 6.40 (d, 1H), 5.17 (c, 1H), 3.86–3.78 (m, 5H), 3.70 (d, 1H), 3.67 (d, 1H), 3.38–3.30 (m, 3H).

LRMS (Electrospray, positive): Da/e 445.4 (m+1).

EXAMPLE 42
R=3-Pyridyl (1R)-1-[(3S,4S)-4-(3-Indan-2-yloxy-4-methoxyphenyl)-3-methyl-1-(3-pyridyl)pyrrolidin-3-yl]ethan-1-ol Buchwald Coupling Procedure:

To a stirred solution of free pyrrolidine (79.3 mg; 0.22 mmol) and sodium t-butoxide (29 mg; 0.31 mmol) in dry toluene (3 mL) was added, sequentially, 3-bromopyridine (22.9 μL; 0.24 mmol), tris-(dibenzylideneacetone) dipalladium (0)(3.9 mg; cat.), and (R)-(+)-1,1'-bi-2-naphthol (5.4 mg; cat.) at room temperature under a nitrogen atmosphere. The resulting mixture was heated to 80° C., held 3 hours, then allowed to cool back to room temperature. The reaction then was diluted with ethyl acetate (40 mL), washed with brine, dried over Na₂SO₄, filtered, and concentrated in vacuo. The residue was purified via flash chromatography on silica gel (40% ethyl acetate in hexanes) to provide the N-pyridyl pyrrolidine (72.1 mg; 75%).

¹H NMR (CDCl₃, 400 MHz): δ7.98 (d, 1H), 7.91 (d, 1H), 7.24–7.15 (m, 4H), 7.11 (dd, 1H), 6.90–6.82 (m, 4H), 5.15 (c, 1H), 3.81–3.72 (m, 4H), 3.70–3.62 (m, 4H), 3.35–3.11 (m, 5H), 1.24 (d, 3H), 0.84 (s, 3H)

LRMS (Electrospray, positive): Da/e 445.3 (m+1).

EXAMPLE 43
R=2-Pyrimidyl (1R)-1-[(3S,4S)-4-(3-Indan-2-yloxy-4-methoxyphenyl)-3-methyl-1-pyrimidin-2-ylpyrrolidin-3-yl]ethan-1-ol Prepared via the aryl bromide coupling procedure.

¹H NMR (CDCl₃, 400 MHz): δ8.34 (dd, 2H), 7.24–7.18 (m, 2H), 7.16 (dd, 2H), 6.94–6.84 (m, 2H), 6.82 (c, 1H), 6.48 (t, 1H), 5.16 (c, 1H), 4.12–3.75 (m, 7H), 3.64 (br d, 1H), 3.52 (d, 1H), 3.36 (d, 1H), 3.32 (d, 1H), 3.24 (t, 1H), 3.20 (t, 1H), 1.23 (d, 3H) 0.83 (s, 3H).

LRMS (Electrospray, positive): Da/e 446.4 (m +1).

EXAMPLES 44–63

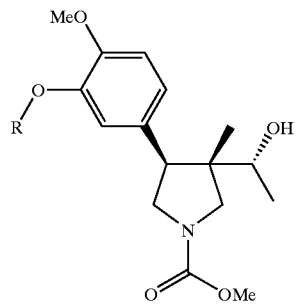

EXAMPLE 44

R=H

Methyl 3-((1R)-1-hydroxyethyl)(3S,4S)-4-(3-hydroxy-4-methoxyphenyl)-3-methylpyrrolidinecarboxylate Hunig's Base Mediated Acylation Procedure:

To a cooled (0° C.), stirred solution of free phenol-pyrrolidine (670 mg; 2.67 mmol) and Hunig's base (1.4 mL; 8.0 mmol) in dry dichloromethane (10 mL), 1,4-dioxane (5 mL), and methanol (1 mL) was added methyl chloroformate (0.41 mL; 5.3 mmol) via syringe under a nitrogen atmosphere. The resulting solution was stirred at 0° C. for 1 hour, then was diluted with dichloromethane (90 mL), washed successively with 1 N aqueous hydrochloric acid (2×20 mL) and brine (20 mL), then dried over $Na_2SO_4$, filtered, and concentrated in vacuo. The residue (737 mg) was dissolved in tetrahydrofuran (3 mL) and water (2 mL) and treated with a solution of lithium hydroxide (112 mg; 2.67 mmol in 2 mL water) at room temperature. After stirring for 4 hours, the reaction was diluted with ethyl acetate (100 mL) and washed successively with 1 N aqueous hydrochloric acid (2×50 mL), saturated aqueous sodium bicarbonate (30 mL) and brine (30 mL) then dried ($Na^2SO^4$), filtered and concentrated in vacuo. The residue was purified via radial chromatography (4 mm chromatotron plate with 3% methanol in dichloromethane) to provide the free phenol as a light tan foam (250 mg; 30%).

$^1$H NMR ($CDCl_3$, 400 MHz; mixture of rotomers): δ6.84 (d, 1H), 6.78 (d, 1H), 6.72 (dd, 1H), 5.57 (d, 1H), 3.90–3.54 (m, 1H), 3.30 (d, 0.5H), 3.20 (d, 0.5H), 1.35 (br d, 1H), 1.14 (t, 3H), 0.75 (s, 3H).

LRMS (Electrospray, negative): m/z 308.6 (m−1).

LRMS (Electrospray, positive): m/z 310.5 (m+1).

EXAMPLE 45

R=(4-PhO)—Ph

Methyl 3-((1R)-1-hydroxyethyl)(3S,4S)-4-[4-methoxy-3-(4-phenoxyphenoxy)phenyl]-3-methylpyrrolidine Carboxylate Cryptand Etherification Procedure:

To a stirred suspension of sodium hydride (16 mg of a 60% dispersion in mineral oil; 0.40 mmol) in dry anisole (2 mL) was added the free phenol (100 mg; 0.32 mmol), portionwise, over 5 minutes, with hydrogen gas evolution, at room temperature under a nitrogen atmosphere. After stirring for 30 minutes, tris[2-(2-methoxyethoxy)ethyl] amine (10 μL; 0.03 mmol), copper (I) chloride (10 mg; 0.10 mmol), and 4-bromo-biphenyl ether were added, and the resulting mixture heated to reflux for 20 hours. The anisole then was removed via vacuum distillation, the residue dissolved in ethyl acetate (25 mL), and filtered through GF/F filter paper. The filtrate then was washed with 1N aq. HCl (20 mL), dried over $Na_2SO_4$, filtered, and concentrated in vacuo. The residue was purified via radial chromatography (2 mm chromatotron silica plate with 1:1 hexanes:ethyl acetate) to provide the ether as a tan oil (40 mg; 26%).

$^1$H NMR ($CDCl_3$, 400 MHz; mixture of rotomers): δ7.30 (dd, 2H), 7.09–6.86 (m, 10H), 3.88–3.49 (m, 11H), 3.28 (d, 0.5H), 3.19 (d, 0.5H), 1.93 (br s, 0.5H), 1.83 (br s, 0.5H), 1.12 (dd, 3H), 0.71 (br s, 3H)

LRMS (Electrospray, positive): Da/e 478.2 (m+1).

EXAMPLE 46

R=(4-PhO)—Ph, Other Carbinol Diastereomer

Methyl 3-((1S)-1-hydroxyethyl)(3S, 4S)-4-[4-methoxy-3-(4-phenoxyphenoxy)phenyl]-3-methyl Pyrrolidine Carboxylate Prepared via the crypt and etherification procedure.

$^1$H NMR ($CDCl_3$, 400 MHz; mixture of rotomers): δ7.32 (t, 2H), 7.07 (dt, 1H), 7.03–6.74 (m, 9H), 3.91–3.55 (m, 9H), 3.35–3.17 (m, 3H), 2.16 (d, 0.5H), 1.38 (br s, 0.5H), 1.12 (d, 3H), 0.85 (s, 3H).

LRMS (Electrospray, positive): Da/e 478.2 (m+1).

EXAMPLE 47

R=(4-Ph)—Ph

Methyl 3-((1R)-1-hydroxyethyl)(3S, 4S)-4-[4-methoxy-3-(4-phenylphenoxy)phenyl]-3-methyl Pyrrolidine Carboxylate Prepared via the crypt and etherification procedure.

$^1$H NMR ($CDCl_3$, 400 MHz; mixture of rotomers): δ7.55 (d, 2H), 7.51 (d, 2H), 7.42 (t, 2H), 7.31 (t, 1H), 7.05 (dt, 1H), 6.98–6.92 (m, 4H), 3.87–3.54 (m, 11H), 3.29 (d, 0.5H), 3.19 (d, 0.5H), 1.64 (br s, 0.5H), 1.57 (br s, 0.5H), 1.14 (dd, 3H), 0.74 (s, 3H).

LRMS (Electrospray, positive): Da/e 462.2 (m+1).

EXAMPLE 48

R=(4-Ph)—Ph, Other Carbinol Diastereomer

Methyl 3-((1S)-1-hydroxyethyl)(3S, 4S)-4-[4-methoxy-3-(4-phenylphenoxy)phenyl]-3-methyl Pyrrolidine Carboxylate Prepared via the crypt and etherification procedure.

$^1$H NMR ($CDCl_3$, 400 MHz; mixture of rotomers): δ7.56 (d, 2H), 7.52 (dt, 2H), 7.42 (t, 2H), 7.32 (t, 1H), 7.10–6.94 (m, 5H), 3.93–3.58 (m, 9H), 3.38–3.18 (m, 3H), 1.13 (d, 3H), 0.88 (s, 3H).

LRMS (Electrospray, positive): Da/e 462.2 (m+1).

EXAMPLE 49

R=Ph

Methyl 3-((1R)-1-hydroxyethyl)(3S, 4S)-4-(4-methoxy-3-phenoxyphenyl)-3-methylpyrrolidinecarboxylate Prepared via the crypt and etherification procedure.

$^1$H NMR ($CDCl_3$, 400 MHz; mixture of rotomers): δ7.32–7.26 (m, 3H), 7.02 (t, 2H), 6.94–6.88 (m, 3H), 3.85–3.49 (m, 11H), 3.27 (d, 0.5H), 3.18 (d, 0.5H), 1.12 (t, 3H), 0.71 (s, 3H).

LRMS (Electrospray, positive): Da/e 386.3 (m+1).

EXAMPLE 50

R=Ph, Other Carbinol Diastereomer

Methyl 3-((1S)-1-hydroxyethyl)(3S, 4S)-4-(4-methoxy-3-phenoxyphenyl)-3-methylpyrrolidinecarboxylate Prepared via the crypt and etherification procedure.

$^1$H NMR ($CDCl_3$, 400 MHz; mixture of rotomers): δ7.29 (t, 2H), 7.08–6.85 (m, 6H), 3.87–3.52 (m, 9H), 3.34–3.16 (m, 3H), 1.11 (d, 3H), 0.85 (s, 3H).

LRMS (Electrospray, positive): Da/e 386.3 (m+1).

EXAMPLE 51
R=4-Fluorophenyl

Methyl 3-((1R)-1-hydroxyethyl)(3S, 4S)-4-[3-(4-fluorophenoxy)-4-methoxyphenyl]-3-methylpyrrolidinecarboxylate Prepared via the crypt and etherification procedure.

$^1$H NMR (CDCl$_3$, 400 MHz; mixture of rotomers): δ7.05–6.84 (m, 7H), 3.89–3.45 (m, 11H), 3.28 (d, 0.5H), 3.18 (d, 0.5H), 1.13 (t, 3H), 0.71 (br s, 3H).

LRMS (Electrospray, positive): Da/e 404.4 (m+1).

EXAMPLE 52
R=CH$_2$ (c-C3H5)

Methyl 3-((1R)-1-hydroxyethyl)(3S, 4S)-4-[3-(cyclo-propylmethoxy)-4-methoxyphenyl]-3-methylpyrrolidinecarboxylate Potassium Carbonate Etherification Procedure:

To a stirred mixture of the free phenol (50 mg; 0.16 mmol) and powdered potassium carbonate (24.6 mg; 0.18 mmol) in dry dimethylformamide (1 mL) was added bromomethyl cyclopropane (16.5 μL; 0.17 mmol) via syringe at room temperature under a nitrogen atmosphere. The resulting mixture was heated to 65° C., held for 24 hours, then allowed to cool back to room temperature. The reaction then was diluted with water (5 mL), and extracted with ethyl ether (3×20 mL). The combined organics were dried over MgSO$_4$, filtered, and concentrated in vacuo. The residue was purified via radial chromatography (1 mm chromatotron silica plate with 30% ethyl acetate in hexanes) to provide the ether as a clear oil (30 mg; 51%).

$^1$H NMR (CDCl$_3$, 400 MHz; mixture of rotomers) δ6.84–6.75 (m, 3H), 3.94–3.54 (m, 13H), 3.29 (d, 0.5H), 3.21 (d, 0.5H), 1.72 (br s, 0.5H), 1.65 (br s, 0.5H), 1.30 (c, 1H), 1.13 (t, 3H), 0.73 (s, 3H) 0.61 (c, 2H), 0.34 (c, 2H).

LRMS (Electrospray, positive): Da/e 364.3 (m+1).

EXAMPLE 53
R=CH$_2$(c-C3H5), Other Carbinol Diastereomer

Methyl 3-((1S)-1-hydroxyethyl)(3S, 4S)-4-[3-(cyclo-propylmethoxy)-4-methoxyphenyl]-3-methylpyrrolidinecarboxylate Prepared via the potassium carbonate etherification procedure.

$^1$H NMR (CDCl$_3$, 400 MHz; mixture of rotomers): δ6.84–6.75 (m, 3H), 3.89–3.58 (m, 11H), 3.33–3.20 (m, 3H), 1.52 (br s, 1H), 1.31 (c, 1H), 1.11 (d, 3H), 0.89 (s, 3H), 0.62 (m, 2H), 0.33 (m, 2H).

LRMS (Electrospray, positive): Da/e 364.3 (m+1).

EXAMPLE 54
R=2-thiazole

Methyl 3-((1R)-1-hydroxyethyl)(3S, 4S)-4-(4-methoxy-3-(1,3-thiazol-2-yloxy)phenyl)-3-methylpyrrolidinecarboxylate Prepared via the potassium carbonate etherification procedure.

$^1$H NMR (CDCl$_3$, 400 MHz; mixture of rotomers): δ7.24–7.12 (m, 3H), 6.96 (d, 1H), 6.75 (d, 1H), 3.89–3.52 (m, 11H), 3.29 (d, 0.5H), 3.20 (d, 0.5H), 1.74 (br s, 1H), 1.14 (t, 3H), 0.74 (s, 3H).

LRMS (Electrospray, positive): Da/e 393.2 (m+1).

EXAMPLE 55
R=2-thiazole, Other Carbinol Diastereomer

Methyl 3-((1S)-1-hydroxyethyl)(3S, 4S)-4-(4-methoxy-3-(1,3-thiazol-2-yloxy)phenyl)-3-methylpyrrolidinecarboxylate Prepared via the potassium carbonate etherification procedure.

$^1$H NMR (CDCl$_3$, 400 MHz; mixture of rotomers) δ7.17 (d, 1H), 7.16 (d, 1H), 7.11 (dd, 1H), 6.97 (d, 1H), 6.75 (d, 1H), 3.86–3.59 (m, 9H), 3.42–3.19 (m, 3H), 1.52 (br s, 1H), 1.14 (d, 3H), 0.87 (s, 3H).

LRMS (Electrospray, positive): Da/e 393.2 (m+1).

EXAMPLE 56
R=2-(N-Methyl)-benzimidazole

Methyl 3-((1R)-1-hydroxyethyl)(3S, 4S)-4-(3-benzimidazol-2-yloxy-4-methoxyphenyl)-3-methylpyrrolidinecarboxylate Prepared via the potassium carbonate etherification procedure.

$^1$H NMR (CDCl$_3$, 400 MHz; mixture of rotomers) δ7.50 (d, 1H), 7.29–7.10 (m, 5H), 6.95 (d, 1H), 3.80–3.66 (m, 13H), 3.57 (t, 1H), 3.29 (d, 0.5H), 3.20 (d, 0.5H), 2.04 (br s, 1H), 1.13 (t, 3H), 0.77 (s, 3H).

LRMS (Electrospray, positive): Da/e 440.2 (m+1).

EXAMPLE 57
R=2-(N-Methyl)-benzimidazole, Other Carbinol Diastereomer

Methyl 3-((1S)-1-hydroxyethyl)(3S, 4S)-4-(3-benzimidazol-2-yloxy-4-methoxyphenyl)-3-methylpyrrolidinecarboxylate Prepared via the potassium carbonate etherification procedure.

$^1$H NMR (CDCl$_3$, 400 MHz; mixture of rotomers) δ7.50 (d, 1H), 7.30–7.09 (m, 5H), 6.96 (d, 1H), 3.87–3.63 (m, 12H), 3.40–3.21 (m, 3H), 1.15 (d, 3H), 0.91 (s, 3H).

LRMS (Electrospray, positive): Da/e 440.2 (m+1).

EXAMPLE 58
R=CH$_2$CH$_2$CH$_2$Ph

Methyl 3-((1R)-1-hydroxyethyl)(3S, 4S)-4-[4-methoxy-3-(3-phenylpropoxy)phenyl]-3-methylpyrrolidinecarboxylate Prepared via the potassium carbonate procedure.

$^1$H NMR (CDCl$_3$, 400 MHz; mixture of rotomers): δ7.35–7.17 (m, 5H), 6.85–6.77 (m, 3H), 4.02 (dt, 2H), 3.90–3.52 (m, 11H), 3.30 (d, 0.5H), 3.21 (d, 0.5H), 2.82 (t, 2H), 2.14 (p, 2H), 1.54 (br s, 0.5H), 1.49 (br s, 0.5H), 1.13 (t, 3H), 0.72 (s, 3H).

EXAMPLE 59
R=CH$_2$CH$_2$CH$_2$Ph, Other Carbinol Diastereomer

Methyl 3-((1S)-1-hydroxyethyl)(3S, 4S)-4-[4-methoxy-3-(3-phenylpropoxy)phenyl]-3-methylpyrrolidinecarboxylate Prepared via the potassium carbonate procedure.

$^1$H NMR (CDCl$_3$, 400 MHz; mixture of rotomers): δ7.33–7.19 (m, 5H), 6.84–6.78 (m, 2H), 6.72 (br s, 1H), 4.01

(t, 2H), 3.90–3.56 (m, 9H), 3.34–3.23 (m, 3H), 2.82 (t, 2H), 2.15 (p, 2H), 1.11 (d, 3H), 0.89 (s, 3H).

EXAMPLE 60

R=CH$_2$CH$_2$CH$_2$CH$_2$Ph

Methyl 3-((1R)-1-hydroxyethyl)(3S, 4S)-4-[4-methoxy-3-(4-phenylbutoxy)phenyl]-3-methylpyrrolidinecarboxylate Prepared via the potassium carbonate procedure.

$^1$H NMR (CDCl$_3$, 400 MHz; mixture of rotomers): δ7.32–7.15 (m, 5H), 6.84–6.74 (m, 3H), 4.00 (t, 2H), 3.89–3.51 (m, 11H), 3.30 (d, 0.5H), 3.22 (d, 0.5H), 2.69 (t, 2H), 1.90–1.79 (m, 4H), 1.41 (dd, 1H), 1.13 (t, 3H), 0.73 (s, 3H)

EXAMPLE 61

R=CH$_2$CH$_2$CH$_2$CH$_2$Ph, Other Carbinol Diastereomer

Methyl 3-((1S)-1-hydroxyethyl)(3S, 4S)-4-[4-methoxy-3-(4-phenylbutoxy)phenyl]-3-methylpyrrolidinecarboxylate Prepared via the potassium carbonate procedure.

$^1$H NMR (CDCl$_3$, 400 MHz; mixture of rotomers) δ7.32–7.16 (m, 5H), 6.83–6.70 (m, 3H), 3.99 (t, 2H), 3.90–3.58 (m, 9H), 3.34–3.21 (m, 3H), 2.69 (t, 2H), 1.90–1.77 (m, 4H), 1.45 (br s, 1H), 1.12 (d, 3H), 0.90 (s, 3H).

LRMS (Electrospray, positive): Da/e 442.4 (m+1).

EXAMPLE 62

R=CH$_2$CH$_2$Ph

Methyl 3-((1R)-1-hydroxyethyl)(3S, 4S)-4-[4-methoxy-3-(2-phenylethoxy)phenyl]-3-methylpyrrolidinecarboxylate Prepared via the potassium carbonate procedure.

$^1$H NMR (CDCl$_3$, 400 MHz; mixture of rotomers) 7.39–7.23 (m, 5H), 6.84–6.78 (m, 3H),4.20 (t, 2H), 3.87–3.52 (m, 11H), 3.30 (d, 0.5H), 3.21 (d, 0.5H), 3.15 (t, 2H), 1.13 (t, 3H), 0.73 (s, 3H).

LRMS (Electrospray, positive): Da/e 414.3 (m+1).

EXAMPLE 63

R=CH$_2$CH$_2$Ph, Other Carbinol Diastereomer

Methyl 3-((1S)-1-hydroxyethyl) (3S, 4S)-4-[4-methoxy-3-(2-phenylethoxy)phenyl]-3-methylpyrrolidinecarboxylate Prepared via the potassium carbonate procedure.

$^1$H NMR (CDCl$_3$, 400 MHz; mixture of rotomers): δ7.34–7.24 (m, 5H), 6.83 (d, 1H), 6.79 (dd, 1H), 6.73 (br s, 1H), 4.18 (t, 2H), 3.89–3.56 (m, 9H), 3.31–3.20 (m, 3H), 3.15 (t, 2H), 1.11 (d, 3H), 0.89 (s, 3H).

The compounds of structural formula (II) were tested for an ability to inhibit PDE4. The ability of a compound to inhibit PDE4 activity is related to the IC$_{50}$ value for the compound, i.e., the concentration of inhibitor required for 50% inhibition of enzyme activity. The IC$_{50}$ value for compounds of structural formula (II) were determined using recombinant human PDE4.

The compounds of the present invention typically exhibit an IC$_{50}$ value against recombinant human PDE4 of less than about 50 μM, and preferably less than about 25 μM, and more preferably less than about 15 μm. The compounds of the present invention typically exhibit an IC$_{50}$ value against recombinant human PDE4 of less than about 1 μM, and often less than about 0.05 μM. To achieve the full advantage of the present invention, a present PDE4 inhibitor has an IC$_{50}$ of about 700 pM (picomolar) to about 15 μM.

The IC$_{50}$ values for the compounds were determined from concentration-response curves typically using concentrations ranging from 0.1 pM to 500 μM. Tests against other PDE enzymes using standard methodology, as described in Loughney et al., *J. Biol. Chem.*, 271, pp. 796–806 (1996), also showed that compounds of the present invention are highly selective for the cAMP-specific PDE4 enzyme.

In particular, a compound of the present invention, i.e., Example 8(C), has an ICvs. human recombinant PDE4B of 0.015 μM, but has an IC$_{50}$ vs. PDE1A of 80 μM, vs. PDE1B of 100 μM, vs. PDE1C of 12 μM, vs. PDE2 of 450 μM, vs. PDE3A of 40 μM, vs. PDE5 of 270 μM, and vs. PDE7 of 36 μM. This illustrates the selectivity of the present compound with respect to inhibiting PDE4.

The compounds of structural formula (II) also were tested for an ability to reduce TNFα secretion in human peripheral blood lymphocytes. The ability to reduce TNFα secretion is related to the EC$_{50}$ values (i.e., the effective concentration of the compound capable of inhibiting 50% of the total TNFα).

The compounds of the present invention typically exhibit an EC$_{50}$ value of less than about 50 μM, and preferably less than about 25 μM, and more preferably less than about 15 μM. The compounds of the present invention typically exhibit a PBL/TNFα EC$_{50}$ value of less than about 1 μM, and often less than about 0.05 μM. To achieve the full advantage of the present invention, a present PDE4 inhibitor has an EC$_{50}$ value of about 1000 pM (picomolar) to about 20 μM.

The production of recombinant human PDEs and the IC$_{50}$ and EC$_{50}$ determinations can be accomplished by well-known methods in the art. Exemplary methods are described as follows:

Expression of Human PDEs

Expression in Baculovirus-Infected *Spodoptera fugiperda* (Sf9) Cells

Baculovirus transfer plasmids were constructed using either pBlueBacIII (Invitrogen) or pFastBac (BRL-Gibco). The structure of all plasmids was verified by sequencing across the vector junctions and by fully sequencing all regions generated by PCR. Plasmid pBB-PDE1A3/6 contained the complete open reading frame of PDE1A3 (Loughney et al., *J. Biol. Chem.*, 271, pp. 796–806 (1996)) in pBlueBacIII. Plasmid Hcam3aBB contained the complete open reading frame of PDE1C3 (Loughney et al. (1996)) in pBlueBacIII. Plasmid pBB-PDE3A contained the complete open reading frame of PDE3A (Meacci et al., *Proc. Natl. Acad. Sci., USA,* 89, pp. 3721–3725 (1992)) in pBlueBacIII.

Recombinant virus stocks were produced using either the MaxBac system (Invitrogen) or the FastBac system (Gibco-BRL) according to the manufacturer's protocols. In both cases, expression of recombinant human PDEs in the resultant viruses was driven off the viral polyhedron promoter. When using the MaxBac® system, virus was plaque purified twice in order to insure that no wild type (occ+) virus contaminated the preparation. Protein expression was carried out as follows. Sf9 cells were grown at 27° C. in Grace's Insect culture medium (Gibco-BRL) supplemented with 10% fetal bovine serum, 0.33% TC yeastolate, 0.33% lactalbumin hydrolysate, 4.2 mM NaHCO$_3$, 10 μg/mL gentamycin, 100 units/mL penicillin, and 100 μg/mL streptomycin. Exponentially growing cells were infected at a multiplicity of approximately 2 to 3 virus particles per cell and incubated for 48 hours. Cells were collected by centrifugation, washed with nonsupplemented Grace's medium, and quick-frozen for storage.

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the Saccharomyces cerevisiae host was the protease-deficient strain BJ2-54 deposited on Aug. 31, 1998 with the American Type Culture Collection, Manassas, Va., under accession number ATCC 74465. Transformed host cells were grown in 2× SC-leu medium, pH 6.2, with trace metals, and vitamins. After 24 hours, YEP medium-containing glycerol was added to a final concentration of 2× YET/3% glycerol. Approximately 24 hr later, cells were harvested, washed, and stored at −70° C.

Calmodulin Purification

Calmodulin used for activation of the PDE1 enzymes was purified from bovine testes essentially as described by Dedman et al., *Methods in Enzymology*, 102, pp. 1–8 (1983) using the Pharmacia Phenyl-Sepharose® procedure.

Immobilization of Calmodulin on Agarose

Calmodulin was immobilized on BioRad Affi-Gel® 15 per manufacturer's instructions.

Human Phosphodiesterase Preparations
Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 μL reaction mixture containing (final concentrations) 40 mM Tris HCl (pH 8.0), 1 μM $ZnSO_4$, 5 mM $MgCl_2$, and 0.1 mg/mL bovine serum albumin (BSA). Alternatively, in assays assessing PDE1-specific activity, incubation mixtures further incorporated the use of 0.1 mM $CaCl_2$ and 10 μg/mL calmodulin. PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) μg of Crotalus atrox venom then was added, and the incubation was continued for 3 minutes (15 minutes total). The reaction was stopped by addition of 200 μL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Inhibitor analyses were performed similarly to the method described in Loughney et al., *J. Biol. Chem.*, 271, pp. 796–806 (1996), except both cGMP and cAMP were used, and substrate concentrations were kept below 32 nM, which is far below the Km of the tested PDEs.

Purification of PDE1A3 from SF9 Cells

Cell pellets (5 g) were mixed with 10 mL of Lysis Buffer (50 mM MOPS pH 7.5, 2 mM dithiothreitol (DTT), 2 mM benzamidine HCl, 5 μM $ZnSO_4$, 0.1 mM $CaCl_2$, 20 μg/mL calpain inhibitors I and II, and 5 μg/mL each of leupeptin, pepstatin, and aprotinin) at room temperature. The cells were lysed by passage through a French pressure cell (SLM-Aminco® Spectronic Instruments, Inc., Rochester N.Y.). The resultant lysate was centrifuged in a Beckman ultracentrifuge using a type T180 rotor at 45,000 rpm for 1 hr. The supernatant was recovered and filtered through a 0.2 μm filter. This filtrate was applied to a 2.6×90 cm column of SEPHACRYL® S-300 equilibrated in Column Buffer A (Lysis Buffer containing 100 mM NaCl, and 2 mM $MgCl_2$). The column flow rate was adjusted to 1 mL/min and fractions of 7 mL were collected. Active fractions were pooled and supplemented with 0.16 mg of calmodulin. The enzyme was applied overnight at a flow rate of 0.2 mL/min to an ACC-1 agarose immunoaffinity column as described in Hansen et al., *Methods in Enzymology* 159, pp. 453–557 (1988). The column was washed with 5 volumes of Column Buffer B (Column Buffer A without NaCl) and followed by 5 volumes of Column Buffer C (Column Buffer A containing 250 mM NaCl). The column was eluted with Column Buffer D (50 mM MOPS pH 7.5, 1 mM EDTA, 1 mM EGTA, 1 mM DTT, 1 mM benzamidine HCl, 100 mM NaCl, 20 μg/mL calpain inhibitors I and II, and 5 μg/mL each of leupeptin, pepstatin, and aprotinin) by applying one column volume at 0.1 mL/min, stopping flow for 1 hour, and then continuing elution at the same flow rate. Fractions of 0.5 mL were collected. Fractions displaying activity were pooled, and first dialyzed against dialysis buffer containing 25 mM MOPS pH 7.5, 100 mM NaCl, 10 μM $ZnSO_4$, 1 mM $CaCl_2$, 1 mM DTT, and 1 mM benzamidine HCl. A subsequent dialysis against dialysis buffer containing 50% glycerol was performed prior to quick-freezing the sample with dry ice and storage at −70° C. The resultant preparations were about 10 to 15% pure by SDS-PAGE. These preparations had specific activities of about 5 to 20 μmol cAMP hydrolyzed per minute per milligram protein.

Purification of PDE1B from *S. cerevisiae*

Yeast cells (50 g) were thawed by mixing with 100 mL glass beads (0.5 mM, acid washed) and 200 mL Buffer A at room temperature. Buffer A consisted of 50 mM MOPS pH 7.5, 1 mM DTT, 2 mM benzamidine HCl, 0.01 mM $ZnSO_4$, 5 mM $MgCl_2$, 20 μg/mL calpain inhibitors I and II, and 5 μg/mL each of leupeptin, pepstatin, and aprotinin. The mixture was cooled to 4° C., transferred to a Bead-Beater®, and the cells lysed by rapid mixing for 6 cycles of 30 seconds each. The homogenate was centrifuged for 15 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE1B was precipitated by the addition of solid ammonium sulfate (0.33 g/mL supernatant) while stirring in an ice bath and maintaining the pH between 7.0 and 7.5. This mixture then was centrifuged for 22 minutes in a Beckman J2 centrifuge using a JA-10 rotor at 9,000 rpm (12,000×9). The supernatant was discarded and the pellet was dissolved in 100 mL of buffer B (50 mM MOPS pH 7.5, 1 mM DTT, 1 mM benzamidine HCl, 0.01 mM $ZnSO_4$, 2 mM $MgCl_2$, 2 mM $CaCl_2$, and 5 μg/mL each of leupeptin, pepstatin, and aprotinin). The pH and conductivity were corrected to 7.5 and 15–20 milliSiemens (mS), respectively. This solution was loaded onto a 20 mL column of calmodulin-Agarose that had been equilibrated with 10 column volumes of Buffer B at a rate of 1 mL/min. The flow-through was reapplied to the column at least 5 times. The column was washed with 5 volumes of Buffer B, 5 volumes of buffer B containing 250 mM NaCl, and 2 volumes of Buffer B without NaCl again. Elution was accomplished by applying one volume of Buffer C (50 mM MOPS pH 7.5, 1 mM EDTA, 1 mM EGTA, 1 mM DTT, 1 mM benzamidine HCl) at 0.33 mL/min, then stopping flow for 1 hour before continuing the elution. Fractions of about 4 mL were collected and assayed for PDE activity. Active fractions were pooled and concentrated to a volume of 5 mL, using an Amicon ultrafiltration system. The concentrate was then applied to a 320 mL Sephacryl® S-300 column (1.6× 150 cm) that had been equilibrated with at least 2 volumes of Buffer D (25 mM MOPS pH 7.5, 1 mM DTT, 1 mM benzamidine HCl, 0.01 mM $ZnSO_4$, 2 mM $CaCl_2$, and 100 mM NaCl). The column was developed at a flow rate of 1 mL/min (11 cm/hr), and 5 mL fractions were collected. The activity peak was pooled and dialyzed overnight against Buffer D containing 50% glycerol. The purified enzyme was frozen on dry ice and stored at −70° C. The resultant preparations were about >90% pure by SDS-PACE. These preparations had specific activities of about 10 to 30 μmol cGMP hydrolyzed per minute per milligram protein.

Purification of PDE1C3 from Sf9 Cells

Cell pellets (5 g) were thawed on ice with 20 mL of Lysis Buffer (50 mM MOPS pH 7.4, 10 μM $ZnSO_4$, 0.1 mM $CaCl_2$, 1 mM DTT, 2 mM benzamidine HCl, 5 μg/mL each of pepstatin, leupeptin, and aprotinin). Cells were lysed by passage through a French® pressure cell (SLM-Aminco®, Spectronic Instruments) while temperatures were maintained below 10° C. The resultant cell homogenate was centrifuged at 36,000 rpm at 40° C. for 45 min in a Beckman ultracentrifuge using a Type TI45 rotor. The supernatant was discarded and the resultant pellet was resuspended with 40 mL of Solubilization Buffer (Lysis Buffer containing 1 M NaCl, 0.1 M $MgCl_2$, 1 mM $CaCl_2$, 20 μg/mL calmodulin, and 1% Sulfobetaine SB12 (Z3–12) by sonicating using a VibraCell tuner with a microtip for 3×30 seconds. This was performed in a crushed ice/salt mix for cooling. Following sonication, the mixture was slowly mixed for 30 minutes at 4° C. to finish solubilizing membrane bound proteins. This mixture was centrifuged in a Beckman ultracentrifuge using a type TI45 rotor at 36,000 rpm for 45 minutes. The supernatant was diluted with Lysis Buffer containing 10 μg/mL calpain inhibitors I and II. The precipitated protein was centrifuged for 20 minutes at 9,000 rpm in a Beckman JA-10 rotor. The recovered supernatant then was subjected to Mimetic Blue® AP Agarose Chromatography.

To run the Mimetic Blue® AP Agarose Column, the resin initially was shielded by the application of 10 bed volumes of 1% polyvinylpyrrolidone (i.e., MW of 40,000) to block nonspecific binding sites. The loosely bound PVP-40 was removed by washing with 10 bed volumes of 2 M NaCl, and 10 mM sodium citrate pH 3.4. Just prior to addition of the solubilized PCE1C3 sample, the column was equilibrated with 5 bed volumes of Column Buffer A (50 mM MOPS pH 7.4, 10 μM $ZnSO_4$, 5 mM $MgCl_2$, 0.1 mM $CaCl_2$, 1 mM DTT, 2 mM benzamidine HCl).

The solubilized sample was applied to the column at a flow rate of 2 mL/min with recycling such that the total sample was applied 4 to 5 times in 12 hours. After loading was completed, the column was washed with 10 column volumes of Column Buffer A, followed by 5 column volumes of Column Buffer B (Column Buffer A containing 20 mM 5'-AMP), and followed by 5 column volumes of Column Buffer C (50 mM MOPS pH 7.4, 10 μM $ZnSO_4$, 0.1 mM $CaCl_2$, 1 mM DTT, and 2 mM benzamidine HCl). The enzyme was eluted into three successive pools. The first pool consisted of enzyme from a 5-bed volume wash with Column Buffer C containing 1 mM cAMP. The second pool consisted of enzyme from a 10-bed volume wash with Column Buffer C containing 1 M NaCl. The final pool of enzyme consisted of a 5-bed volume wash with Column Buffer C containing 1 M NaCl and 20 mM cAMP.

The active pools of enzyme were collected and the cyclic nucleotide removed via conventional gel filtration chromatography or chromatography on hydroxyapatite resins. Following removal of cyclic nucleotides, the enzyme pools were dialyzed against Dialysis Buffer containing 25 mM MOPS pH 7.4, 10 μM $ZnSO_4$, 500 mM NaCl, 1 mM $CaCl_2$, 1 mM DTT, 1 mM benzamidine HCl, followed by dialysis against Dialysis buffer containing 50% glycerol. The enzyme was quick-frozen with the aid of dry ice and stored at −70° C.

The resultant preparations were about >90% pure by SDS-PAGE. These preparations had specific activities of about 0.1 to 1.0 μmol cAMP hydrolyzed per minute per milligram protein.

Purification of PDE2 from S. cerevisiae

Frozen yeast cell pellets from strain YI34 (10 g, stored at −70° C.) were allowed to thaw on ice in 25 mL of Lysis Buffer (50 mM MOPS, pH 7.2, 1 mM EDTA, 1 mM EGTA, 0.1 mM DTT, 0.1 mM 4-(2-amino-ethyl)benzenesulfonyl fluoride (AEBSF), 1 μg/mL of pepstatin, leupeptin, aprotinin, calpain inhibitors I and II, and 2 mM benzamidine). Cells were lysed by three passages through a French® pressure cell (SLM-Aminco®, Spectronic Instruments). The lysate was centrifuged at 36,000 rpm in a Beckman Ultracentrifuge rotor Type 45Ti for 60 minutes at 4° C. The supernatant was separated from sediment and passed through a 15 mL Epoxy-cGMP Sepnaros® resin at 4° C. two times at about 0.5 mL/min. The column subsequently was washed with 45 mL of Wash Buffer 1 (50 mM MOPS, pH 7.2, 0.1 mM EDTA, 0.1 mM DTT). Following this wash, the column was washed with 45 mL of Wash Buffer 2 (Wash Buffer 1 containing 0.5 M NaCl). Following this salt wash, the column was washed with 15 mL of Wash Buffer 3 (Wash Buffer 1 containing 0.25 M NaCl). The column was transferred to room temperature and allowed to warm. Approximately 25 mL of Elution Buffer (Wash Buffer 3 containing 10 mM cGMP, maintained at room temperature) was applied to the column and the effluent was collected in 2 mL fractions. Small aliquots of each of the fractions were diluted 20-fold in PBS containing 5 mM $MgCl_2$ to allow hydrolysis of the competing ligand and to aid detection of PDE2 activity. Active fractions were passed through a Pharmacia PD-10® gel filtration column to exchange into Wash Buffer 3. This exchanged pool was diluted 50% v/v with sterile 80% glycerol and stored at −20° C. The resultant preparations were greater than 85% pure as judged by SDS-PAGE with subsequent staining of protein by Coomassie R-250. These preparations had specific activities of about 150 to 250 μmol cGMP hydrolyzed per minute per milligram protein.

Preparation of PDE3A from Sf9 Cells

Cells (2×1010) were suspended in Lysis Buffer containing 50 mM MOPS pH 7.5, 2 mM DTT, 2 mM benzamidine HCl, 5 μM $ZnSO_4$, 0.1 mM $CaCl_2$, 20 μg/mL calpain inhibitors I and II, and 5 μg/mL each of leupeptin, pepstatin, and aprotinin. The mixture was sonicated twice for 30 seconds and the cells were lysed in a French pressure cell (SLM-Aminco® Spectronic Instruments) at 4° C. The lysate was centrifuged 100,000×g for 45 minutes. The pellet was washed once in Lysis Buffer and suspended in 46 mL Lysis Buffer with a Dounce homogenizer. Aliquots were stored at −70° C. These preparations had specific activities of about 1 to 2 nmol cAMP hydrolyzed per minute per milligram protein.

Human PDE4A, 4B, 4C, 4D Preparations

Preparation of PDE4A from *S. cerevisiae*

Yeast cells (50 g of yeast strain YI26 harboring HDUN1.46) were thawed at room temperature by mixing with 50 mL of Lysis Buffer (50 mM MOPS pH 7.5, 10 μM $ZnSO_4$, 2 mM $MgCl_2$, 14.2 mM 2-mercaptoethanol, 5 μg/mL each of pepstatin, leupeptin, aprotinin, 20 μg/mL each of calpain inhibitors I and II, and 2 mM benzamidine HCl). Cells were lysed in a French® pressure cell (SLM-Aminco®, Spectronic Instruments) at 10° C. The extract was centrifuged in a Beckman JA-10 rotor at 9,000 rpm for 22 minutes at 4° C. The supernatant was removed and centrifuged in a Beckman TI45 rotor at 36,000 rpm for 45 minutes at 4° C.

PDE4A was precipitated from the high-speed supernatant by the addition of solid ammonium sulfate (0.26 g/mL supernatant) while stirring in an ice bath and maintaining the pH between 7.0 and 7.5. The precipitated proteins containing PDE4A were collected via centrifugation in a Beckman JA-10 rotor at 9,000 rpm for 22 minutes. The precipitate was resuspended in 50 mL of Buffer G (50 mM MOPS pH 7.5, 10 μM $ZnSO_4$, 5 mM $MgCl_2$, 100 mM NaCl, 14.2 mM 2-mercaptoethanol, 2 mM benzamidine HCl, 5 μg/mL each of leupeptin, pepstatin, and aprotinin, and 20 μg/mL each of calpain inhibitors I and II) and passed through a 0.45 μm filter.

The resuspended sample (50 to 100 mL) was loaded onto a 5×100 cm column of Pharmacia SEPHACRYL® S-300 equilibrated in Buffer G. Enzyme activity was eluted at a flow rate of 2 mL/min and pooled for later fractionation.

The PDE4A isolated from gel filtration chromatography was applied to a 1.6×20 cm column of Sigma Cibacron Blue Agarose-type 300 (10 mL) equilibrated in Buffer A (50 mM MOPS pH 7.5, 10 μM $ZnSO_4$, 5 mM $MgCl_2$, 14.2 mM 2-mercaptoethanol, and 100 mM benzamidine HCl). The column was washed in succession with 50 to 100 mL of Buffer A, 20 to 30 mL of Buffer A containing 20 mM 5'-AMP, 50 to 100 mL of Buffer A containing 1.5 M NaCl, and 10 to 20 mL of Buffer C (50 mM Tris HCl pH 8, 10 μM $ZnSO_4$, 14.2 mM 2-mercaptoethanol, and 2 mM benzamidine HCl). The enzyme was eluted with 20 to 30 mL of Buffer C containing 20 mM cAMP.

The PDE activity peak was pooled, and precipitated with ammonium sulfate (0.33 g/mL enzyme pool) to remove excess cyclic nucleotide. The precipitated proteins were resuspended in Buffer X (25 mM MOPS pH 7.5, 5 μM $ZnSO_4$, 50 mM NaCl, 1 mM DTT, and 1 mM benzamidine HCl), and desalted via gel filtration on a Pharmacia PD-10® column per manufacturer's instructions. The enzyme was quick-frozen in a dry ice/ethanol bath and stored at −70° C.

The resultant preparations were about >80% pure by SDS-PAGE. These preparations had specific activities of about 10 to 40 μmol cAMP hydrolyzed per minute per milligram protein.

Preparation of PDE4B from *S. cerevisiae*

Yeast cells (150 g of yeast strain YI23 harboring HDUN2.32) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 μg/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 seconds each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4B was precipitated by the addition of solid ammonium sulfate (0.26 g/mL supernatant) while stirring in an ice bath and maintaining the pH between 7.0 and 7.5. This mixture was then centrifuged for 22 minutes in a Beckman J2 centrifuge using a jA-10 rotor at 9,000 rpm (12,000×g). The supernatant was discarded and the pellet was dissolved in 200 mL of Buffer A (50 mM MOPS pH 7.5, 5 mM $MgCl_2$, 1 mM DTT, 1 mM benzamidine HCl, 1 and 5 μg/mL each of leupeptin, pepstatin, and aprotinin). The pH and conductivity were corrected to 7.5 and 15–20 mS, respectively.

The resuspended sample was loaded onto a 1.6×200 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM CAMP) and 50 to 75 mL of Buffer E containing 1 M NaCl. The PDE activity peak was pooled, and precipitated with ammonium sulfate (0.4 g/mL enzyme pool) to remove excess cyclic nucleotide. The precipitated proteins were resuspended in Buffer X (25 mM MOPS pH 7.5, 5 μM $ZnSO_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >90% pure by SDS-PAGE. These preparations had specific activities of about 10 to 50 μmol cAMP hydrolyzed per minute per milligram protein.

Preparation of PDE4C from *S. cerevisiae*

Yeast cells (150 g of yeast strain YI30 harboring HDUN3.48) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 μg/mL each of pepstatin, leupeptin, aprotinin, calpain inhibitors I and II) at room temperature. The mixture was cooled to 4° C., transferred to a BEAD-BEATER®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C.

The supernatant was recovered and PDE4C was precipitated by the addition of solid ammonium sulfate (0.26 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM $MgCl_2$, 1 mM DTT, 2 mM benzamidine HCl, and 5 μg/mL each of leupeptin, pepstatin, and aprotinin). The pH and conductivity were corrected to 7.5 and 15–20 mS, respectively.

The resuspended sample was loaded onto a 1.6×20 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and then 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, 1 and 20 mM cAMP) and 50 to 75 mL of Buffer E containing 1 M NaCl. The PDE4C activity peak was pooled, and precipitated with ammonium sulfate (0.4 g/mL enzyme pool) to remove excess cyclic nucleotide. The precipitated proteins were resuspended in Buffer X (25 mM MOPS pH 7.2, 5 $\mu$M ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >80% pure by SDS-PAGE. These preparations had specific activities of about 10 to 20 $\mu$mol cAMP hydrolyzed per minute per milligram protein.

Preparation of PDE4D from *S. cerevisiae*

Yeast cells (100 g of yeast strain YI29 harboring HDUN4.11) were thawed by mixing with 150 mL glass beads (0.5 mM, acid washed) and 150 mL Lysis Buffer (50 mM MOPS pH 7.2, 10 $\mu$M ZnSO$_4$, 2 mM MgCl$_2$, 14.2 mM 2-mercaptoethanol, 2 mM benzamidine HCl, 5 $\mu$g/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4D was precipitated by the addition of solid ammonium sulfate (0.33 g/mL superatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 100 mL of Buffer A (50 mM MOPS pH 7.5, 10 $\mu$M ZnSO$_4$, 5 mM MgCl$_2$, 14.2 mM 2-mercaptoethanol, 100 mM benzamidine HCl, and 5 $\mu$g/mL each of leupeptin, pepstatin, aprotinin, calpain inhibitor I and II). The pH and conductivity were corrected to 7.5 and 15–20 mS, respectively.

At a flow rate of 0.67 mL/min, the resuspended sample was loaded onto a 1.6×20 cm column (10 mL) of Sigma Cibacron Blue Agarose-type 300 equilibrated in Buffer A. The column was washed in succession with 50 to 100 mL of Buffer A, 20 to 30 mL of Buffer A containing 20 mM 5'-AMP, 50 to 100 mL of Buffer A containing 1.5 M NaCl, and then 10 to 20 mL of Buffer C (50 mM Tris HCl pH 8, 10 $\mu$M ZnSO$_4$, 14.2 mM 2-mercaptoethanol, 2 mM benzamidine HCl). The enzyme was eluted with 20 to 30 mL of Buffer C containing 20 mM cAMP.

The PDE4D activity peak was pooled and precipitated with ammonium sulfate (0.4 g/mL enzyme pool) to remove excess cyclic nucleotide. The precipitated proteins were resuspended in Buffer X (25 mM MOPS pH 7.2, 5 $\mu$M ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme preparation was quick-frozen in a dry ice/ethanol bath and stored at −70° C.

The resultant preparations were about >80% pure by SDS-PAGE. These preparations had specific activities of about 20 to 50 $\mu$mol cAMP hydrolyzed per minute per milligram protein.

Purification of PDE5 from *S. cerevisiae*

Cell pellets (29 g) were thawed on ice with an equal volume of Lysis Buffer (25 mM Tris HCl, pH 8, 5 M MgCl$_2$, 0.25 mM DTT, 1 mM benzamidine, and 10 $\mu$M ZnSO$_4$). Cells were lysed in a Microfluidizer (Microfluidics Corp.) using nitrogen at 20,000 psi. The lysate was centrifuged and filtered through 0.45 $\mu$m disposable filters. The filtrate was applied to a 150 mL column of Q SEPHAROSE® Fast-Flow (Pharmacia). The column was washed with 1.5 volumes of Buffer A (20 mM Bis-Tris Propane, pH 6.8, 1 mM MgCl$_2$, 0.25 mM DTT, 10 $\mu$M ZnSO$_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM MgCl$_2$, 0.25 mM DTT, 10 $\mu$M ZnSO$_4$, and 250 mM KCl) . After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 $\mu$M ZnSO$_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 $\mu$mol cGMP hydrolyzed per minute per milligram protein.

Preparation of PDE7 from *S. cerevisiae*

Cell pellets (126 g) were thawed and resuspended at room temperature for about 30 minutes with an equal volume of Lysis Buffer (50 mM Tris HCl, pH 8, 1 mM EDTA, 1 mM DTT, 50 mM NaCl, 2 mM benzamidine HCl, and 5 $\mu$g/mL each of pepstatin, leupeptin, and aprotinin). The cells were lysed at 0–4° C. with the aid of glass beads (125 mL) in a Bead-Beater for 6×30 second cycles. The lysate was centrifuged and filtered through 0.45 $\mu$m disposable filters. The filtered extract (178 mL) was distributed into 4 mL aliquots, quick-frozen with dry ice, and stored in a freezer at −70° C. These preparations were stable to several cycles of freezing and thawing and had specific activities of about 50 to 100 pmol cAMP hydrolyzed per minute per milligram protein.

Lipopolysaccharide-Stimulated TNFα Release from Human Peripheral Blood Lymphocytes To assess the ability of a compound to reduce TNFα secretion in human peripheral blood lymphocytes (PBL), the following tests were performed. Previous studies have demonstrated that incubation of human PBL with cAMP-elevating agents, such as prostaglandin E21, forskolin, 8-bromo-cAMP, or dibutryl-cAMP, inhibits the secretion of TNFα by the cells when stimulated by lipopolysaccharide (LPS; endotoxin). Accordingly, preliminary experiments have been performed to demonstrate that selective PDE4 inhibitors, such as rolipram, inhibit LPS-induced TNFa secretion from human lymphocytes in a dose-dependent fashion. Hence, TNFα secretion from human PBL was used as a standard for the ability of a compound to elevate intracellular cAMP concentrations and/or to inhibit PDE4 activity within the cell.

Heparinized blood (approximately 30 mL) drawn from human volunteers was mixed 1:1 with Dulbecco's modified phosphate-buffered saline. This mixture was mixed 1:1 with HISTOPAQUE® and centrifuged at 1,500 rpm at room temperature without braking in the swinging bucket of a Beckman model TJ6 centrifuge. Erythrocytes were centrifuged to the bottom of the tubes, and serum remained at the surface of the tubes. A layer containing lymphocytes sedimented between the serum and HISTOPAQUE® layers, and was removed by aspiration to a fresh tube. The cells were quantified and adjusted to $3 \times 10^6$ cells/mL and a 100 μL aliquot is placed into the wells of a 96 well plate. Test compounds and RPMI media (Gibco/BRL Life Sciences) are added to each of the wells 15 minutes prior to addition of bacterial LPS (25 mg/mL). The mixture was allowed to incubate for 20 hours at 37° C. in a humidified chamber. The cells then were separated by centrifuging at 800 rpm for 5 minutes at room temperature. An aliquot of 180 μL of supernatant was transferred to a new plate for determination, of TNFα concentration. TNFα protein in the cell supernatant fluids was measured using a commercially available enzyme-linked immunosorbent assay (ELISA) (CYTOSCREEN® Immunoassay Kit from Biosource International).

The cell-based assay provided the following results for various pyrrolidine compounds of the present invention. The $EC_{50}$ values (i.e., effective concentration of the compound capable of inhibiting 50% of the total TNFα) illustrate the ability of the present compounds to inhibit LPS-stimulated TNFα release from human PBL.

The table below illustrates the ability of compounds of formula (II) to inhibit PDE4 activity and TNFα release in vitro. In the following table, the $IC_{50}$ values were determined against human recombinant PDE4.

| Sample Number[1] (Ex. No.)[2] | Stereochemistry | PDE4 $IC_{50}$ (M × $10^{-9}$) | PBL/TNFα $EC_{50}$ (M × $10^{-9}$) |
|---|---|---|---|
| 1 | Absolute, as drawn | 87.0 | 1,205.8 |
| 2 | Absolute, as drawn | 260.0 | 1,900.0 |
| 3 | Relative stereochemistry as drawn; racemic | 180.0 | 3,261.7 |
| 4 | Relative, stereochemistry as drawn; racemic | 190.0 | 3,611.5 |
| 5 | Relative, stereochemistry as drawn; racemic | 75.0 | 1,551.3 |
| 6 | Relative, stereochemistry as drawn; racemic | 75.0 | 3,657.5 |
| 7 | Absolute, as drawn | 5,800.0 | |
| 8 | Absolute, as drawn | 784.0 | 909.6 |
| 9 | Absolute, as drawn | 13,000.0 | |
| 10 | Absolute, as drawn | 7,900.0 | |
| 11 | Absolute, as drawn | 3,700.0 | |
| 12 | Absolute, as drawn | 2,600.0 | |
| 13 | Absolute, as drawn | 1,000.0 | 2,339.5 |
| 14 | Absolute, as drawn | 900.0 | 2,981.5 |
| 15 | Relative stereochemistry as drawn; racemic, mixture of ether isomers | 4.3 | 108.8 |
| 16 | Relative stereochemistry as drawn; racemic, mixture of ether isomers | 7.3 | 46.4 |
| 17 | Absolute, as drawn | 2,211.6 | 3,447.3 |
| 18 | Absolute, as drawn | 1,027.3 | 5,101.6 |
| 19 | Absolute, as drawn | 1,974.0 | 1,951.1 |
| 20 (Ex. 63) | Absolute, as drawn | 536.0 | 170.0 |
| 21 (Ex. 62) | Absolute, as drawn | 16.2 | 278.0 |
| 22 (Ex. 46) | Absolute, as drawn | 520.4 | 164.0 |
| 23 (Ex. 21) | Absolute, as drawn | 1,592.2 | |
| 24 | Absolute, as drawn; mixture of ether isomers | 1.6 | 40.0 |
| 25 | Absolute, as drawn; mixture of ether isomers | 2.8 | 12.2 |
| 26 | Absolute, as drawn; mixture of ether isomers | 35.0 | 106.0 |
| 27 | Absolute, as drawn; mixture of ether isomers | 1.8 | 36.0 |
| 28 | Absolute, as drawn | 23.0 | 241.0 |
| 29 | Absolute, as drawn | 4.9 | 78.0 |
| 30 | Absolute, as drawn | 100.0 | 440.0 |
| 31 | Absolute, as drawn | 3.6 | 35.0 |
| 32 (Ex. 50) | Absolute, as drawn | 1,000.0 | 801.0 |
| 33 (Ex. 55) | Absolute, as drawn | 2,100.0 | |
| 34 (Ex. 20) | Absolute, as drawn | 402.6 | 250.0 |
| 35 (Ex. 10) | Absolute, as drawn | 35.6 | 20.3 |
| 36 (Ex. 19) | Absolute, as drawn | 187.2 | 1,600.0 |
| 37 (Ex. 14) | Absolute, as drawn | .768 | 72.0 |
| 38 (Ex. 12) | Absolute, as drawn | 5.9 | 36.0 |
| 39 (Ex. 16) | Absolute, as drawn | 2.7 | 48.1 |
| 40 (Ex. 17) | Absolute, as drawn | 98.4 | 139.1 |
| 41 (Ex. 22) | Absolute, as drawn | 27.0 | 266.9 |
| 42 (Ex. 30) | Absolute, as drawn | 7.5 | 171.7 |
| 43 (Ex. 31) | Absolute, as drawn | 12.5 | 145.8 |
| 44 (Ex. 28) | Absolute, as drawn | 41.2 | 238.0 |
| 45 (Ex. 51) | Absolute, as drawn | 247.6 | 694.0 |
| 46 (Ex. 29) | Absolute, as drawn | 1,805.9 | 13,317.0 |
| 47 (Ex. 27) | Absolute, as drawn | 2,727.4 | 20,000.0 |
| 48 (Ex. 37) | Absolute, as drawn | 89.7 | 446.0 |
| 49 (Ex. 35) | Absolute, as drawn | 14.3 | 26.2 |
| 50 (Ex. 41) | Absolute, as drawn | 44.8 | 151.2 |
| 51 (Ex. 42) | Absolute, as drawn | 44.7 | 72.6 |
| 52 (Ex. 39) | Absolute, as drawn | 26.7 | |
| 53 (Ex. 38) | Absolute, as drawn; mixture of tetrahydrofuryl isomers | 116.3 | 112.6 |
| 54 (Ex. 36) | Absolute, as drawn; mixture of 2,2-dimethyl-4-oxo-4-pyrrolidin-1-yl-butyric acid and 3,3-dimethyl-4-oxo-4-pyrrolidin-1-yl-butyric acid amides | 464.7 | |

-continued

| Sample Number[1] (Ex. No.)[2] | Stereochemistry | PDE4 IC$_{50}$ (M × 10$^{-9}$) | PBL/TNFα EC$_{50}$ (M × 10$^{-9}$) |
|---|---|---|---|
| 55 (Ex. 33) | Absolute, as drawn | 1.842.1 | |
| 56 (Ex. 43) | Absolute, as drawn | 4.0 | |
| 57 (Ex. 18) | Absolute, as drawn | 95.6 | |
| 58 | Absolute, as drawn | | |
| 59 | Racemic; relative stereochemistry as shown | 58.0 | 170.0 |
| 60 | Racemic; relative stereochemistry as shown | 74.0 | 44.0 |
| 61 | Racemic; relative stereochemistry as shown | 18.3 | 57.8 |
| 62 | Racemic, relative stereochemistry as shown | 6.8 | 10.2 |
| 63 | Racemic, relative stereochemistry as shown, nonbornyl residue racemic | 51.4 | 267.4 |
| 64 | Racemic; relative stereochemistry as shown, nonbornyl residue racemic | 8.5 | 36.2 |
| 65 | Racemic; relative stereochemistry as shown | 220.0 | 181.0 |
| 66 (Ex. 8(C)) | Absolute stereochemistry as shown | 14.0 | 71.6 |
| 67 (Ex. 8(D)) | Absolute stereochemistry as shown | 514.7 | 603.3 |
| 68 (Ex. 8(B)) | Absolute stereochemistry as shown | 61.1 | 169.9 |
| 69 (Ex. 8(A)) | Absolute stereochemistry as shown | 13.3 | 57.0 |
| 70 | Absolute stereochemistry as shown; single undefined alcohol isomer 1 | 498.5 | 547.2 |
| 71 | Absolute stereochemistry as shown; single undefined alcohol isomer 2 | 1,707.2 | |
| 72 | Absolute, as drawn | 2,452.6 | |
| 73 (Ex. 57) | Absolute, as drawn | 9,131.0 | |
| 74 (Ex. 53) | Absolute, as drawn | 352.3 | 557.3 |
| 75 (Ex. 52) | Absolute, as drawn | 45.1 | 121.0 |
| 76 (Ex. 45) | Absolute, as drawn | 36.6 | 173.0 |
| 77 (Ex. 47) | Absolute, as drawn | 188.7 | 580.0 |
| 78 (Ex. 48) | Absolute, as drawn | 760.1 | 1,288.6 |
| 79 (Ex. 56) | Absolute, as drawn | 1,639.0 | 2,366.6 |
| 80 (Ex. 49) | Absolute, as drawn | 300.0 | 272.4 |
| 81 (Ex. 54) | Absolute, as drawn | 700.0 | 624.8 |
| 82 (Ex. 9) | Absolute, as drawn | 389.8 | 490.0 |
| 83 (Ex. 59) | Absolute, as drawn | 172.0 | 51.0 |
| 84 (Ex. 58) | Absolute, as drawn | 21.7 | 40.0 |
| 85 (Compound VII) | Absolute, as drawn | 3,576.8 | |
| 86 (Compound VIII) | Absolute, as drawn | 6,077.6 | |
| 87 (Ex. 23) | Absolute, as drawn | 896.6 | 934.4 |
| 88 (Ex. 24) | Absolute, as drawn | 953.4 | 629.5 |
| 89 (Ex. 25) | Absolute, as drawn | 699.0 | 860.0 |
| 90 (Ex. 11) | Absolute, as drawn | 69.4 | 61.0 |
| 91 (Ex. 60) | Absolute, as drawn | 150.0 | 44.0 |
| 92 (Ex. 61) | Absolute, as drawn | 439.4 | |
| 93 (Ex. 20) | Absolute, as drawn | 33.1 | 7.8 |
| 94 (Ex. 15) | Absolute stereochemistry as shown | 238.2 | 1,800.0 |

[1]See Appendix A for structure of each sample
[2]Example Number

The data presented above shows that the present compounds are potent inhibitors of PDE4, e.g., the compounds have an IC$_{50}$ vs. human recombinant PDE4 of about 700 pM to about 15 μM. Preferred compounds have an IC$_{50}$ of about 100 nM or less, and especially preferred compounds have an IC$_{50}$ of about 50 nM or less.

Similarly, preferred compounds have a PBL/TNFα EC$_{50}$ about 500 nM or less, and preferably about 200 nM or less. More preferred compounds have a PBL/TNFα EC$_{50}$ of about 100 nM or less.

To achieve the full advantages of the present invention, the compounds have an IC$_{50}$ vs. human recombinant PDE4 of about 100 nM or less and a PBL/TNFα EC$_{50}$ of about 500 nM or less. More preferably, the compounds have an IC$_{50}$ of about 50 nM or less and a PBL/TNFα EC$_{50}$ of about 100 nM or less.

Animal Models

Assay for Inhibition of Serum TNFα Levels in Mammals (Mouse/TNFα ED$_{50}$ (mg/kg))

In order to assess the ability of a compound to reduce serum TNFα levels in mammals, the following protocol was employed. Those skilled in the art appreciate that previous studies have demonstrated that incubation of LPS-activated human monocytes with agents that can elevate cAMP, like PGE2, forskolin, and the dbcAMP, inhibited secretion of TNFα. PDE4 inhibitors like rolipram, which also elevate cAMP, have been found to inhibit serum TNFα as well. Rolipram has also been found to inhibit secretion of TNFα from LPS-activated mouse macrophages. Accordingly, in vivo efficacy of a PDE4 reducing compound was shown by dosing with compound and measuring reduction of serum TNFα levels in LPS-injected mice. Female C3H mice, 20–25 gm body weight, were fasted overnight and dosed intraperitoneally with test compound in appropriate vehicle 60 minutes before LPS injection. Five μg of LPS was then injected intraperitoneally into the mice. Ninety minutes after LPS injection, mice were bled from the heart. Blood was allowed to clot overnight at 4° C. Samples were centrifuged for 10 minutes in a microcentrifuge and the serum removed and stored at −20° C. until analysis. Serum levels of TNFα were subsequently measured using a commercially available ELISA kit (Genzyme) following the protocol enclosed in the kit. The percent of inhibition of serum TNFα levels caused by the compound was determined relative to serum TNFα levels in control mice receiving vehicle alone.

Combined Mouse endotoxin-stimulated TNFα Release and Locomotor Activity Assay ($ED_{50}$ (mg/kg))

The purpose of this study was to determine the efficacy of PDE4 inhibitors in vivo in an LPS mouse model together with a determination with respect to central nervous system (CNS) side-effects manifested by a decrease in spontaneous mobility.

The test animals were female Balb/c mice, having an average weight of about 20 g. The PDE4 inhibitors, formulated in 30% Cremophor® EL, were administered via intraperitoneal (i.p.) injections at doses of 0.1, 1.0, 10.0, and 100 mg/kg. Individual dose volumes (about 150 μL) were adjusted based on the body weights measured. One hour later, 5 mg/kg LPS in a final volume of 200 μL was injected via the tail vein to each animal. Ninety minutes following the LPS treatment, the animals were bled and serum samples were collected before being stored at −70° C. until assayed.

For efficacy determination, the serum samples were diluted two-fold and TNFα levels were determined using the CYTOSCREEN® Immunoassay Kit (Biosource International). The data were averaged between triplicate sample subjects for each of the tested compounds.

Movement of the X-Y plane, or rearing up on the hind legs, was quantified by counting the number of "light-beam" crosses per unit of time. A decrease in the number of activity events is directly proportional to the mobility or immobilization of the animal. The quantitative scoring correlated well with the subjective measurements described above.

The following table summarizes the Mouse/TNFα $ED_{50}$ (mg/kg) results obtained by the above-described method:

| Sample Number[1] (Ex. No.)[2] | Mouse/TNFα $ED_{50}$ (mg/kg) | $ED_{50}$ (mg/kg)[3] |
|---|---|---|
| 29 | — | 9.8 |
| 31 | 3 | 83 |
| 61 | 0.2 | >50 |
| 62 | 0.08 | >50 |
| 66 (Ex. 8(C)) | 5 | >50 |
| 67 (Ex. 8(D)) | — | >50 |
| 68 (Ex. 8(B)) | 12 | 20 |
| 69 (Ex. 8(A)) | 7 | <0.5 |

[3] effective dose, in mg/kg, that decreases spontaneous mobility 50% of control.

It also was determined that compounds of formula (II) have fewer central nervous system side effects compared to rolipram and to compounds disclosed in Feldman et al. U.S. Pat. No. 5,665,754. It also was found that central nervous system activity is related to the absolute stereochemistry of the present compounds.

It is known that stereoisomers of drugs can have substantially different biological activities, e.g., potency, selectivity, absorption, distribution, metabolism, execution, and side effect profiles. In the present invention, the enantiomers and diastereromers represented by compounds (A)–(D) of Example 8 were tested for effects on in vitro PDE activity, cell-based LPS/TNFα release from human peripheral blood lymphocytes (PBLs), mouse mobility, and ferret emesis.

As shown in the following table, compounds of Examples 8(C) and 8(A) show similar inhibition of PDE4 and LPS-stimulated TNFα release, but substantially different behavioral profiles. Compounds of Examples 8(C) and 8(A), which exhibit less CNS activity, are derived from the predominant product of the [3+2] azomethine ylide cyclization to the chiral α, β-unsaturated amide. Thus, the absolute stereochemistry of a PDE4 inhibitor of the present invention contributes significantly to the behavioral profile of the compound.

| Examples | Compound | PDE4 $IC_{50}$ (nM) | Mouse/TNFα $ED_{50}$ (mg/kg) | CNS Side Effects[1] |
|---|---|---|---|---|
| Ex. 8(A) | | 13.3 | 7 | Severe |
| Ex. 8(C) | | 14.0 | 5 | No effect |

-continued

| Examples | Compound | PDE4 IC$_{50}$ (nM) | Mouse/TNFα ED$_{50}$ (mg/kg) | CNS Side Effects[1] |
|---|---|---|---|---|
| Ex. 8(B) | | 61.1 | 12 | No effect |
| Ex. 8(D) | | 514.7 | — | No effect |
| Sample No. 62 | | 6.8 | 0.08 | Little to no effect (at 50 mg/kg) |
| Sample No. 61 | | 18.3 | 0.2 | Little to no effect (at 50 mg/kg) |

[1] CNS side effects were determined by a subjective assessment of mouse immobility following injection of compounds i.p. at 1, 10, and 100 mg/kg doses. Mobility (or lack thereof) assessment was scored by observing the following: reduced exploratory behavior, fattened posture, prone positioning, ruffled fur, etc. No apparent effects were noted over the 60 minutes time frame of assessment with Examples 8(C), 8(D), and 8(B). However, mice were affected at all doses when given Example 8(A). Furthermore, at the highest dose of Example 8(A), mice became moribund and died within 10 minutes of treatment.

The data presented above show that compounds of formula (II) are potent and selective inhibitors of PDE4. As an important added advantage, the compounds of formula (II) also reduced or eliminated the adverse CNS side effects associated with prior PDE4 inhibitors. Compounds of formula (II) were further tested for emetogenic properties in animal models to further illustrate the efficacy of the compounds. The method and results of the emetogenic test are set forth below.

Emetic Modeling in the Ferret Following Oral and Intravenous Dosing with PDE4-Selective Inhibitors This study was conducted to investigate the emetogenic properties of PDE4 inhibitors in vivo. The ferret previously has been established as a valuable tool for assessing emesis following exposure to test compounds. Previous studies indicated that the emetic response of a ferret to many PDE4 inhibitors is predictive of the disposition of humans toward the same test compounds. Therefore, lack of and/or decrease in emetic potential of test compounds in ferrets predicts a favorable nonemetic effect in humans. Emesis is a complex physiological response to noxious agents that can be intiated peripherally or centrally. Hence, PDE4-selective agents were tested when administered both intravenously or orally.

The test animals were adult, castrated, and descented male ferrets (species=Mustela putorius furo, Strain=Sable) ranging in weight from about 1 to 1.5 kg. The tests were performed in quadruplicate on animals that were naive to PDE4 inhibitors. The PDE4 inhibitors were formulated in 10% Polyoxyl-35 castor oil (CREMOPHOR® EL, available from BASF Corporation, Parsippany, N.J.) in phosphate buffered saline (PBS), and were administered via i.v. injections into an indwelling catheter surgically positioned in the right external jugular vein at a rate of 0.66 mL per kg body weight. PDE4 inhibitors for oral consumption were formulated in 30% CREMOPHOR® EL in PBS, and administered by intubating animals with a 16-gauge feeding needle into the stomach. The animals received the PDE4 inhibitors in a volume of 1.33 mL per kg body weight.

All animals were fasted for 8 to 12 hours prior to administration of PDE4 inhibitors. Following administration of a PDE4 inhibitor, emetic and behavioral responses were quantified for three hours post dosing. The total number of emetic responses and vomiting episodes were quantified during the observation interval. In addition, latency time to first emetic episode, duration of emesis episodes, and gross behavioral changes including ataxia, profuse and viscous salivation, mouth clawing, hyperventilation, backward walking, flattened body posture, hyperactivity, lip licking, and general appearance were recorded.

For comparative purposes, the emetogenic effect of Examples 8(C) and 8(A) were tested intravenously at 1.0, 2.5, 5.0, and 10 mg/kg and orally at 2.5, 10, 17, and 25 mg/kg. The results are summarized in the following table:

COMPARATIVE RESULTS

| Compound of Example 8(A) Oral (mg/kg) | Vomits | Retches | Number of Emetic Events Total | Responders |
|---|---|---|---|---|
| 2.5 | 0 | 0 | 0 | 0/4 |
| 10.0 | 5 | 27 | 32 | 3/4 |
| 17.0 | 7 | 51 | 58 | 3/4 |
| 25.0 | 26 | 88 | 114 | 4/4 |
| Intravenous (mg/kg) | Vomits | Retches | Total | Responders |
| 1.0 | 0 | 0 | 0 | 0/4 |
| 2.5 | 0 | 3 | 3 | 1/4 |
| 5.0[1] | 0 | 300 | 300 | 2/2 |
| 10.0 | — | — | — | |

COMPARATIVE RESULTS

| Compound of Example 8(C) Oral (mg/kg) | Vomits | Retches | Number of Emetic Events Total | Responders |
|---|---|---|---|---|
| 2.5 | 0 | 0 | 0 | 0/4 |
| 10.0 | 8 | 14 | 22 | 2/4 |
| 17.0 | 1 | 17 | 18 | 2/3 |
| 25.0 | 12 | 61 | 73 | 4/4 |
| Intravenous (mg/kg) | Vomits | Retches | Total | Responders |
| 1.0 | 0 | 0 | 0 | 0/4 |
| 2.5 | 0 | 0 | 0 | 0/4 |
| 5.0[1] | 0 | 10 | 10 | 2/4 |
| 10.0 | 4 | 27 | 31 | 4/4 |

[1]Only two ferrets were dosed intravenously with 5 mg/kg Example 8(A) because of the severity of the responses. Therefore, 10 mg/kg Example 8(A) was not administered intravenously.

In general, both Examples 8(C) and 8(A), delivered either orally or via intravenous injection, produced a clear dose response in terms of emetic behavior. Example 8(A) produced a much stronger emetic response than Example 8(C). This was readily apparent when the responses to oral dosing was compared. For example, at a dose of 25 mg/kg body weight, Example 8(A) produced more retching and vomiting episodes than the same oral dose of Example 8(C). In addition, the number of retches and vomiting events per episode was much greater for Example 8(A) than Example 8(C) in this dose group. A similar trend was apparent at oral dosages of 17 and 11 mg/kg body weight, with Example 8(A) exhibiting a stronger response than Example 8(C). There were no apparent differences observed between the lowest dosed groups for both molecules. In these cases, some minor lip licking/mouth pawing was evident with both compounds, but no emetic responses were observed.

The results of oral dosing contrast markedly with that of intravenous dosing. At an intravenous dose of 5 mg/kg body weight of Example 8(A), one of the tested animals died almost immediately after dosing (within 5 minutes), whereas the second animal was clearly distressed, but recovered after 3 hours. The distress can be attributed either to an acute toxicity event or to an exaggerated pharmacological response to centrally mediated emesis. It also was noted that the distressed and labored breathing in these dosed animals was difficult to distinguish from extreme retching behavior. The effects were not nearly as severe with intravenous administration of Example 8(C) as shown in the above table. Although all animals exhibited emetic behavior at the 10 mg/kg body weight dose with Example 8(C), none displayed the distress associated with the 5 mg/kg dose of Example 8(A). With the exception of the 5 mg/kg body weight dose of Example 8(A), all of the animals recovered from their treatment and appeared normal.

The results summarized in the above table show that the compounds of the present invention are useful for selectively inhibiting PDE4 activity in a mammal, without exhibiting the adverse CNS and emetic effects associated with prior PDE4 inhibitors. obviously, many modifications and variations of the invention as hereinbefore set forth can be made without departing from the spirit and scope thereof and, therefore, only such limitations should be imposed as are indicated by the appended claims.

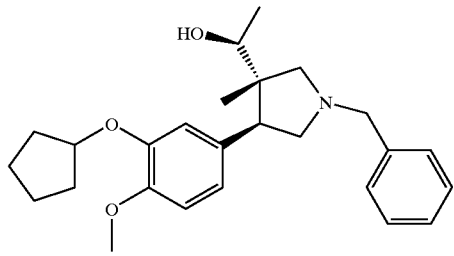

Sample No. 1

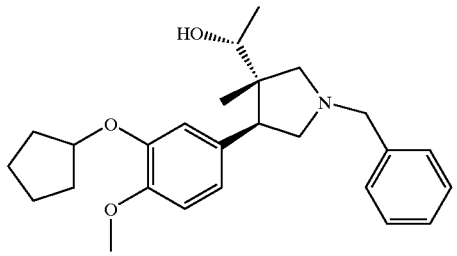

Sample No. 2

-continued
Sample No. 3
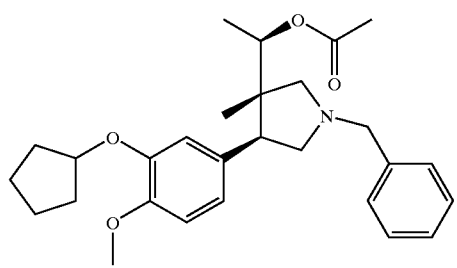
Sample No. 4
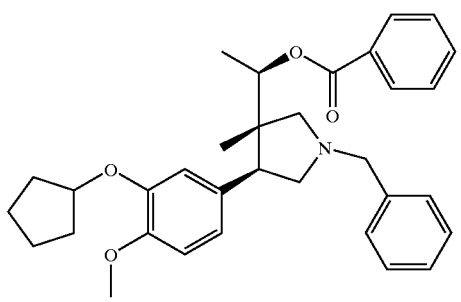
Sample No. 5
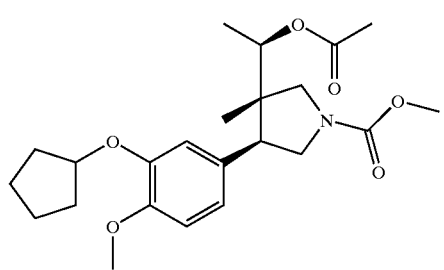
Sample No. 6
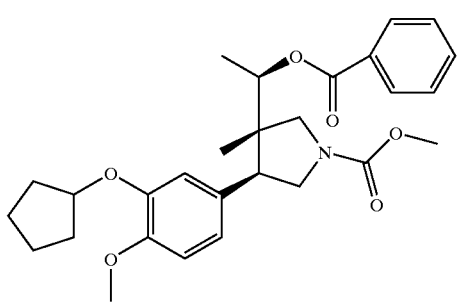
Sample No. 7
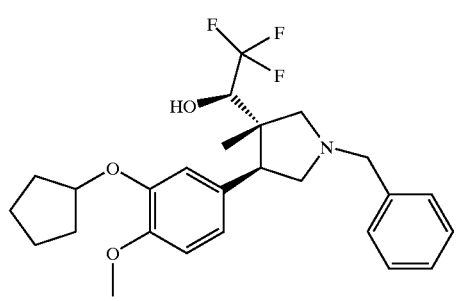
Sample No. 8
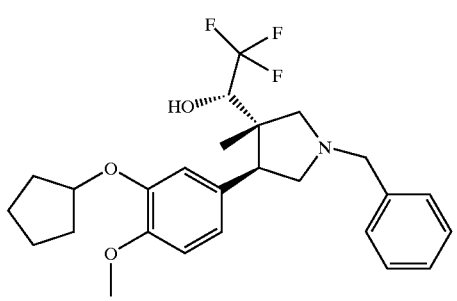
Sample No. 9
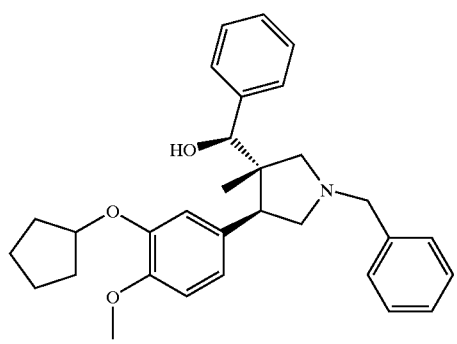
Sample No. 10
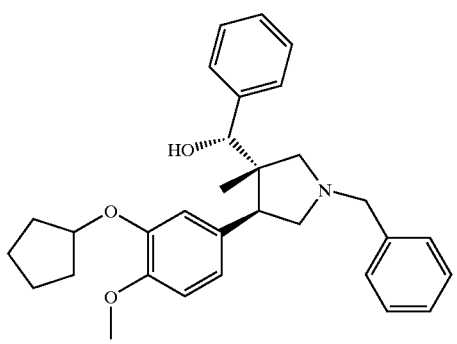
Sample No. 11
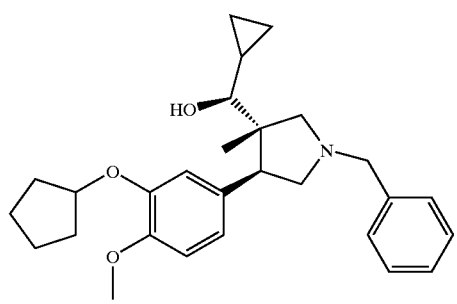
Sample No. 12
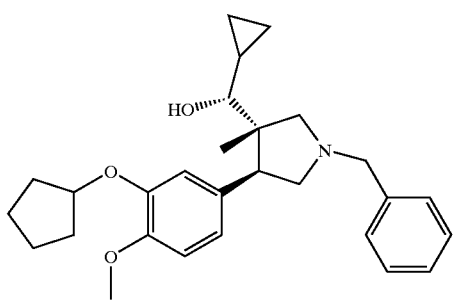

Sample No. 13
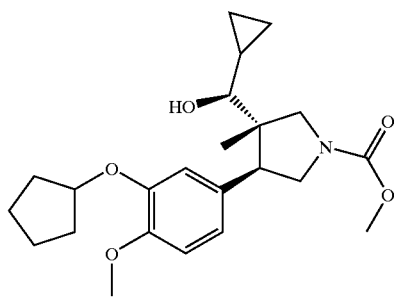
Sample No. 14
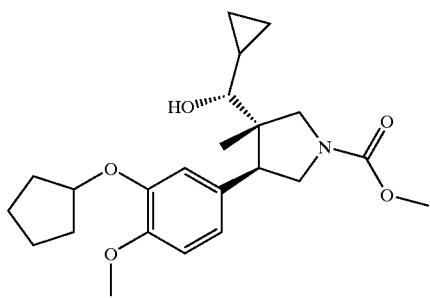
Sample No. 15
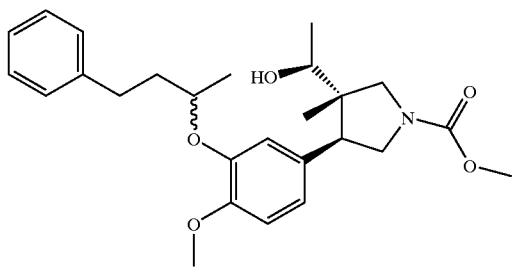
Sample No. 16
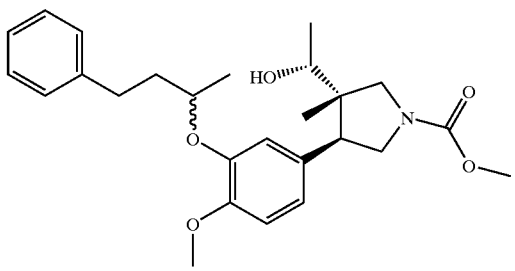
Sample No. 17
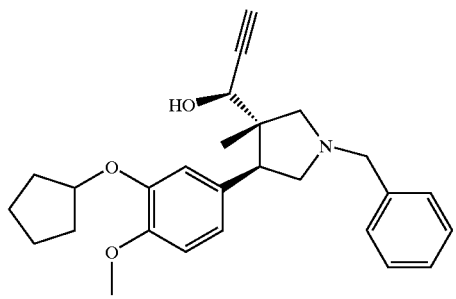
Sample No. 18
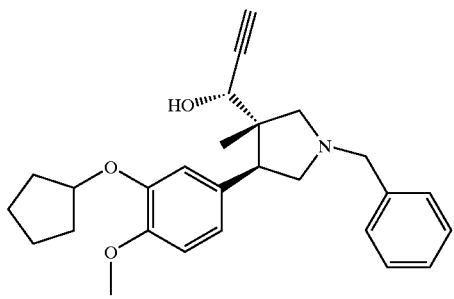
Sample No. 19
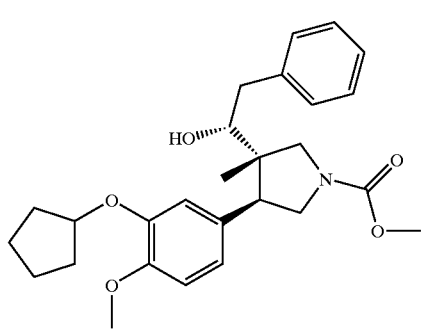
Sample No. 20
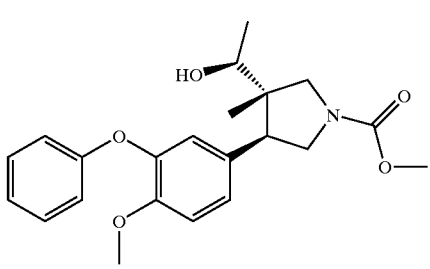
Sample No. 21
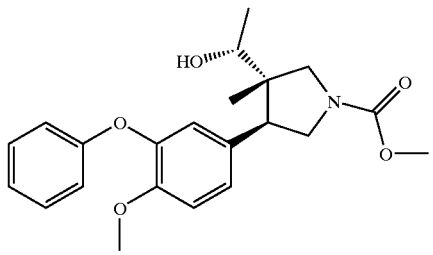
Sample No. 22
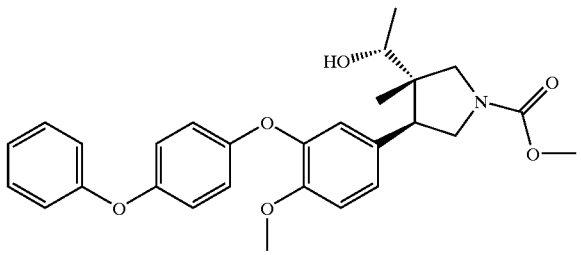

-continued
Sample No. 23
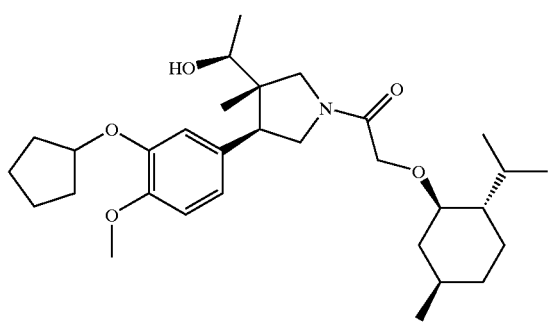
Sample No. 24
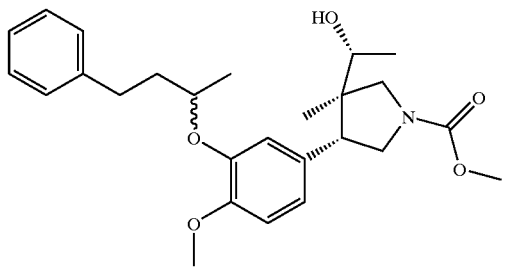
Sample No. 25
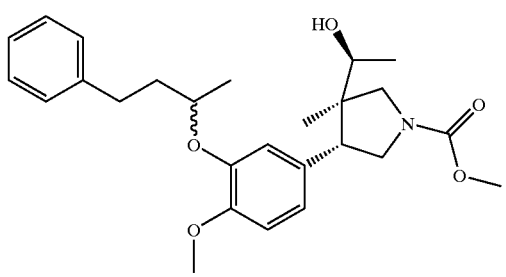
Sample No. 26
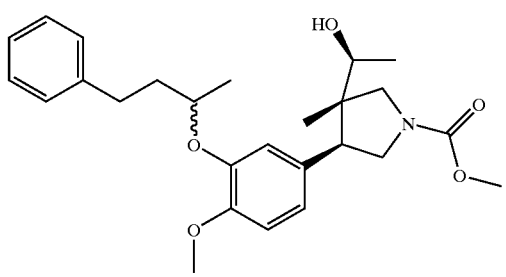
Sample No. 27
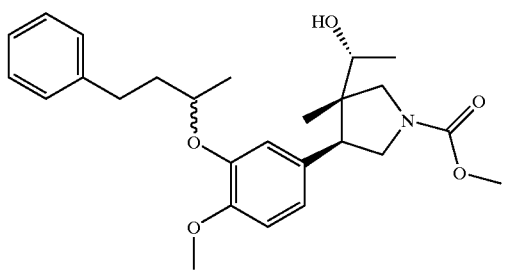
Sample No. 28
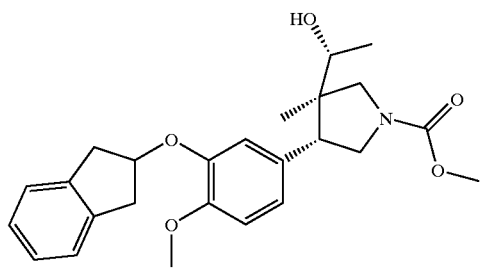
Sample No. 29
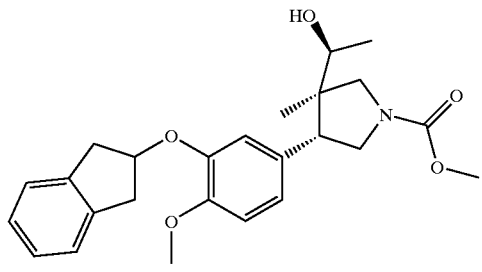
Sample No. 30
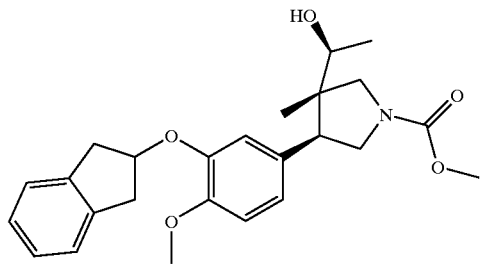
Sample No. 31
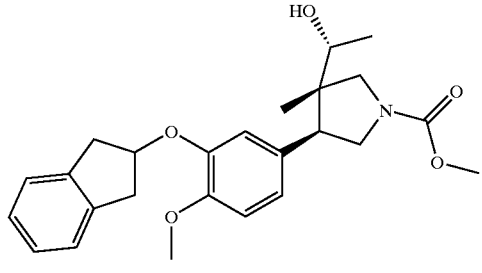
Sample No. 32
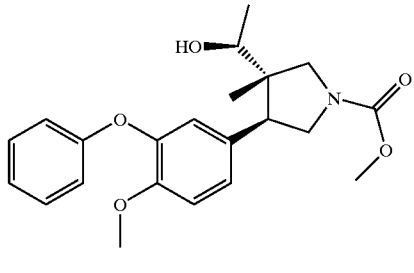

-continued
Sample No. 33
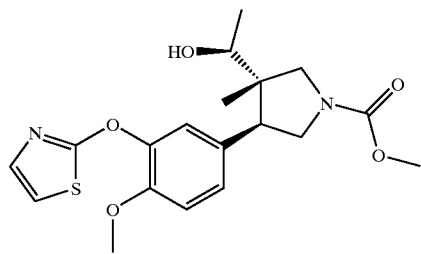
Sample No. 34
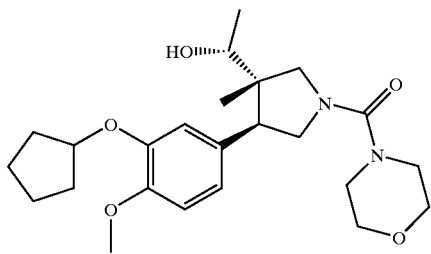
Sample No. 35
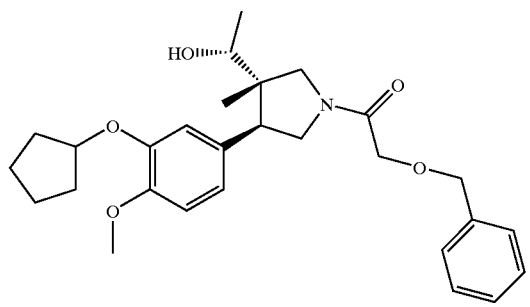
Sample No. 36
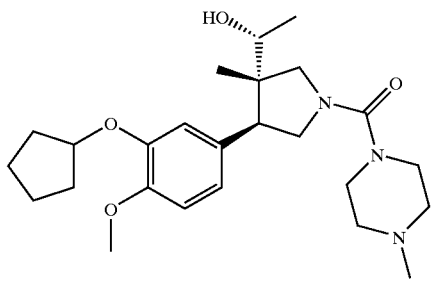
Sample No. 37
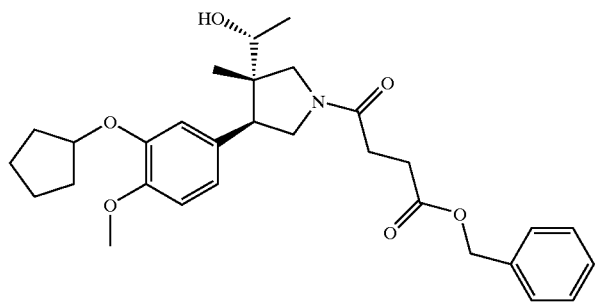
Sample No. 38
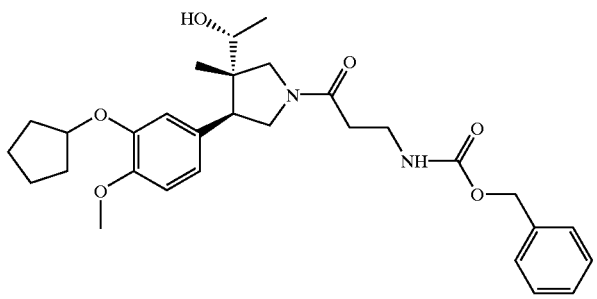
Sample No. 39
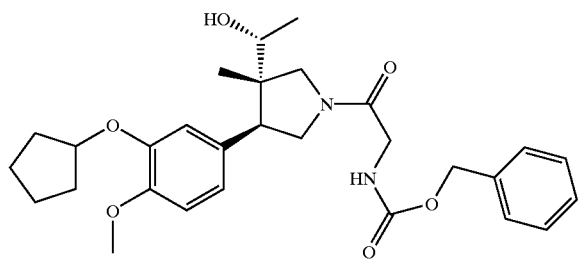
Sample No. 40
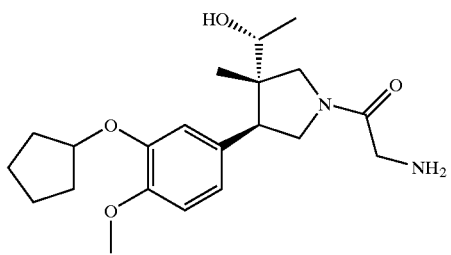
Sample No. 41
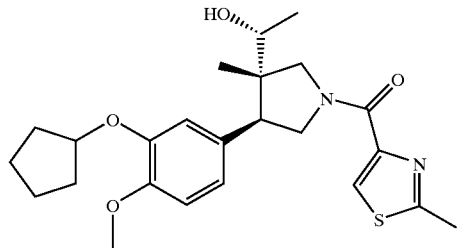
Sample No. 42
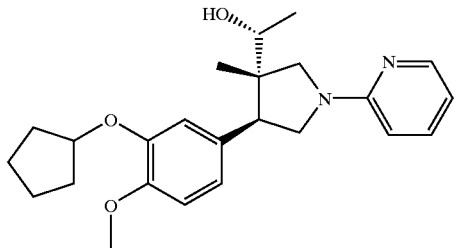

-continued
Sample No. 43
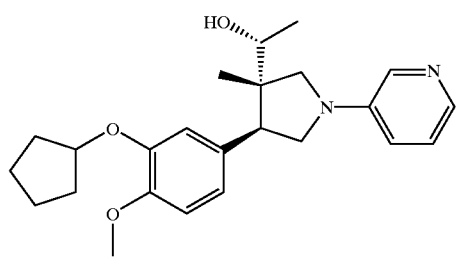
Sample No. 44
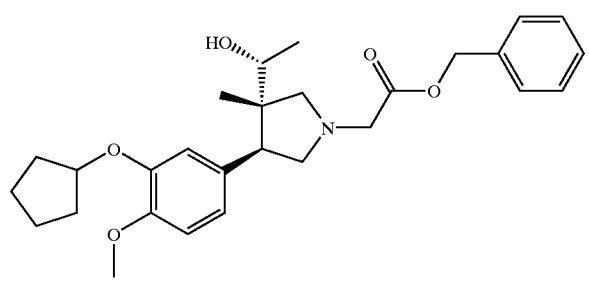
Sample No. 45
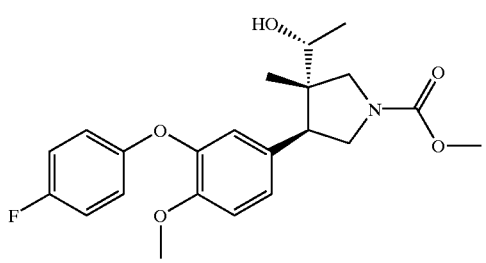
Sample No. 46
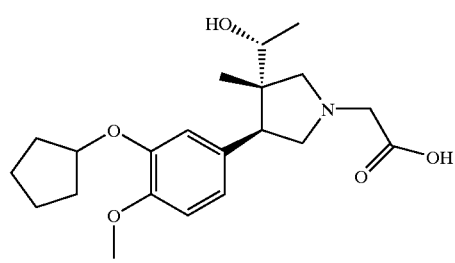
Sample No. 47
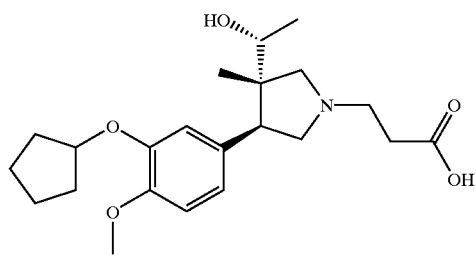
Sample No. 48
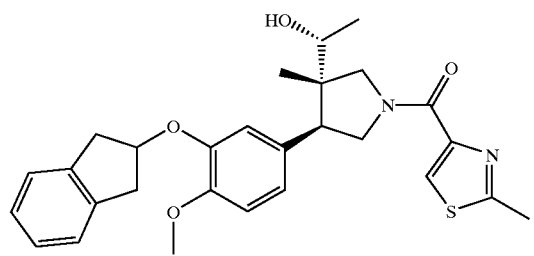
Sample No. 49
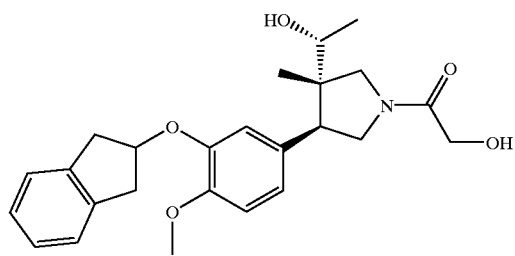
Sample No. 50
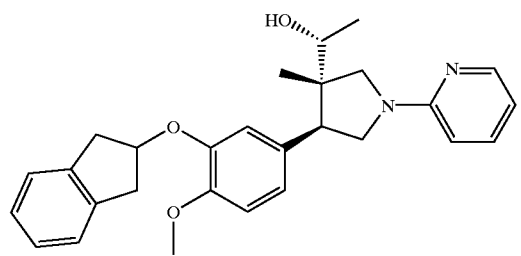
Sample No. 51
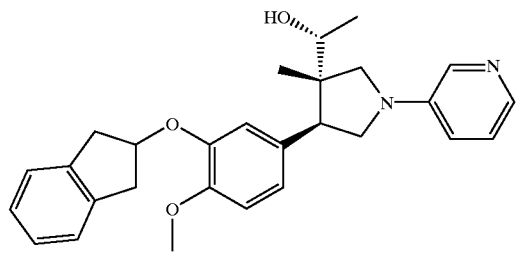
Sample No. 52
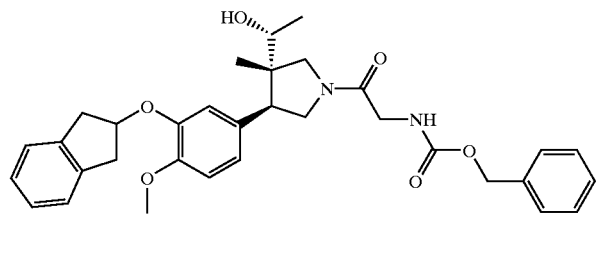

Sample No. 53
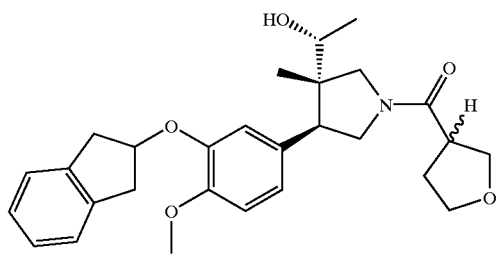
Sample No. 54
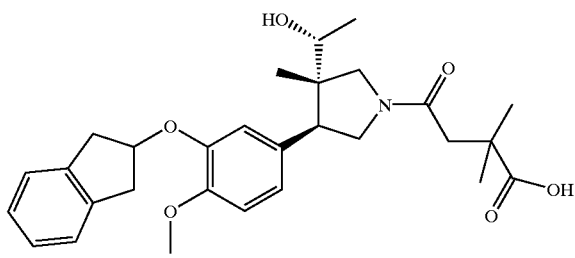
Sample No. 55
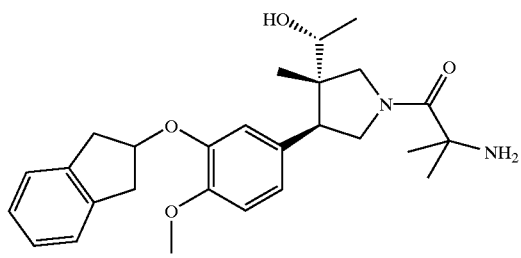
Sample No. 56
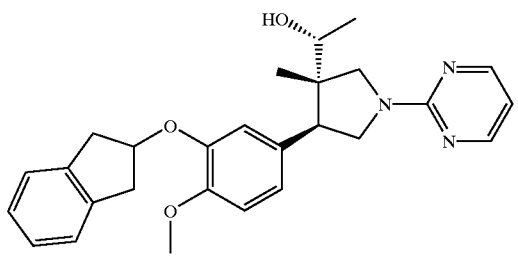
Sample No. 57
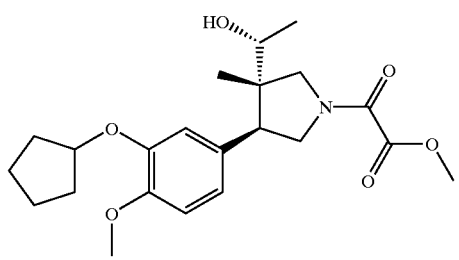
Sample No. 58
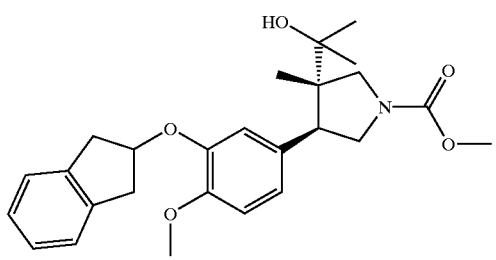
Sample No. 59
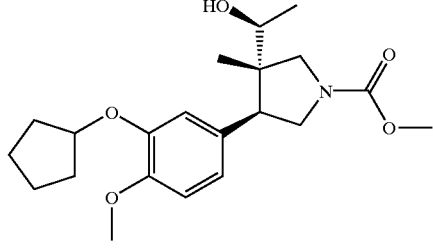
Sample No. 60
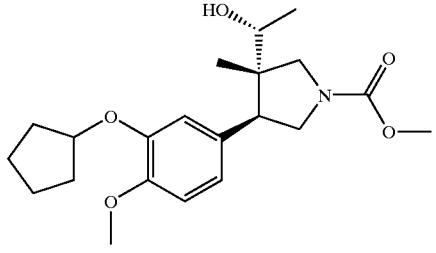
Sample No. 61
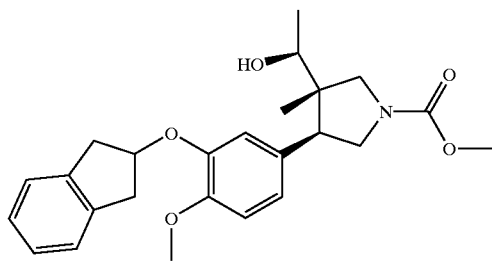
Sample No. 62
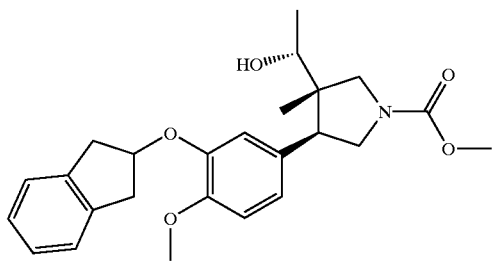
Sample No. 63
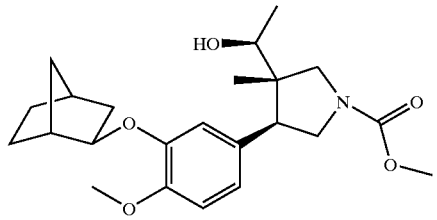
Sample No. 64
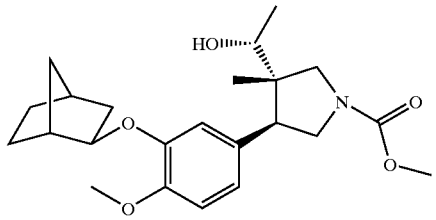

-continued
Sample No. 65
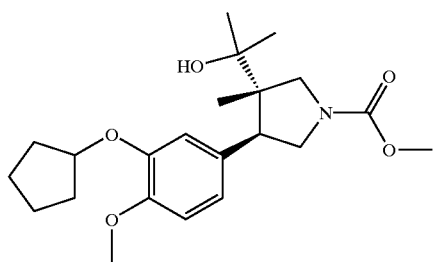
Sample No. 66
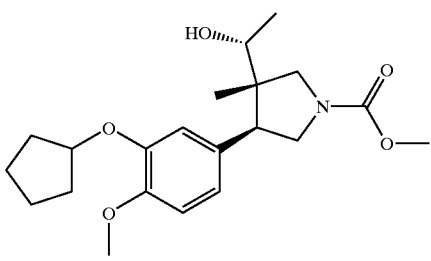
Sample No. 67
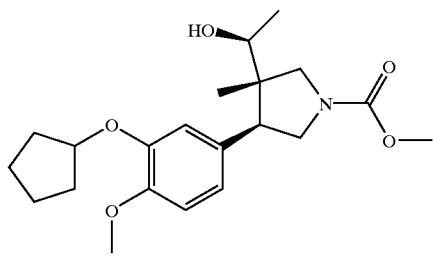
Sample No. 68
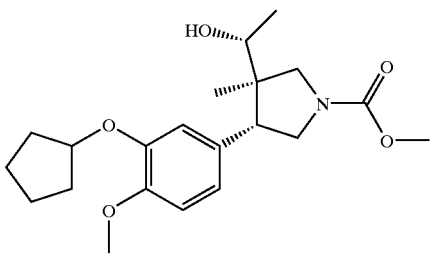
Sample No. 69
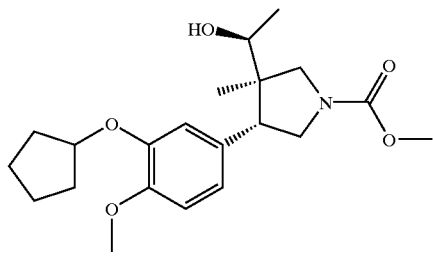
Sample No. 70
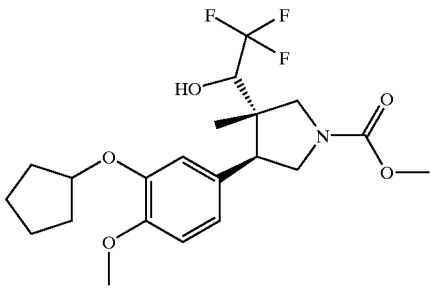
Sample No. 71
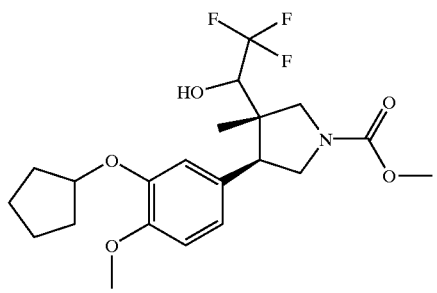
Sample No. 72
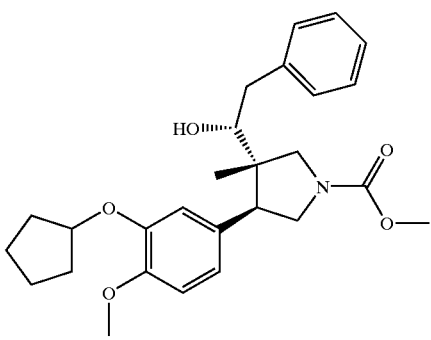
Sample No. 73
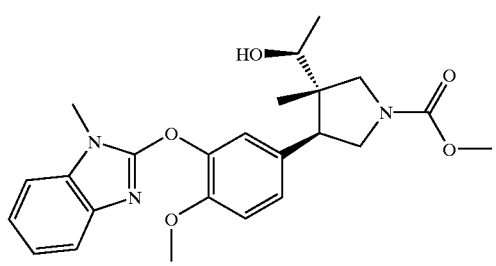
Sample No. 74
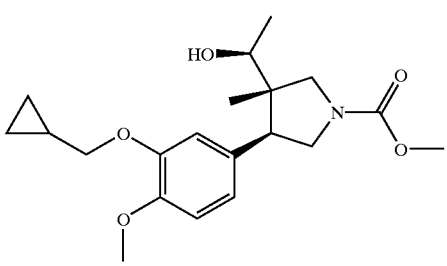

-continued
Sample No. 75
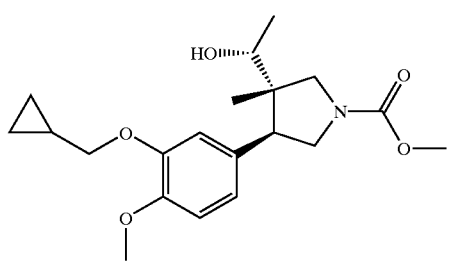
Sample No. 76
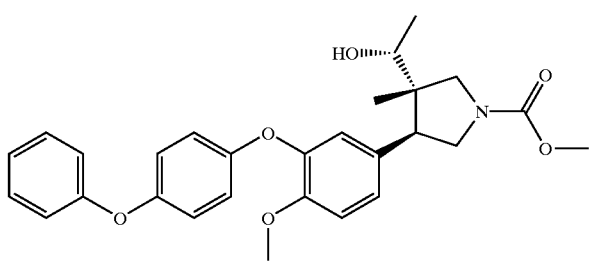
Sample No. 77
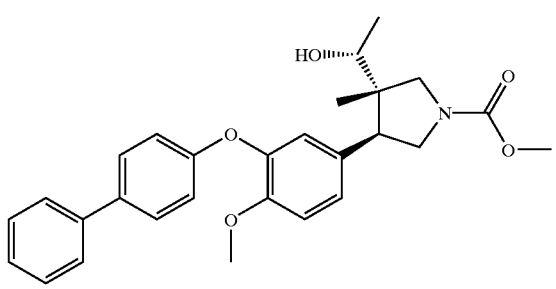
Sample No. 78
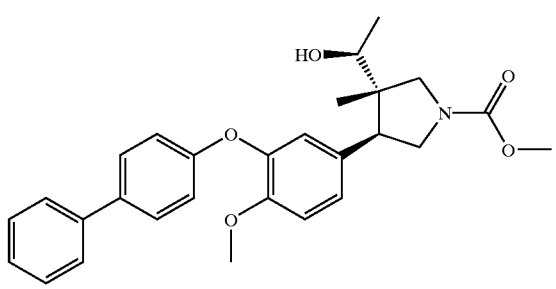
Sample No. 79
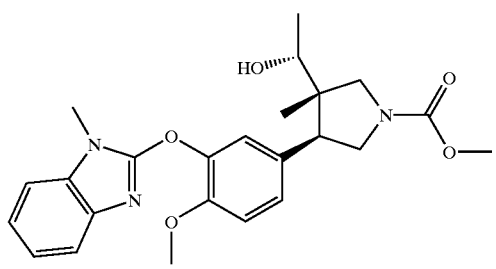
Sample No. 80
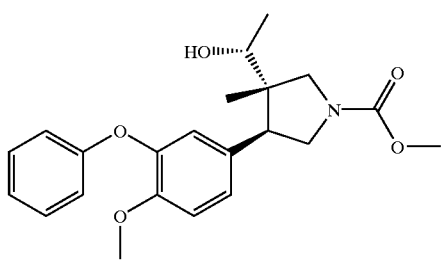
Sample No. 81
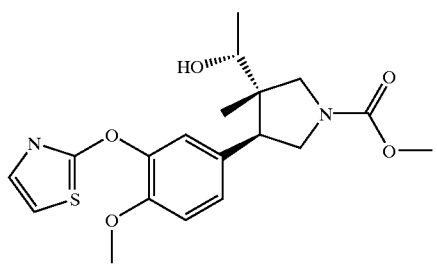
Sample No. 82
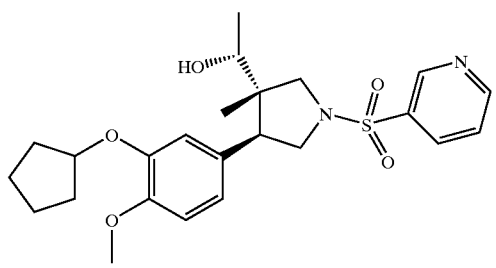
Sample No. 83
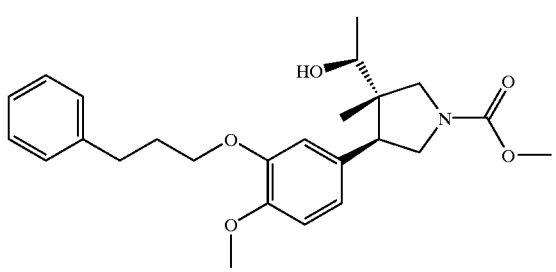
Sample No. 84
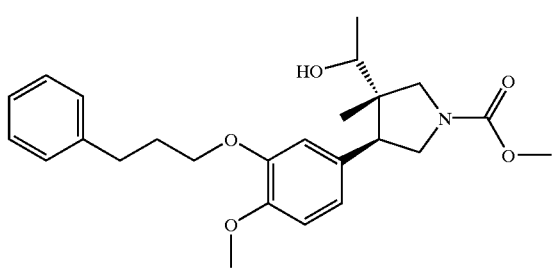

-continued
Sample No. 85
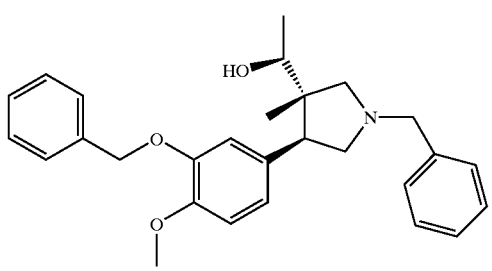
Sample No. 86
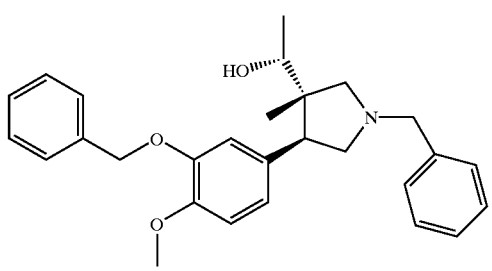
Sample No. 87
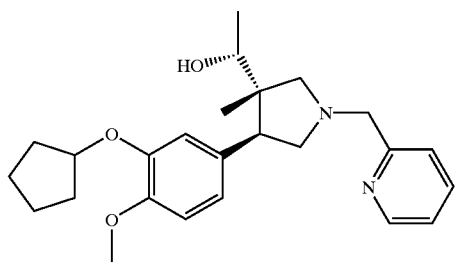
Sample No. 88
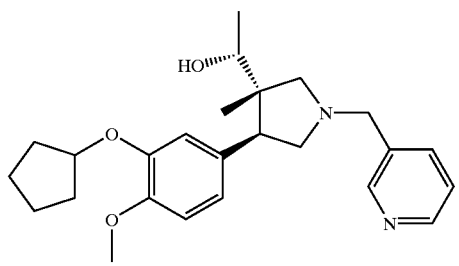
Sample No. 89
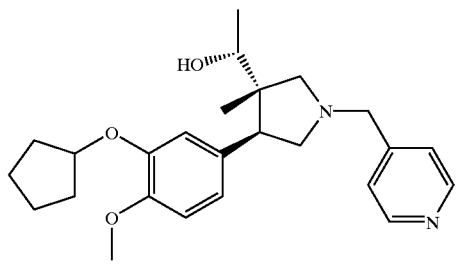
Sample No. 90
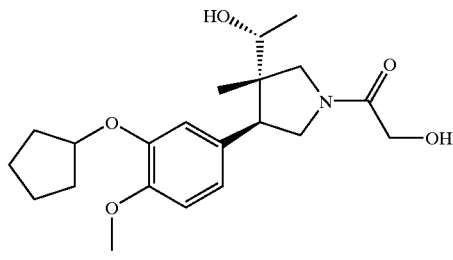
Sample No. 91
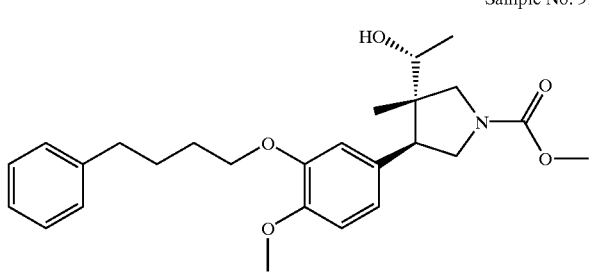
Sample No. 92
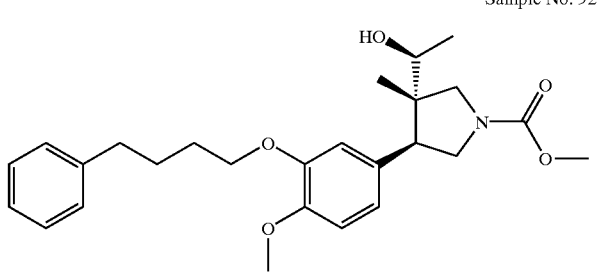
Sample No. 93
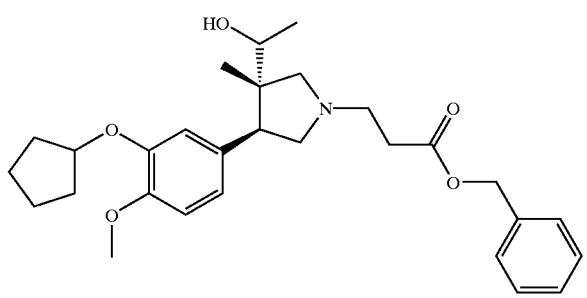
Sample No. 94
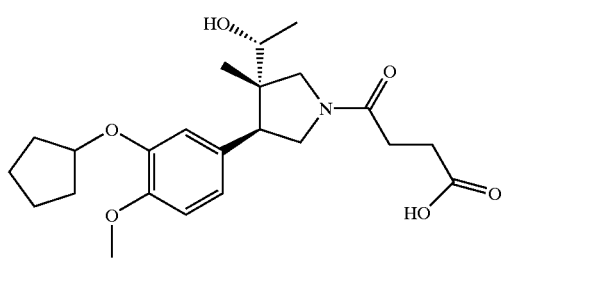

What is claimed is:
1. A compound having a formula:

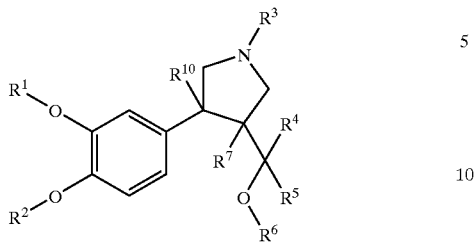

wherein
- $R^1$ is lower alkyl, bridged alkyl, aralkyl, cycloalkyl, a 5- or 6-membered saturated heterocycle, $C_{1-3}$alkylenecycloalkyl, aryl- or heteroaryl-substituted propargyl, aryl- or heteroaryl-substituted allyl, or halocycloalkyl;
- $R^2$ is hydrogen, methyl, or halo-substituted methyl;
- $R^3$ is C(=NH)$NR^8R^9$, C(=O)$NR^8R^9$, aryl, or heteroaryl;
- $R^4$ is hydrogen, lower alkyl, haloalkyl, cycloalkyl, or aryl;
- $R^5$ is lower alkyl, alkynyl, haloalkyl, cycloalkyl, or aryl;
- $R^6$ is hydrogen, lower alkyl, or C(=O)$R^7$;
- $R^7$ is lower alkyl, branched or unbranched, cycloalkyl, or aryl, either optionally substituted with one or more of $R^8O$, $NR^8R^9$, or $SR^8$; and
- $R^8$ and $R^9$, same or different, are selected from the group consisting of hydrogen, lower alkyl, cycloalkyl, aryl, heteroaryl, and aralkyl, or $R^8$ and $R^9$ together form a 4-membered to 7-membered ring;
- $R^{10}$ is hydrogen, alkyl, haloalkyl, cycloalkyl, aryl, C(=O)alkyl, C(=O)cycloalkyl, C(=O)aryl, C(=O)O-alkyl, C(=O)Ocycloalkyl, C(=O)aryl, $CH_2OH$, $CH_2O$alkyl, CHO, CN, $NO_2$, or $SO_2R^{11}$; and
- $R^{11}$ is alkyl, cycloalkyl, trifluoromethyl, aryl, aralkyl, or $NR^8R^9$.

2. The compound of claim 1 having the structure:

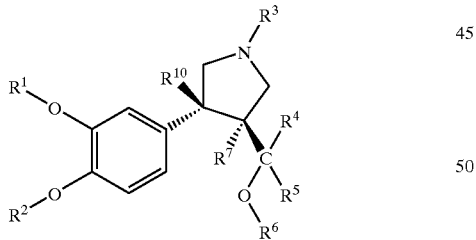

3. The compound of claim 1 wherein $R^1$ is selected from the group consisting of:

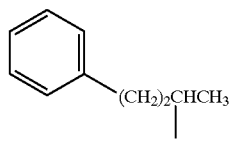

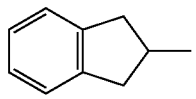

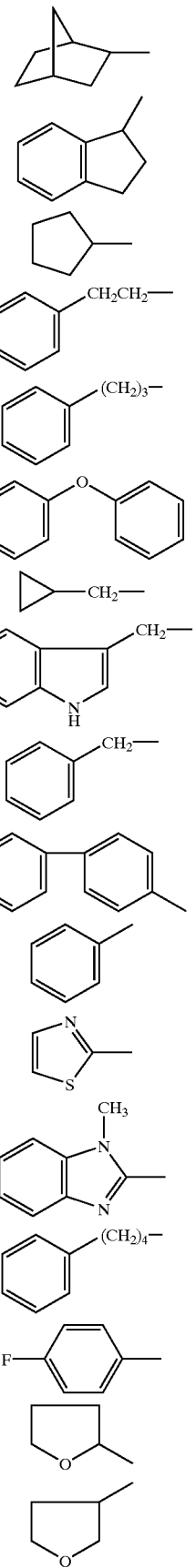

and

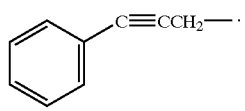

4. The compound of claim 1 wherein $R^4$ is selected from the group consisting of hydrogen, methyl, trifluoromethyl, cyclopropyl, acetyl, ethylnyl, benzyl, and phenyl.

5. The compound of claim 1 wherein $R^5$ is lower alkyl.

6. The compound of claim 1 wherein $R^6$ is selected from the group consisting of hydrogen, acetyl, and benzoyl.

7. The compound of claim 1 wherein $R^7$ is lower alkyl.

8. The compound of claim 1 wherein $R^8$ and $R^9$, independently, are hydrogen or lower alkyl, or together form a 5-membered or 6-membered ring.

9. The compound of claim 1 wherein $R^1$ is selected from the group consisting of cyclopentyl, tetrahydrofuryl, indanyl, norbornyl, phenethyl, and phenylbutyl; $R^2$ is selected from the group consisting of methyl and difluoromethyl; $R^4$ is hydrogen; $R^5$ is methyl; $R^6$ is hydrogen; $R^7$ is methyl; $R^8$ and $R^9$, independently are selected from the group consisting of hydrogen and lower alkyl, or form a 5-membered or 6-membered ring, and $R^{10}$ is hydrogen.

10. The compound of claim 1 having an $IC_{50}$ vs. human recombinant PDE4 of about 700 pM to about 15 μM.

11. The compound of claim 1 having a PBL/TNFα $EC_{50}$ of about 1 nM to about 20 μM.

12. The compound of claim 1 having an $IC_{50}$ vs. human recombinant PDE4 of about 700 pM to about 15 μM, and a PBL/TNFα $EC_{50}$ of about 1 nM to about 20 μM.

13. The compound of claim 1 having an $IC_{50}$ vs. human recombinant PDE4 of about $100 \times 10^{-9}$ M or less.

14. The compound of claim 1 having an $IC_{50}$ vs. human recombinant PDE4 of about $50 \times 10^{-9}$ M or less.

15. The compound of claim 1 having a PBL/TNFα $EC_{50}$ of about $500 \times 10^{-9}$ M or less.

16. The compound of claim 1 having a PBL/TNFα $EC_{50}$ of about $100 \times 10^{-9}$ M or less.

17. The compound of claim 1 having an $IC_{50}$ vs. human recombinant PDE4 of about $100 \times 10^{-9}$ or less and a PBL/TNFα $EC_{50}$ of about $500 \times 10^{-9}$ M or less.

18. The compound of claim 1 having an $IC_{50}$ vs. human recombinant PDE4 of about $50 \times 10^{-9}$ or less and a PBL/TNFα $EC_{50}$ of about $100 \times 10^{-9}$ M or less.

19. A pharmaceutical composition comprising a compound of claim 1 and a pharmaceutically acceptable carrier.

20. A compound having a formula:

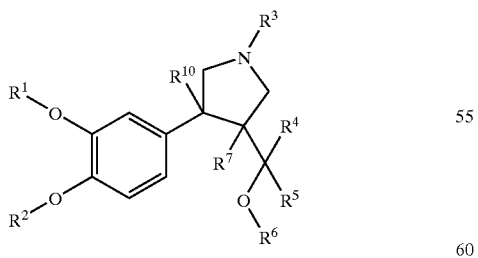

wherein
$R^1$ is lower alkyl, bridged alkyl, aralkyl, cycloalkyl, a 5- or 6-membered saturated heterocycle, $C_{1-3}$alkylenecycloalkyl, aryl- or heteroaryl-substituted propargyl, aryl- or heteroaryl-substituted allyl, or halocycloalkyl;

$R^2$ is hydrogen, methyl, or halo-substituted methyl;

$R^4$ is hydrogen, lower alkyl, haloalkyl, cycloalkyl, or aryl;

$R^5$ is lower alkyl, alkynyl, haloalkyl, cycloalkyl, or aryl;

$R^6$ is hydrogen, lower alkyl, or $C(=O)R^7$;

$R^7$ is lower alkyl, branched or unbranched, cycloalkyl, or aryl, either optionally substituted with one or more of $R^8O$, $NR^8R^9$, or $SR^8$; and $R^8$ and $R^9$, same or different, are selected from the group consisting of hydrogen, lower alkyl, cycloalkyl, aryl, heteroaryl, and aralkyl, or $R^8$ and $R^9$ together form a 4-membered to 7-membered ring;

$R^{10}$ is hydrogen, alkyl, haloalkyl, cycloalkyl, aryl, $C(=O)$alkyl, $C(=O)$cycloalkyl, $C(=O)$aryl, $C(=O)$O-aryl, $C(=O)O$cycloalkyl, $C(=O)$aryl, $CH_2OH$, $CH_2O$alkyl, CHO, CN, $NO_2$, or $SO_2R^{11}$;

$R^{11}$ is alkyl, cycloalkyl, trifluoromethyl, aryl, aralkyl, or $NR^8R^9$; and $R^3$ is selected from the group consisting of:

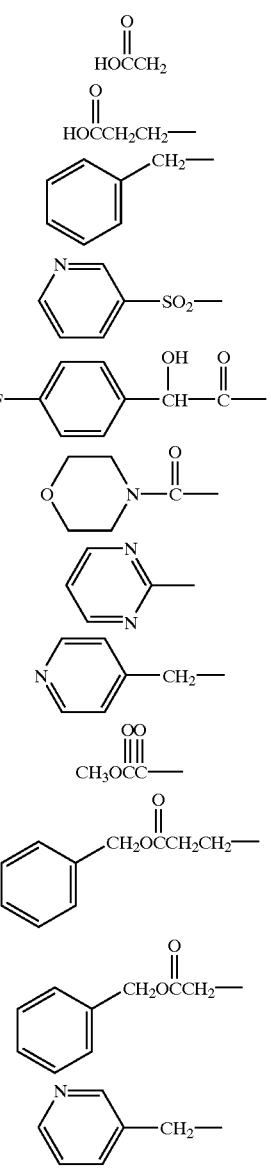

-continued

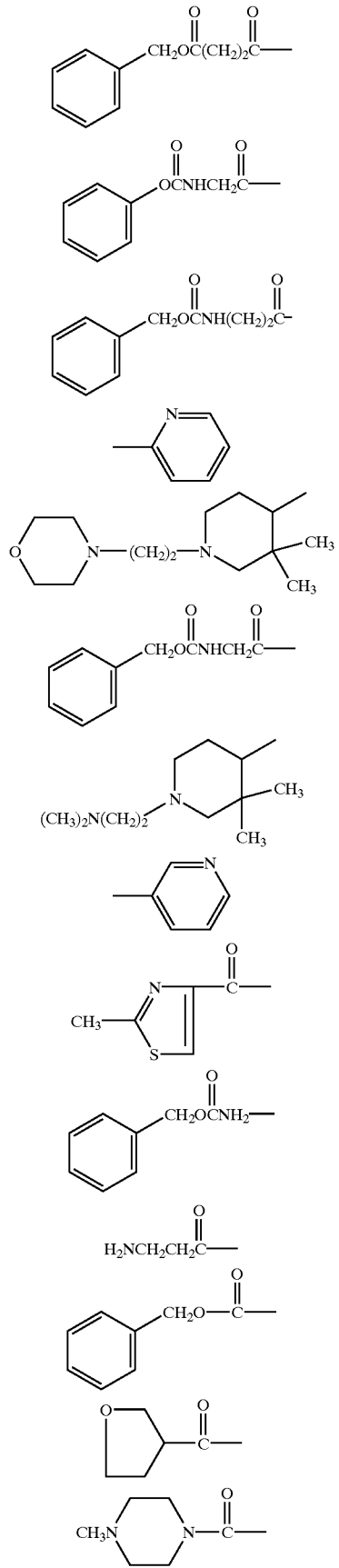

-continued

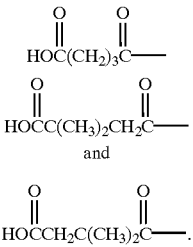

and

21. A compound selected from the group consisting of:

[1-benzyl-4-(3-cyclopentyloxy-4-methoxyphenyl)-3-methyl-pyrrolidin-3-yl]-methanol,
1-[1-benzyl-4-(3-cyclopentyloxy-4-methoxyphenyl)-3-methylpyrrolidin-3-yl]-1-hydroxy-propan-2-one,
3-{[3-((1R)-1-hydroxyethyl)(3S, 4S)-4-(3-cyclopentyloxy-4-methoxyphenyl)-3-methylpyrrolidinyl]sulfonyl}pyridine,
N-{3-[3-((1R)-1-hydroxyethyl)(3S, 4S)-4-(3-cyclopentyloxy-4-methoxyphenyl)-3-methylpyrrolidinyl]-3-oxopropyl}-(phenylmethoxy)carboxamide,
phenylmethyl 4-[3-((1R)-1-hydroxyethyl)(3S, 4S)-4-(3-cyclopentyloxy-4-methoxyphenyl)-3-methylpyrrolidinyl]-4-oxobutanoate,
4-[3-((1R)-1-hydroxyethyl)(3S, 4S)-4-(3-cyclopentyloxy-4-methoxyphenyl)-3-methylpyrrolidinyl]-4-oxobutanoic acid,
N-{2-[3-((1R)-1-hydroxyethyl)(3S, 4S)-4-(3-cyclopentyloxy-4-methoxyphenyl)-3-methylpyrrolidinyl]-2-oxoethyl}-(phenylmethoxy)carboxamide,
3-((1R)-1-hydroxyethyl)(3S, 4S)-4-(3-cyclopentyloxy-4-methoxyphenyl)-3-methylpyrrolidinyl 4-methyl piperazinyl ketone,
3-((1R)-1-hydroxyethyl)(3S, 4S)-4-(3-cyclopentyloxy-4-methoxyphenyl)-3-methylpyrrolidinyl morpholin-4-yl ketone,
1-[3-((1S)-1-hydroxyethyl)(3S, 4S)-4-(3-cyclopentyloxy-4-methoxyphenyl)-3-methylpyrrolidinyl]-2-[(2S, 1R,5R)-5-methyl-2-(methylethyl)cyclohexyloxy]ethan-1-one,
3-((1R)-1-hydroxyethyl)(3S, 4S)-4-(3-cyclopentyloxy-4-methoxyphenyl)-3-methyl pyrrolidinyl 2-methyl (1,3-thiazol-4-yl) ketone,
(1R)-1-[(3S, 4S)-4-(3-cyclopentyloxy-4-methoxyphenyl)-3-methyl-1-(2-pyridylmethyl)pyrrolidin-3-yl]ethan-1-ol,
(1R)-1-[(3S, 4S)-4-(3-cyclopentyloxy-4-methoxyphenyl)-3-methyl-1-(3-pyridylmethyl)pyrrolidin-3-yl]ethan-1-ol,
(1R)-1-[(3S, 4S)-4-(3-cyclopentyloxy-4-methoxyphenyl)-3-methyl-1-(4-pyridylmethyl)pyrrolidin-3-yl]ethan-1-ol,
phenylmethyl 3-[3-((1R)-1-hydroxyethyl) (3S, 4S)-4-(3-cyclopentyloxy-4-methoxyphenyl)-3-methyl pyrrolidinyl]propanoate,
3-[3-((1R)-1-hydroxyethyl)(3S, 4S)-4-(3-cyclopentyloxy-4-methoxyphenyl)-3-methyl pyrrolidinyl]propanoic acid,
phenylmethyl 2-[3-((1R)-1-hydroxyethyl)(3S, 4S)-4-(3-cyclopentyloxy-4-methoxyphenyl)-3-methyl pyrrolidinyl]acetate,
2-[3-((1R)-1-hydroxyethyl)(3S, 4S)-4-(3-cyclopentyloxy-4-methoxyphenyl)-3-methylpyrrolidinyl]acetic acid,
(1R)-1-[(3S, 4S)-4-(3-cylcopentyloxy-4-methoxyphenyl)-3-methyl-1-(2-pyridyl)pyrrolidin-3-yl]ethan-1-ol,
(1R)-1-[(3S, 4S)-4-(3-cyclopentyloxy-4-methoxyphenyl)-3-methyl-1-(3-pyridyl)pyrrolidin-3-yl]ethan-1-ol,
N-{2-[3-((1R)-1-hydroxyethyl)(3S, 4s)-4-(3-indan-2-yloxy-4-methoxyphenyl)-3-methylpyrrolidinyl]-1,1-dimethyl-2-oxoethyl}(phenylmethoxy)carboxamide, 4-[3-((1R)-1-hydroxyethyl)(3S, 4S)-4-(3-indan-2-yloxy-4-methoxyphenyl)-3-methylpyrrolidinyl]-2,2-dimethyl-4-oxobutanoic acid, 3-((1R)-1-hydroxyethyl)(3S, 4S)-4-(3-indan-2-yloxy-4-methoxyphenyl)-3-methylpyrrolidinyl 2-methyl(1,3-thiazol-4-yl) ketone, 3-((1R)-1-hydroxyethyl)(3S, 4R)-4-(3-indan-2-yloxy-4-methoxyphenyl)-3-methylcyclopentyl oxolan-3-yl ketone, N-{2-[3-((1R)-1-hydroxyethyl)(3S, 4S)-4-(3-indan-2-yloxy-4-methoxyphenyl)-3-methylpyrrolidinyl]-2-oxoethyl}(phenylmethoxy)carboxamide, (1R)-1-[(3S, 4S)-4-(3-indan-2-yloxy-4-methoxyphenyl)-3-methyl-1-(2-pyridyl)pyrrolidin-3-yl]ethan-1-ol, (1R)-1-[(3S, 4S)-4-(3-indan-2-yloxy-4-methoxyphenyl)-3-methyl-1-(3-pyridyl)pyrrolidin-3-yl]ethan-1-ol, (1R)-1-[(3S, 4S)-4-(3-indan-2-yloxy-4-methoxyphenyl)-3-methyl-1-pyrimidin-2-ylpyrrolidin-3-yl]ethan-1-ol.

22. The compound of claim 21 selected from the group consisting of:

phenylmethyl 4-[3-((1R)-1-hydroxyethyl)(3S, 4S)-4-(3-cyclopentyloxy-4-methoxyphenyl)-3-methylpyrrolidinyl]-4oxobutanoate, N-{3-[3-((1R)-1-hydroxyethyl)(3S, 4S)-4-(3-cyclopentyloxy-4-methoxyphenyl)-3-methylpyrrolidinyl]-3-oxopropyl}(phenylmethoxy)carboxamide, N-{2-[3-((1R)-1-hdroxyethyl)(3S, 4S)-4-(3-cyclopentyloxy-4-methoxyphenyl)-3-methylpyrrolidinyl]-2-oxoethyl}(phenylmethoxy)carboxamide, (1R)-1-[(3S, 4S)-4-(3-indan-2-yloxy-4-methoxyphenyl)-3-methyl-1-(3-pyridyl)pyrrolidin-3-yl]ethan-1-ol, (1R)-1-[(3S, 4S)-4-(3-indan-2-yloxy-4-methoxyphenyl)-3-methyl-1-pyrimidin-2-ylpyrrolidin-3-yl]ethan-1-ol, 3-((1R)-1-hydroxyethyl)(3S, 4S)-4-(3-cyclopentyloxy-4-methoxyphenyl)-3-methylpyrrolidinyl morpholin-4-yl ketone.

* * * * *

UNITED STATES PATENT AND TRADEMARK OFFICE
CERTIFICATE OF CORRECTION

PATENT NO.    : 6,458,787 B1
DATED         : October 1, 2002
INVENTOR(S)   : Martins et al.

It is certified that error appears in the above-identified patent and that said Letters Patent is hereby corrected as shown below:

<u>Title page,</u>
Item [56], References Cited, OTHER PUBLICATION, "Robichaud et al." reference, "Phosehodiesterase" should be -- Phosphodiesterase --
"Klodzinska et al." reference, *"Neuropharnacology,"* should be
-- *Neuropharmacology,* --

<u>Column 2,</u>
Line 62, "IL-1, β" should be -- IL-1β --

<u>Column 5,</u>
Line 24, "$C_{13}$" should be -- $C_{1-3}$ --
Line 26, "-$CH_2C=C$-" should be -- -$CH_2C\equiv C$-C- --

<u>Column 6,</u>
Line 16, "$C_{13}$" should be -- $C_{1-3}$ --
Line 18, "-$CH_2C=C$-" should be -- -$CH_2C\equiv C$-C- --

<u>Column 7,</u>
Line 58, "Alkylthiol" should be -- Alkylthio --

<u>Column 16,</u>
Middle structure captioned "Int. 3," "dr-10.1" should be -- dr~1:1 --

<u>Column 17,</u>
Structure on left-hand side captioned "Int. 39," "dr~1.1" should be -- dr~1:1 --

Signed and Sealed this

Tenth Day of August, 2004

JON W. DUDAS
*Acting Director of the United States Patent and Trademark Office*